US012630540B2

(12) United States Patent
Bender et al.

(10) Patent No.: US 12,630,540 B2
(45) Date of Patent: May 19, 2026

(54) (4-(6-((2-OCTAHYDROCYCLOPENTA[C]PYRROL-5-YL)AMINO)PYRIDAZIN-3-YL)PHENYL)(IMINO)(METHYL)-LAMBDA6-SULFANONE DERIVATIVES AND SIMILAR COMPOUNDS AS MUSCARINIC ACETYLCHOLINE RECEPTOR M4 ANTAGONISTS FOR THE TREATMENT OF NEURODEGENERATIVE DISORDERS

(71) Applicant: Vanderbilt University, Nashville, TN (US)

(72) Inventors: Aaron M. Bender, Spring Hill, TN (US); Changho Han, Nashville, TN (US); Matthew Spock, Nashville, TN (US); Cori A. Malinky, Nashville, TN (US); Craig W. Lindsley, Brentwood, TN (US); P. Jeffrey Conn, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 370 days.

(21) Appl. No.: 18/567,212

(22) PCT Filed: Jun. 10, 2022

(86) PCT No.: PCT/US2022/032994
§ 371 (c)(1),
(2) Date: Dec. 5, 2023

(87) PCT Pub. No.: WO2022/261427
PCT Pub. Date: Dec. 15, 2022

(65) Prior Publication Data
US 2024/0287050 A1 Aug. 29, 2024

Related U.S. Application Data

(60) Provisional application No. 63/209,788, filed on Jun. 11, 2021.

(51) Int. Cl.
*C07D 405/14* (2006.01)
*A61K 31/501* (2006.01)
(Continued)

(52) U.S. Cl.
CPC .......... *C07D 405/14* (2013.01); *A61K 31/501* (2013.01); *C07D 401/14* (2013.01); *C07D 403/12* (2013.01)

(58) Field of Classification Search
CPC .. C07D 405/14; C07D 401/14; C07D 403/12; A61K 31/501; A61P 25/00; A61P 25/14; A61P 25/16; A61P 25/18; A61P 25/28
See application file for complete search history.

(56) References Cited

U.S. PATENT DOCUMENTS 11,299,481 B2 4/2022 Lindsley et al.
11,820,757 B2 11/2023 Lindsley et al.
(Continued)

FOREIGN PATENT DOCUMENTS

WO 2019079783 A1 4/2019
WO 2021067696 A1 4/2021
(Continued)

OTHER PUBLICATIONS

CAS Registry No. 2307718-06-3 (which entered the STN database on May 14, 2019). (Year: 2019).*
(Continued)

*Primary Examiner* — Kamal A Saeed
*Assistant Examiner* — Meghan C Heasley
(74) *Attorney, Agent, or Firm* — COOLEY LLP

(57) ABSTRACT

Disclosed are compounds of formula (I) wherein $G^1$ is as antagonists of the muscarinic acetylcholine receptor $M_4$ (mAChR $M_4$) for use in the treatment of e.g. a neurodegenerative disorder, a movement disorder, or a brain disorder, such as e.g. Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy. An exemplary compound is e.g. (2,5-difluoro-4-(6-(((3aR,5s,6aS)-2-((tetrahydro-2H-pyran-4-yl)methyl)octahydrocyclopenta[c]pyrrol-5-yl)amino)pyridazin-3-yl)phenyl)(imino)(methyl)-λ$^6$-sulfanone (e.g. example 12; compound no. 7) Pharmacological data on the activity of the compounds in an mAChR $M_4$ cell-based assay are provided (e.g. table 2).

(I)

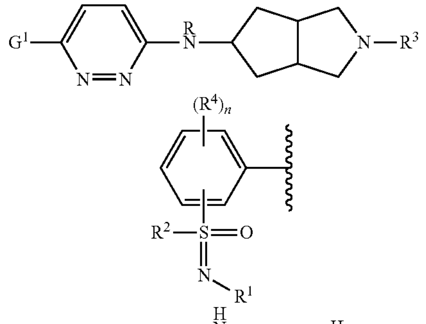

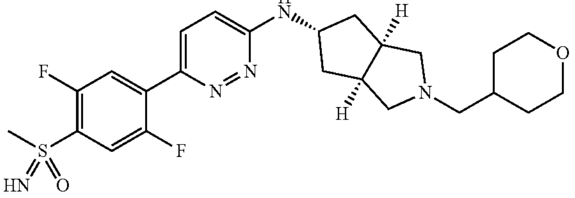

(Continued)

TABLE 2

| | Human $M_4$ | |
|---|---|---|
| Cpd. No. | $IC_{50}$ (nM) | $E_{min}$ (%)* |
| 1 | 13.4 | 4 |
| 2 | 39.6 | 2 |
| 3 | 18.5 | 3 |
| 4 | 584 | 6 |
| 5 | 75.4 | 3 |
| 6 | 188 | 3 |
| 7 | 46.0 | 3 |
| 8 | 560 | 7 |
| 9 | 18.4 | 3 |
| 10 | 1.8 | 2 |
| 11 | 86.2 | 3 |
| 12 | 43.4 | 2 |
| 13 | 8.6 | 3 |

*% ACh maximum at 30 μM.

20 Claims, No Drawings

(51) Int. Cl.
*C07D 401/14* (2006.01)
*C07D 403/12* (2006.01)

(56) References Cited

U.S. PATENT DOCUMENTS

2021/0188820 A1 6/2021 Lindsley et al.
2022/0213069 A1 7/2022 Lindsley et al.
2023/0122344 A1 4/2023 Lindsley et al.
2023/0150986 A1 5/2023 Lindsley et al.
2023/0183218 A1 6/2023 Lindsley et al.
2023/0183219 A1 6/2023 Lindsley et al.
2023/0322799 A1 10/2023 Bender et al.
2024/0010640 A1 1/2024 Bender et al.
2024/0083907 A1 3/2024 Lindsley et al.
2024/0109873 A1 4/2024 Bender et al.
2024/0116902 A1 4/2024 Lindsley et al.

FOREIGN PATENT DOCUMENTS

WO 2021119254 A1 6/2021
WO 2021119265 A1 6/2021
WO 2021216949 A1 10/2021
WO 2021216951 A1 10/2021
WO 2022036177 A1 2/2022
WO 2022109099 A1 5/2022
WO 2022140499 A1 6/2022
WO 2022212819 A1 10/2022
WO 2022216655 A1 10/2022
WO 2022261427 A1 12/2022
WO 2023102100 A1 6/2023

OTHER PUBLICATIONS

International Search Report and Written Opinion for Application No. PCT/US2022/032994 dated Sep. 9, 2022 (15 pages).
International Preliminary Report on Patentability for Application No. PCT/US2022/032994 dated Nov. 21, 2023 (7 pages).

* cited by examiner

(4-(6-((2-OCTAHYDROCYCLOPENTA[C]PYRROL-5-YL)AMINO)PYRIDAZIN-3-YL)PHENYL)(IMINO)(METHYL)-LAMBDA6-SULFANONE DERIVATIVES AND SIMILAR COMPOUNDS AS MUSCARINIC ACETYLCHOLINE RECEPTOR M4 ANTAGONISTS FOR THE TREATMENT OF NEURODEGENERATIVE DISORDERS

RELATED APPLICATIONS

This patent application is the U.S. national stage entry, under 35 U.S.C. § 371, of International Application Number PCT/US2022/032994, filed Jun. 10, 2022, which claims priority to U.S. Provisional Application No. 63/209,788, filed Jun. 11, 2021, the entire contents of each of which are hereby incorporated by reference.

STATEMENT OF GOVERNMENT INTEREST

This invention was made with government support under grant W81XWH-19-1-0355 awarded by the Department of Defense. The government has certain right in the Invention.

TECHNICAL FIELD

The present disclosure relates to compounds, compositions, and methods for treating disorders associated with muscarinic acetylcholine receptor dysfunction.

BACKGROUND

Parkinson's disease (PD) is the second most common neurodegenerative disease with an increasing prevalence as a function of age. Moreover, early-onset PD is also increasing. A hallmark of PD is the progressive degeneration and loss of dopaminergic neurons in the substantia nigra (SN) and basal ganglia (BG), leading to pronounced motor symptoms including bradykinesia, tremor, rigidity, gait dysfunction and postural instability. At present, levodopa (L-DOPA) is the standard of care for treating the motor symptoms, but it is not curative, and prolonged use can engender L-DOPA induced dyskinesia (LID).

Prior to L-DOPA, compounds with anticholinergic activity represented the preferred mode of PD treatment. Cholinergic neurons provide important neuromodulatory control of the BG motor circuit. While the actions of cholinergic pathways on basal ganglia pathways are complex, activation of muscarinic acetylcholine receptors (mAChRs) generally have actions that oppose dopamine (DA) signaling. For instance, mAChR agonists inhibit DA release, and inhibit multiple behavioral effects of drugs that increase DA levels and signaling. Interestingly, muscarinic acetylcholine receptor (mAChR) antagonists were the first available treatments for PD and are still widely used for treatment of this disorder. While many studies of the actions of mAChR antagonists were carried out before randomized controlled trials were introduced, recent well controlled double-blind cross-over design studies demonstrate significant improvement in multiple aspects of motor function in patients receiving mAChR antagonists. Unfortunately, mAChR antagonists have a number of dose-limiting adverse effects that severely limit their clinical utility, including multiple peripheral adverse effects, as well as confusion and severe cognitive disturbances.

Because adverse effects associated with mAChR antagonists limit the doses that can be tolerated, previous clinical studies may underestimate the efficacy that could be achieved if doses of mAChR antagonists could be increased to achieve more complete blockade of specific mAChR subtypes responsible for the antiparkinsonian effects of these agents. The mAChRs include five subtypes, termed $M_1$-$M_5$. Available mAChR antagonists, such as scopolamine, are nonselective across these subtypes, and many of their adverse effects are likely mediated by mAChR subtypes that are not involved in the antiparkinsonian activity. Thus, compounds possessing a more selective profile for individual mAChRs may offer an advantage in PD, as well as related disorders such as dystonia. For example, some studies indicate that the $M_4$ mAChR subtype may play a dominant role in mAChR regulation of basal ganglia motor function.

SUMMARY

One aspect of the invention provides compounds of formula (I),

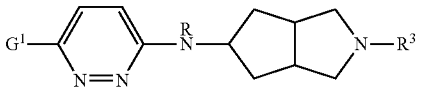

(I)

or a pharmaceutically acceptable salt thereof, wherein:

$G^1$ is

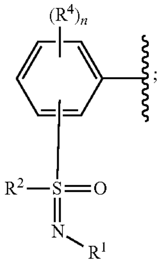

R is hydrogen, $C_{1-4}$alkyl, $C_{3-4}$cycloalkyl, or —$C_{1-3}$alkylene-$C_{3-4}$cycloalkyl;

$R^1$ is hydrogen, $C_{1-4}$alkyl, $C_{1-2}$fluoroalkyl, $C_{3-4}$cycloalkyl, —$C_{1-3}$alkylene-$C_{3-4}$cycloalkyl, or —C(O)$C_{1-4}$alkyl;

$R^2$ is $C_{1-4}$alkyl, $C_{1-2}$fluoroalkyl, $C_{3-4}$cycloalkyl, or —$C_{1-3}$alkylene-$C_{3-4}$cycloalkyl;

$R^3$ is -$L^1$-$G^2$, $G^2$, -$L^2$-$G^2$, -$L^2$-$L^1$-$G^2$, —$C_{2-6}$alkylene-$R^{3a}$, $C_{3-7}$alkyl, or $C_{3-7}$haloalkyl;

$R^4$, at each occurrence, is independently halogen, cyano, $C_{1-4}$alkyl, $C_{1-2}$fluoroalkyl, OH, —$OC_{1-4}$ alkyl, or —$OC_{1-2}$fluoroalkyl;

n is 0, 1, 2, 3, or 4;

$L^1$ is $C_{1-5}$alkylene;

$L^2$ is 1,1-cyclopropylene;

$G^2$ is a 4- to 12-membered heterocyclyl, a 6- to 12-membered aryl, a 5- to 12-membered heteroaryl, or a $C_{3-12}$carbocyclyl optionally fused to a 6-membered arene, wherein $G^2$ is optionally substituted with 1-5 substituents independently selected from the group consisting of halogen, cyano, oxo, $C_{1-4}$alkyl, $C_{1-4}$haloalkyl, —$OR^{13}$, —$N(R^{13})_2$, —$C_{1-3}$alkylene-$OR^3$, and —$C_{1-3}$alkylene-$N(R^{13})_2$;

$R^{3a}$ is —$OR^{14}$ or —$N(R^{14})_2$;

$R^{13}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{13}$, together with a nitrogen to which the two $R^{13}$ attach form a 4- to 6-membered heterocyclic ring optionally substituted with 1-4 substituents independently selected from the group consisting of halogen and $C_{1-4}$alkyl;

$R^{14}$, at each occurrence, is independently hydrogen, $C_{1-4}$alkyl, $C_{1-4}$haloalkyl, $G^3$, or —$C_{1-3}$alkylene-$G^3$, wherein alternatively two $R^{14}$, together with a nitrogen to which the two $R^{14}$ attach form a 4- to 6-membered heterocyclic ring optionally substituted with 1-4 substituents independently selected from the group consisting of halogen and $C_{1-4}$alkyl;

$G^3$ is phenyl, a monocyclic 5- to 6-membered heteroaryl, a monocyclic 4- to 8-membered heterocyclyl, or a monocyclic $C_{3-8}$cycloalkyl, wherein $G^3$ is optionally substituted with 1-5 substituents independently selected from the group consisting of halogen, cyano, $C_{1-4}$alkyl, $C_{1-4}$haloalkyl, oxo, —$OR^{15}$—, and —$N(R^{15})_2$; and $R^{15}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{15}$, together with a nitrogen to which the two $R^{15}$ attach form a 4- to 6-membered heterocyclic ring optionally substituted with 1-4 substituents independently selected from the group consisting of halogen and $C_{1-4}$alkyl.

In another aspect, the invention provides a pharmaceutical composition comprising a compound of formula (I), or a pharmaceutically acceptable salt thereof, and a pharmaceutically acceptable carrier.

In another aspect, the invention provides a method of treating a disorder in a subject, wherein the subject would benefit from antagonism of mAChR $M_4$, comprising administering to the subject a therapeutically effective amount of a compound of formula (I), or a pharmaceutically acceptable salt or composition thereof.

In another aspect, the invention provides a method for antagonizing mAChR $M_4$ in a subject, comprising administering to the subject a therapeutically effective amount of a compound of formula (I), or a pharmaceutically acceptable salt or composition thereof.

In another aspect, the invention provides a method for the treatment of a neurodegenerative disorder, a movement disorder, or a brain disorder comprising administering to a subject in need thereof, a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of a neurodegenerative disorder, a movement disorder, or a brain disorder.

In another aspect, the invention provides a compound of formula (I), or a pharmaceutically acceptable salt or composition thereof, for use in antagonizing mAChR $M_4$ in a subject.

In another aspect, the invention provides the use of a compound of formula (I), or a pharmaceutically acceptable salt or composition thereof, in the manufacture of a medicament for the treatment of a neurodegenerative disorder, a movement disorder, or a brain disorder.

In another aspect, the invention provides the use of a compound of formula (I), or a pharmaceutically acceptable salt or composition thereof, in the manufacture of a medicament for antagonizing mAChR $M_4$ in a subject.

In another aspect, the invention provides a kit comprising a compound of formula (I), or a pharmaceutically acceptable salt or composition thereof, and instructions for use.

DETAILED DESCRIPTION

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's Advanced *Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

The term "alkoxy," as used herein, refers to a group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain saturated hydrocarbon. Representative examples of alkylene include, but are not limited to, $—CH_2—$, $-CD_2-$, $—CH_2CH_2—$, $—C(CH_3)(H)—$, $—C(CH_3)(D)-$, $—CH_2CH_2CH_2—$, $—CH_2CH_2CH_2CH_2—$, and $—CH_2CH_2CH_2CH_2CH_2—$.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means $—NR_xR_y$, wherein $R_y$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be $—NR_x—$, wherein $R_y$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl. Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The term "1,1-carbocyclylene" means a geminal divalent group derived from a cycloalkyl. A representative example is 1,1-$C_{3-6}$cycloalkylene (i.e., 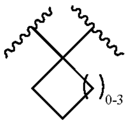 ).

A further example is 1,1-cyclopropylene (i.e., 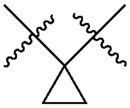 ).

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "difluoroalkyl," as used herein, means an alkyl group, as defined herein, in which two hydrogen atoms are replaced by fluorine. Representative examples of difluoroalkyl include difluoromethyl and difluoroethyl.

The term "fluoroalkylene," as used herein, means an alkylene group, as defined herein, in which one, two, three, four, five, six, seven or eight hydrogen atoms are replaced by fluorine. Representative examples of fluoroalkylene include, but are not limited to $—CF_2—$, $—CH_2CF_2—$, 1,2-difluoroethylene, 1,1,2,2-tetrafluoroethylene, 1,3,3,3-tetrafluoropropylene, 1,1,2,3,3-pentafluoropropylene, and perfluoropropylene such as 1,1,2,2,3,3-hexafluoropropylene.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means $C_1$, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaromatic ring (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl is an 8- to 12-membered ring system and includes a fused bicyclic heteroaromatic ring system (i.e., 10n electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, tetrahydrothiopyranyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane (e.g., 7- to 12-membered fused bicyclic heterocyclyl ring system such as hexahydro-2H-cyclopenta[b]furanyl, octahydro-3aH-cyclohepta[b]furanyl, or 3-oxabicyclo[3.1.0]hexanyl), or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group (e.g., a 7- to 12-membered spiro heterocyclyl ring system such as 2-oxaspiro[3.3]heptanyl, 3-oxaspiro[5.5]undecanyl, 6-oxaspiro[2.5]octanyl, or 5-oxaspiro[2.4]heptanyl), or a bridged heterocycle ring system in which two non-adjacent atoms of the ring are linked by an alkylene bridge of 1, 2, 3, or 4 carbon atoms (e.g., a 6- to 10-membered bridged bicyclic heterocyclyl ring system such as 7-oxabicyclo[2.2.1]heptanyl or 2-oxabicyclo[2.1.1]hexanyl), or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, tetrahydroisoquinolinyl, 7-oxabicyclo[2.2.1]heptanyl, hexahydro-2H-cyclopenta[b]furanyl, 2-oxaspiro[3.3]heptanyl, 3-oxaspiro[5.5]undecanyl, 6-oxaspiro[2.5]octan-1-yl, and 3-oxabicyclo[3.1.0]hexan-6-yl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocyclyls are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "mAChR $M_4$ receptor antagonist" as used herein refers to any exogenously administered compound or agent that directly or indirectly antagonizes mAChR $M_4$, for example in an animal, in particular a mammal (e.g., a human).

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, the invention provides compounds of formula (I), wherein R, $R^1$, $R^2$, $R^3$, $R^4$, and n are as defined herein.

Unsubstituted or substituted rings (i.e., optionally substituted) such as aryl, heteroaryl, etc. are composed of both a ring system and the ring system's optional substituents. Accordingly, the ring system may be defined independently of its substituents, such that redefining only the ring system leaves any previous optional substituents present. For example, a 5- to 12-membered heteroaryl with optional substituents may be further defined by specifying the ring system of the 5- to 12-membered heteroaryl is a 5- to 6-membered heteroaryl (i.e., 5- to 6-membered heteroaryl ring system), in which case the optional substituents of the 5- to 12-membered heteroaryl are still present on the 5- to 6-membered heteroaryl, unless otherwise expressly indicated.

In the following, numbered embodiments of the invention are disclosed. The first embodiment is denoted E1, and other embodiments are denoted E1.1, E1.2, E1.3, E2, etc.

E1. A compound of formula (I):

(I)

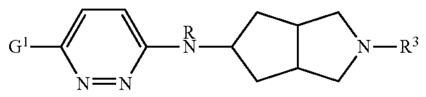

or a pharmaceutically acceptable salt thereof, wherein:

$G^1$ is

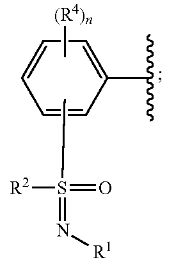

R is hydrogen, $C_{1-4}$alkyl, $C_3$ cycloalkyl, or —$C_{1-3}$alkylene-$C_{3-4}$cycloalkyl;

$R^1$ is hydrogen, $C_{1-4}$alkyl, $C_{1-2}$fluoroalkyl, $C_{3-4}$cycloalkyl, —$C_{1-3}$alkylene-$C_{3-4}$cycloalkyl, or —C(O)$C_{1-4}$alkyl;

$R^2$ is $C_{1-4}$alkyl, $C_{1-2}$fluoroalkyl, $C_{3-4}$cycloalkyl, or —$C_{1-3}$alkylene-$C_{3-4}$cycloalkyl;

$R^3$ is -$L^1$-$G^2$, $G^2$, -$L^2$-$G^2$, -$L^2$-$L^1$-$G^2$, —$C_{2-6}$alkylene-$R^{3a}$, $C_{3-7}$alkyl, or $C_{3-7}$haloalkyl;

$R^4$, at each occurrence, is independently halogen, cyano, $C_{1-4}$alkyl, $C_{1-2}$fluoroalkyl, OH, —$OC_1$. 4alkyl, or —$OC_{1-2}$fluoroalkyl;

n is 0, 1,2, 3, or 4;

$L^1$ is $C_{1-5}$alkylene;

$L^2$ is 1,1-cyclopropylene;

$G^2$ is a 4- to 12-membered heterocyclyl, a 6- to 12-membered aryl, a 5- to 12-membered heteroaryl, or a $C_{3-12}$carbocyclyl optionally fused to a 6-membered arene, wherein $G^2$ is optionally substituted with 1-5 substituents independently selected from the group consisting of halogen, cyano, oxo, $C_{1-4}$alkyl, $C_{1-4}$haloalkyl, —$OR^{13}$, —$N(R^1)_2$, —$C_{1-3}$alkylene-$OR^{13}$, and —$C_{1-3}$alkylene-$N(R^{14})_2$; $R^{3a}$ is —$OR^{14}$ or —$N(R^{14})_2$;

$R^{13}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{13}$, together with a nitrogen to which the two $R^{13}$ attach form a 4- to 6-membered heterocyclic ring optionally substituted with 1-4 substituents independently selected from the group consisting of halogen and $C_{1-4}$alkyl;

$R^{14}$, at each occurrence, is independently hydrogen, $C_{1-4}$alkyl, $C_{1-4}$haloalkyl, $G^3$, or —$C_{1-3}$alkylene-$G^3$, wherein alternatively two $R^{14}$, together with a nitrogen to which the two $R^4$ attach form a 4- to 6-membered heterocyclic ring optionally substituted with 1-4 substituents independently selected from the group consisting of halogen and $C_{1-4}$alkyl;

$G^3$ is phenyl, a monocyclic 5- to 6-membered heteroaryl, a monocyclic 4- to 8-membered heterocyclyl, or a monocyclic $C_{3-8}$cycloalkyl, wherein $G^3$ is optionally substituted with 1-5 substituents independently selected from the group consisting of halogen, cyano, $C_{1-4}$alkyl, $C_{1-4}$haloalkyl, oxo, —$OR^{15}$, and —$N(R^{15})_2$; and $R^{15}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{15}$, together with a nitrogen to which the two $R^{15}$ attach form a 4- to 6-membered heterocyclic ring optionally substituted with 1-4 substituents independently selected from the group consisting of halogen and $C_{1-4}$alkyl.

E1.1. The compound of E1 having formula (I-A)

(I-A)

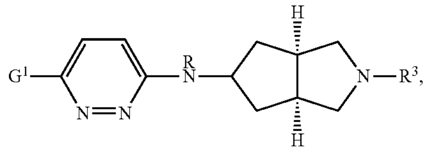

or a pharmaceutically acceptable salt thereof.

E1.2. The compound of E1.1 having formula (I-A1)

(I-A1)

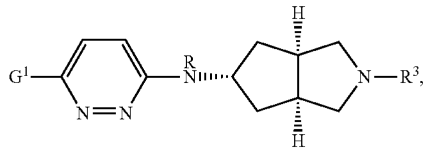

or a pharmaceutically acceptable salt thereof.

E1-3. The compound of E1.1 having formula (I-A2)

(I-A2)

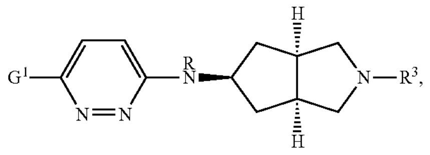

or a pharmaceutically acceptable salt thereof.

E2. The compound of any of E1-E1.3, or a pharmaceutically acceptable salt thereof wherein $G^1$ is

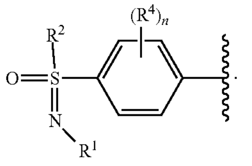

E2.1. The compound of E2, or a pharmaceutically acceptable salt thereof, wherein $G^1$ is N

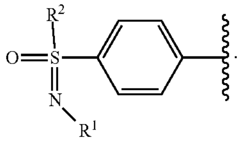

E2.2. The compound of E2, or a pharmaceutically acceptable salt thereof, wherein $G^1$ is

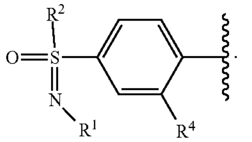

E2.3. The compound of E2, or a pharmaceutically acceptable salt thereof, wherein $G^1$ is

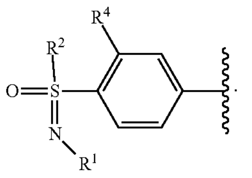

E2.4. The compound of E2, or a pharmaceutically acceptable salt thereof, wherein $G^1$ is

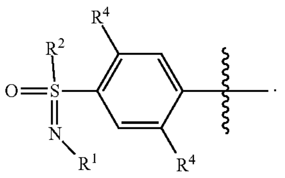

E3. The compound of any of E1-E2.4, or a pharmaceutically acceptable salt thereof, wherein $R^1$ is hydrogen.

E4. The compound of any of E1-E2.4, or a pharmaceutically acceptable salt thereof, wherein $R^1$ is $C_{1-4}$alkyl.

E4.1. The compound of E4, or a pharmaceutically acceptable salt thereof, wherein $R^1$ is $CH_3$.

E4.2. The compound of E4.1, or a pharmaceutically acceptable salt thereof, wherein the $CH_3$ at $R^1$ is $CD_3$.

E5. The compound of any of E1-E2.4, or a pharmaceutically acceptable salt thereof, wherein $R^1$ is $C_{1-2}$fluoroalkyl.

E5.1. The compound of E5, or a pharmaceutically acceptable salt thereof, wherein $R^1$ is $CF_3$.

E6. The compound of any of E1-E2.4, or a pharmaceutically acceptable salt thereof, wherein $R^1$ is —C(O)$C_{1-4}$alkyl.

E6.1. The compound of E6, or a pharmaceutically acceptable salt thereof, wherein $R^1$ is C(O)$CH_3$.

E7. The compound of any of E1-E6.1, or a pharmaceutically acceptable salt thereof, wherein $R^2$ is $C_{1-4}$alkyl.

E7.1. The compound of E7, or a pharmaceutically acceptable salt thereof, wherein $R^2$ is $CH_3$.

E8. The compound of any of E1-E7.1, or a pharmaceutically acceptable salt thereof, wherein $R^4$, at each occurrence, is independently halogen or $C_{1-2}$fluoroalkyl.

E8.1. The compound of any of E1-E8, or a pharmaceutically acceptable salt thereof, wherein $R^4$, at each occurrence, is independently halogen.

E8.2. The compound of any of E1-E8, or a pharmaceutically acceptable salt thereof, wherein $R^4$, at each occurrence, is independently $C_{1-2}$fluoroalkyl.

E9. The compound of E8, or a pharmaceutically acceptable salt thereof, wherein $R^4$, at each occurrence, is independently fluoro or $CF_3$.

E9.1. The compound of E8.1 or E9, or a pharmaceutically acceptable salt thereof, wherein $R^4$, at each occurrence, is independently fluoro.

E9.2. The compound of E8.2 or E9, or a pharmaceutically acceptable salt thereof, wherein $R^4$, at each occurrence, is independently $CF_3$.

E10. The compound of any of E1-E9.2, or a pharmaceutically acceptable salt thereof, wherein n is 0, 1, or 2.

E10.1. The compound of E10, or a pharmaceutically acceptable salt thereof, wherein n is 0.

E10.2. The compound of E10, or a pharmaceutically acceptable salt thereof, wherein n is 1.

E10.3. The compound of E10, or a pharmaceutically acceptable salt thereof, wherein n is 2.

E11. The compound of any of E1-E10.3, or a pharmaceutically acceptable salt thereof, wherein $R^3$ is $-L^1-G^2$.

E12. The compound of any of E1-E11, or a pharmaceutically acceptable salt thereof, wherein $G^3$ is the optionally substituted 4- to 12-membered heterocyclyl.

E12.1. The compound of E12, or a pharmaceutically acceptable salt thereof, wherein the ring system of the optionally substituted 4- to 12-membered heterocyclyl at $G^2$ is a 4- to 8-membered monocyclic heterocyclyl ring system, a 6- to 10-membered bridged bicyclic heterocyclyl ring system, a 7- to 12-membered fused bicyclic heterocyclyl ring system, or a 7- to 12-membered spiro heterocyclyl ring system.

E13. The compound of any of E1-E12.1, or a pharmaceutically acceptable salt thereof, wherein the ring system of the optionally substituted 4- to 12-membered heterocyclyl at $G^2$ is a 4- to 8-membered monocyclic heterocyclyl ring system.

E13.1. The compound of any of E12-E13, or a pharmaceutically acceptable salt thereof, wherein the heterocyclyl ring system at $G^2$ contains 1-2 heteroatoms independently selected from O, N, and S.

E13.2. The compound of E13.1, or a pharmaceutically acceptable salt thereof, wherein the heterocyclyl ring system at $G^2$ contains 1-2 ring oxygen atoms.

E14. The compound of any of E13-E13.2, or a pharmaceutically acceptable salt thereof, wherein the ring system of the optionally substituted 4- to 12-membered heterocyclyl at $G^2$ is tetrahydropyranyl.

E15. The compound of E14, or a pharmaceutically acceptable salt thereof, wherein the ring system of the optionally substituted 4- to 12-membered heterocyclyl at $G^2$ is tetrahydropyran-4-yl.

E16. The compound of any of E12-E15, or a pharmaceutically acceptable salt thereof, wherein $G^2$ is optionally substituted with 1-4 substituents independently selected from the group consisting of halogen, hydroxy, oxo, $C_{1-4}$alkyl, and —O$C_{1-4}$alkyl.

E17. The compound of any of E1-E16, or a pharmaceutically acceptable salt thereof, wherein $G^2$ is

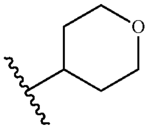

or

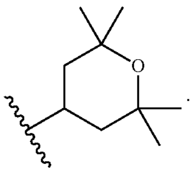

E18. The compound of any of E1-E11, or a pharmaceutically acceptable salt thereof, wherein $G^2$ is the optionally substituted 5- to 12-membered heteroaryl.

E19. The compound of any of E1-E11 or E18, or a pharmaceutically acceptable salt thereof, wherein the ring system of the optionally substituted 5- to 12-membered heteroaryl at $G^2$ is a 6-membered monocyclic heteroaryl.

E20. The compound of E19, or a pharmaceutically acceptable salt thereof, wherein the ring system of the optionally substituted 5- to 12-membered heteroaryl at $G^2$ is pyridinyl.

E21. The compound of E20, or a pharmaceutically acceptable salt thereof, wherein the ring system of the optionally substituted 5- to 12-membered heteroaryl at $G^2$ is pyridin-2-yl.

E22. The compound of any of E1-E11 or E18-E21, wherein $G^2$ is

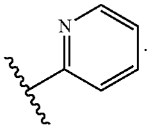 [SMILES: *c1ccccn1]

E23. The compound of any of E1-E11, or a pharmaceutically acceptable salt thereof, wherein $G^2$ is the optionally substituted $C_{3-12}$carbocyclyl optionally fused to a 6-membered arene.

E24. The compound of any of E1-E11 or E23, or a pharmaceutically acceptable salt thereof, wherein the ring system of the optionally substituted $C_{3-12}$carbocyclyl optionally fused to a 6-membered arene is a monocyclic $C_{3-8}$cycloalkyl.

E25. The compound of any of E1-E11 or E23-E24, or a pharmaceutically acceptable salt thereof, wherein $G^2$ is

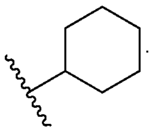.

E26. The compound of any of E1-E11, or a pharmaceutically acceptable salt thereof, wherein $G^2$ is the optionally substituted 6- to 12-membered aryl.

E27. The compound of any of E1-E26, or a pharmaceutically acceptable salt thereof, wherein $L^1$ is the $C_{1-5}$alkylene.

E28. The compound of any of E1-E27, or a pharmaceutically acceptable salt thereof, wherein $L^1$ is $CH_2$.

E29. The compound of E28, or a pharmaceutically acceptable salt thereof, wherein the $CH_2$ at $L^1$ is $CD_2$.

E30. The compound of any of E1-E27, or a pharmaceutically acceptable salt thereof, wherein $L^1$ is $CH_2CH_2$.

E31. The compound of any of E1-E30, or a pharmaceutically acceptable salt thereof, wherein R is hydrogen.

E32. The compound of E1 selected from the group consisting of (2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone;

imino(methyl)(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)-$\lambda^6$-sulfanone;

(2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)((methyl-$d_3$)imino)-$\lambda^6$-sulfanone;

N-((2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)(oxo)-$\lambda^6$-sulfaneylidene)acetamide;

(3-fluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone;

(2-fluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-λ6-sulfanone;

(2,5-difluoro-4-(6-(((3aR,5s,6aS)-2-((tetrahydro-2H-pyran-4-yl)methyl)octahydrocyclopenta[c]pyrrol-5-yl)amino)pyridazin-3-yl)phenyl)(imino)methyl)-$\lambda^6$-sulfanone;

(2,5-difluoro-4-(6-(((3aR,5s,6aS)-2-(pyridin-2-ylmethy)octahydrocyclopenta[c]pyrrol-5-yl)amino)pyridazin-3-yl)phenyl)(imino)(methyl)-$\lambda^6$-sulfanone; (2,5-difluoro-4-(6-(((3aR,5s,6aS)-2-(2-(tetrahydro-2H-pyran-4-yl)ethyl)octahydrocyclopenta[c]pyrrol-5-yl)amino)pyridazin-3-yl)phenyl)(imino)(methyl)-$\lambda^6$-sulfanone;

(4-(6-(((3aR,5s,6aS)-2-(cyclohexylmethyl)octahydrocyclopenta[c]pyrrol-5-yl)amino)pyridazin-3-yl)-2,5-difluorophenyl(imino)(methyl)-$\lambda^6$-sulfanone;

(2,5-difluoro-4-(6-(((3aR,5s,6aS)-2-((2,2,6,6-tetramethyl-tetrahydro-2H-pyran-4-yl)methyl-$d_2$)octahydrocyclopenta[c]pyrrol-5-yl)amino)pyridazin-3-yl)phenyl)(imino)(methyl-)$\lambda_6$-sulfanone;

methyl(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)((trifluoromethyl)imino)-$\lambda^6$-sulfanone;

imino(methyl)(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)-2-(trifluoromethyl)phenyl)-$\lambda^6$-sulfanone;

or a pharmaceutically acceptable salt thereof.

E33. The compound of any of E1-E32, or a pharmaceutically acceptable salt thereof, wherein the compound is isotopically labeled.

E34. A pharmaceutical composition comprising the compound of any of E1-E33, or a pharmaceutically acceptable salt thereof, and a pharmaceutically acceptable carrier.

E35. A method for antagonizing mAChR $M_4$ in a subject, comprising administering to the subject a therapeutically effective amount of the compound of any of E1-E33, or a pharmaceutically acceptable salt thereof, or the pharmaceutical composition of E34.

E36. A method for treating a disorder in a subject, wherein the subject would benefit from antagonism of mAChR $M_4$, comprising administering to the mammal a therapeutically effective amount of the compound of any of E1-E33, or a pharmaceutically acceptable salt thereof, or the pharmaceutical composition of E34.

E37. The method of E36, wherein the disorder is a neurodegenerative disorder, a movement disorder, or a brain disorder.

E38. The method of E37, wherein the disorder is a movement disorder.

E39. The method of E37, wherein the disorder is selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

E40. A method for treating motor symptoms in a subject, comprising administering to a subject in need thereof a therapeutically effective amount of the compound of any of E1-E33, or a pharmaceutically acceptable salt thereof, or the pharmaceutical composition of E34.

E41. The method of E40, wherein the subject has a disorder selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

E42. A compound of any of E1-E33, or a pharmaceutically acceptable salt thereof, or the pharmaceutical composition of E34, for use in the treatment of a neurodegenerative disorder, a movement disorder, or a brain disorder.

E43. The use of a compound of any of E1-E33, or a pharmaceutically acceptable salt thereof, or the pharmaceutical composition of E34, for the preparation of a medicament for the treatment of a neurodegenerative disorder, a movement disorder, or a brain disorder.

Throughout the embodiments and description of the compounds of the invention, all instances of haloalkyl may be fluoroalkyl (e.g., any $C_{1-4}$haloalkyl may be $C_{1-4}$fluoroalkyl).

Compound names and/or structures can be assigned/determined by using the Struct=Name naming algorithm as part of CHEMDRAW® ULTRA.

The compound may exist as a stereoisomer wherein asymmetric or chiral centers are present. The stereoisomer is "?" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical *Organic Chemistry,"* 5th edition (1989), Longman Scientific & Technical, Essex CM20 2JE, England, or (2) direct separation of the mixture of optical enantiomers on chiral chromatographic columns, or (3) fractional recrystallization methods.

Compounds have a 3,3a,4,5,6,6a-hexahydro-1H-cyclopenta[c]pyrrole core structure that has a plane of symmetry as in the following two representative structures.

A

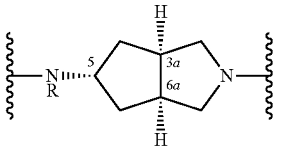

trans
(3aR,5s,6aS)

B

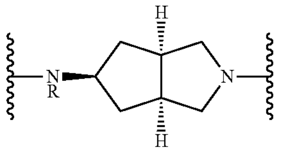

cis
(3aR,5r,6aS)

These structures are considered meso since A and B are superimposable with their respective mirror images. The 3a, 5, and 6a stereochemical designations are used herein for symmetrical structures of type A and B to designate relative stereochemistry between the ring fusion and the 5-position. Thus, when drawn in the orientation depicted above 3aR, 5s,6aS refers to trans relative stereochemistry between the 5-position substituent and the ring fusion, and 3aR,5r,6aS refers to cis relative stereochemistry between the 5-position substituent and the ring fusion. The lower case s and r designations at the 5-position refer to pseudo asymmetry as described by G. P. Moss in "Basic terminology of stereochemistry (IUPAC Recommendations)" in *Pure and Applied Chemistry* (1996), 68 (12) 2193-2222. The person skilled in the art will understand that when structures A and B are drawn as the respective mirror images, chemical naming programs may, depending on the program, reverse the stereochemical designation for 3a and 6 positions from R to S and S to R, respectively, but that the pseudo asymmetry at the 5-position remains invariant, due to R having priority over S according to priority rules and the reversal of the carbons having R and S designations. Compounds of formula (I) or any of its subformulas may have a 5-position substituent in a trans configuration or a cis configuration, or may be prepared as a mixture of trans and cis.

It should be understood that the compound may possess tautomeric forms, as well as geometric isomers, and that these also constitute embodiments of the disclosure.

In the compounds of formula (I), and any subformulas, any "hydrogen" or "H," whether explicitly recited or implicit in the structure, encompasses hydrogen isotopes $^{1}H$ (protium) and $^{2}H$ (deuterium).

The present disclosure also includes isotopically-labeled compounds (e.g., deuterium labeled), where an atom in the isotopically-labeled compound is specified as a particular isotope of the atom. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$.

Isotopically-enriched forms of compounds of formula (I), or any subformulas, may generally be prepared by conventional techniques known to those skilled in the art or by processes analogous to those described in the accompanying Examples using an appropriate isotopically-enriched reagent in place of a non-isotopically-enriched reagent. The extent of isotopic enrichment can be characterized as a percent incorporation of a particular isotope at an isotopically-labeled atom (e.g., % deuterium incorporation at a deuterium label).

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) or any of its subformulas may be prepared by synthetic processes or by metabolic processes. Preparation of the compounds by metabolic processes includes those occurring in the human or animal body (in vivo) or processes occurring in vitro.

Abbreviations: AcOH is acetic acid; BMS is borane dimethyl sulfide complex; Boc is tert-butyloxycarbonyl; BrettPhos-Pd-G3 is [(2-di-cyclohexylphosphino-3,6-dimethoxy-2',4',6'-triisopropyl-1,1'-biphenyl)-2-(2'-amino-1,1'-biphenyl)]palladium(II) methanesulfonate (CAS Number 1470372-59-8); t-BuXPhos is 2-di-tert-butylphosphino-2',4',6'-triisopropylbiphenyl; DAST is diethylaminosulfur trifluoride; DCE is 1,2-dichloroethane; DCM is dichloromethane; DIAD is diispropylazodicarboxylate; DIBAL is diisobutylaluminum hydride; DIEA and DIPEA both refer to N,N-diisopropylethylamine; DMF is N,N-dimethylformamide; $Et_3SiCl$ is chlorotriethylsilane; HATU is 2-(7-aza-1H-benzotriazole-1-yl)-1,1,3,3-tetramethyluronium hexafluorophosphate; $LiAlH(OtBu)_3$ is lithium tri-tert-butoxyaluminum hydride; m-CPBA is meta-chloroperoxybenzoic acid; MeOH is methanol; MsCl is methanesulfonyl chloride; $NaBH(OAc)_3$ and STAB both refer to sodium triacetoxyborohydride; rt or r.t. is room temperature; NMP is N-methyl-2-pyrrolidone; $Pd(dppf)Cl_2$ is [1,1'-Bis(diphenylphosphino)ferrocene]dichloropalladium(II); $Pd_2(dba)_3$ is tris(dibenzylideneacetone)dipalladium(0); $PPh_3$ is triphenylphosphine; RuPhos-Pd-G3 is (2-dicyclohexylphosphino-2',6'-diisopropoxy-1,1'-biphenyl)[2-(2'-amino-1,1'-biphenyl)]palladium(II) methanesulfonate (CAS Number 1445085-77-7); Selectfluor™ is 1-chloromethyl-4-fluoro-1,4-diazoniabicyclo[2.2.2]octane bis(tetrafluoroborate); t-BuOH is tert-butyl alcohol; t-BuOK is potassium tert-butoxide; TBAI is tetrabutylammonium iodide; THF is tetrahydrofuran; and TosMIC is toluenesulfonylmethyl isocyanide.

Compounds of formula (I) or any of its subformulas may be synthesized as shown in the following schemes.

Scheme 1

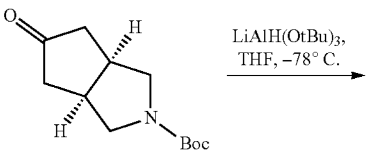

A

-continued

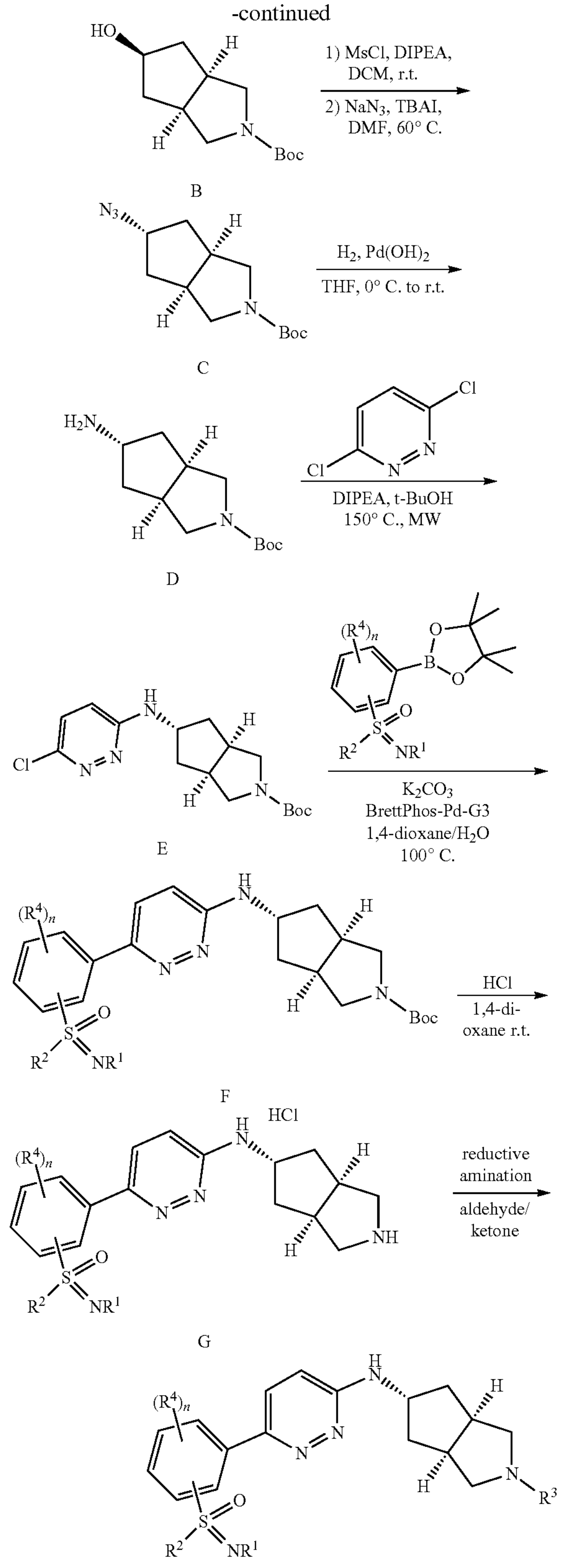

B

C

D

E

F

G

H

As shown in Scheme 1, cis-tert-butyl 5-oxohexahydrocyclopenta[c]pyrrole-2(1H)-carboxylate (compound A; CAS #146231-54-1, Synthonix, Catalog #B8253) can be reduced (e.g., lithium tri-t-butoxy aluminum hydride) to form compound B, which can then be converted to the corresponding azide compound C. Reduction to the amine provides compound D, which can be reacted with 3,6-dichloropyridazine to generate compound E. Coupling with a suitable boronic acid or ester provides compound F, which may be deprotected (e.g., with hydrochloric acid) to generate compound G. Compound G may be reacted with suitable aldehydes or ketones corresponding to $R^1$ by reductive amination to provide H, wherein $R^3$ is $G^{2'}$, $-L^1-G^2$, $—C_{2-6}$alkylene-$R^{3a}$, or $C_{3-7}$-alkyl and $G^{2'}$ is the carbocyclyl or heterocyclyl of $G^2$.

Compound A may also be reduced with sodium borodeuteride to introduce a deuterium into B at the point of attachment of the hydroxyl group.

Scheme 2

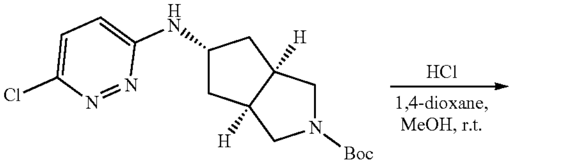

E

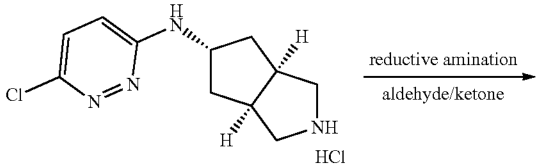

I

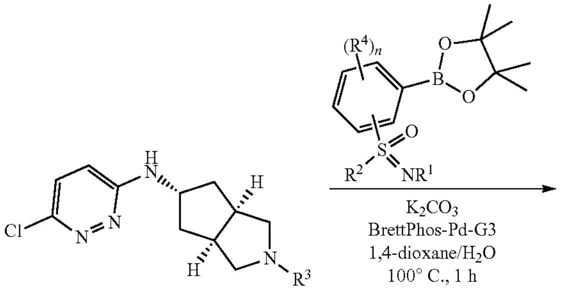

J

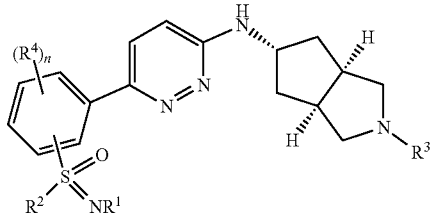

H

Scheme 2 illustrates an alternate synthesis route to compounds of formula H, wherein the reductive amination and boronic acid coupling steps are reversed. Deprotection of compound E under acid conditions provides compound I, which may be reacted with suitable aldehydes or ketones corresponding to $R^3$ by reductive amination to provide compounds J, wherein $R^3$ is $G^2$, $-L^1-G^2$, $—C_{2-6}$alkylene-$R^{3a}$, or $C_{3-7}$alkyl. In turn, reaction of compounds J with suitable boronic acids or esters may provide compounds H. Intermediate J may also be prepared using the alkylation process of Scheme 4.

Scheme 3

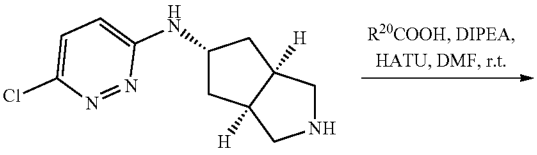

I

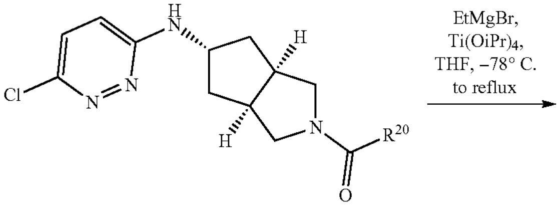

M

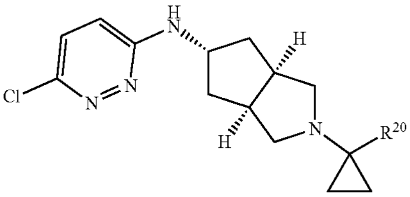

N

As shown in Scheme 3, reaction of compound I with a carboxylic acid $R^{20}CO_2H$ under standard amide bond forming conditions may provide amides M. Suitable reaction conditions include reacting I (1 equiv.) with the carboxylic acid (1.2 equiv.) in the presence of DIPEA (3 equiv.) and HATU (1.5 equiv.) in DME at room temperature. Amides M may react with a titanacyclopropane generated in situ from an ethyl Grignard and $Ti(OiPr)_4$ (Kulinkovich-de Meijere reaction) to provide cyclopropyl compounds of formula N. Suitable reaction conditions include reacting a solution of ethylmagnesium bromide (5 equiv., 1.0 M solution) in THF with titanium(IV) isopropoxide (2.1 equiv.) at −78° C. for 30 min under an inert atmosphere, and adding compound M (1 equiv. in THF), followed by warming to r.t. and then stirring at reflux for 1 h. Compounds N may be processed according to the Suzuki coupling method outlined in Scheme 2 to provide additional compounds of the invention. In Scheme 3, $R^{20}$ is $G^2$, $-L^1-G^2$, an alkyl group (e.g., $C_{1-4}$alkyl), $—C_{1-3}$alkylene-$OR^{13}$, or $—C_{1-3}$alkylene-$N(R^{13})_2$, wherein $G^2$, $L^1$, and $R^{13}$ are as defined herein.

Scheme 4

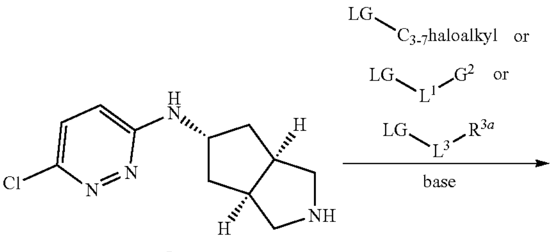

I

-continued

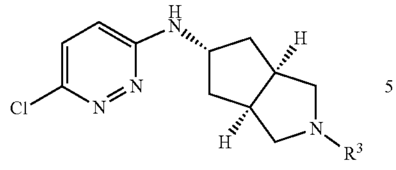

J

As shown in Scheme 4, compounds of formula I may be alkylated using standard secondary amine alkylation conditions to provide tertiary amines J, wherein $R^3$ is $-L^1-G^2$, $—C_{2-6}$ alkylene-$R^{3a}$, or $C_{3-7}$haloalkyl; $L^3$ is a $C_2$<alkylene group; LG is a leaving group (e.g., Cl, Br, I, mesylate, tosylate, triflate); and $R^{3a}$, $L^1$, and $G^2$ are as defined herein. An exemplary set of conditions for alkylation is to heat the reactants to about 70° C. in a solvent such as DMF or DMSO in the presence of a base such as $Cs_2CO_3$. Another exemplary set of alkylation conditions is to heat the reactants to about >100° C. in a sealed vessel in a microwave reactor using a solvent such as acetonitrile, DMF or DMSO in the presence of a tertiary amine base such as DIPEA.

Scheme 5

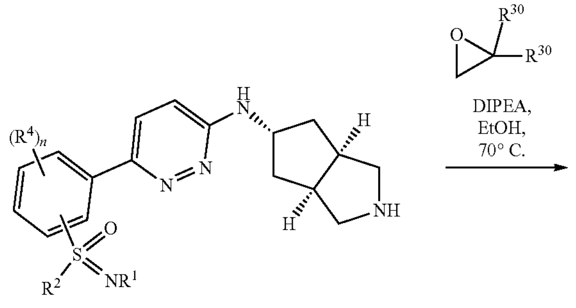

G

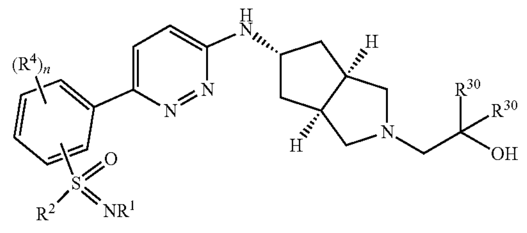

P

As shown in Scheme 5, secondary amine compounds G may be reacted with epoxides under basic conditions to provide hydroxy compounds P, wherein $R^{30}$ are alkyl groups, together having 2-4 carbons, or two $R^{30}$, together with the carbon to which they attach form the carbocyclyl or heterocyclyl of $G^2$ (e.g., tetrahydropyranyl, cyclohexyl).

Scheme 6

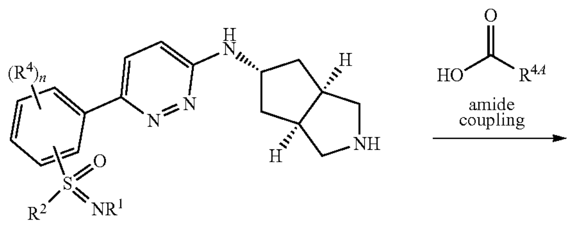

G

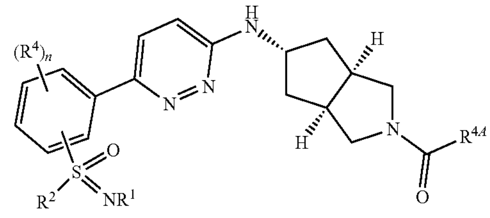

R

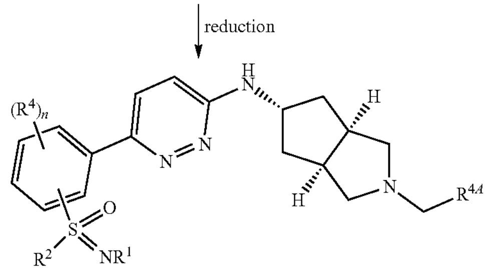

S

As shown in Scheme 6, compounds G may be reacted with an appropriate carboxylic acid to form amide compound R, which may be reduced to generate compound S, wherein $R^{4A}$ is $G^2$, $—C_{1-2}$alkylene-$G^2$, $—C_{1-5}$alkylene-$R^{3a}$, or $C_{2-6}$alkyl, wherein $G^2$ and $R^{3a}$ are as defined herein. Amide coupling conditions are well known in the art and include treating the reactants with a coupling agent such as HATU, in the presence of a base (e.g., DIPEA) in a solvent such as DMF or DCM. Amide reduction conditions are well known in the art and include treating the amide substrate with a reducing agent like DIBAL in DCM or $LiAlH_4$ in THF. The reaction may be conducted anywhere from −78° C. to room temperature. Compound R may also be reacted with $LiAlD_4$ to introduce deuterium atoms in place of the carbonyl.

The amide coupling process of Scheme 6 may be used for a compound where the phenyl sulfoximine substituent is replaced by chloro (compound I). The chloro-substituted intermediate may also be subjected to a Suzuki reaction prior to carbonyl reduction. Suitable Suzuki reaction conditions include those generally outlined in Schemes 1 and 2 and as described in the Examples herein.

Scheme 7

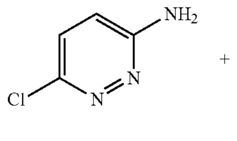

-continued

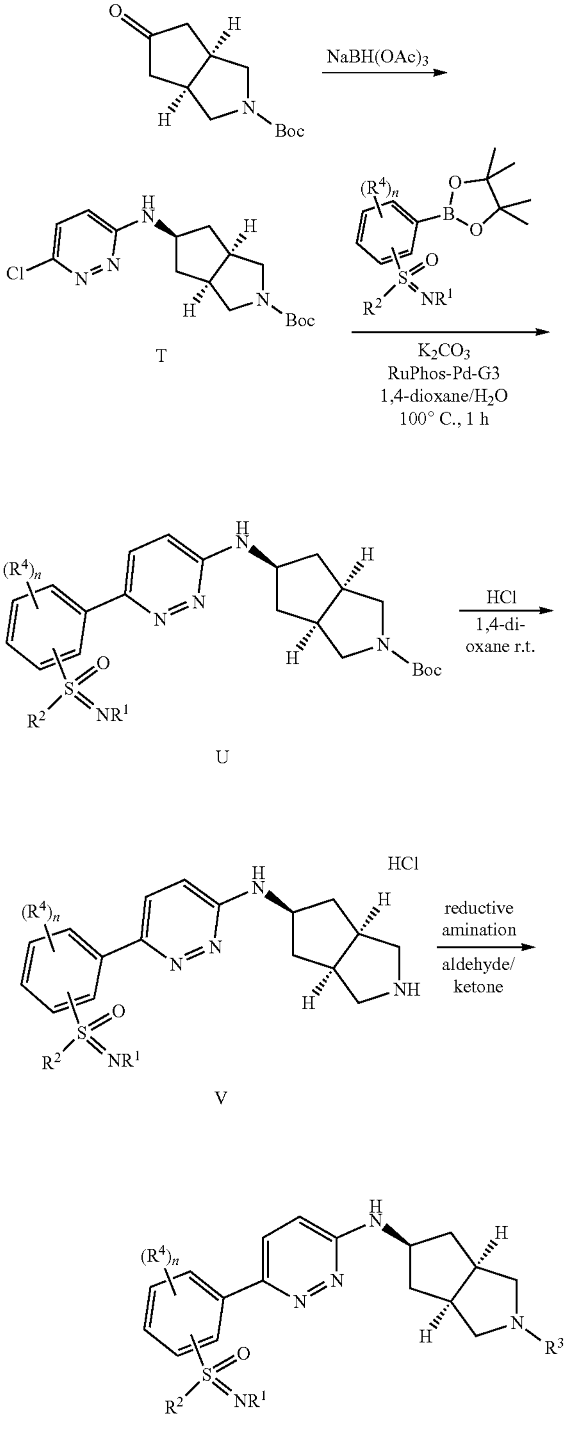

T U V W

As shown in Scheme 7, 3-amino-6-chloropyridazine can be reacted with cis-N-Boc-5-oxo-octahydrocyclopenta[c]pyrrole to generate compound T, which may be coupled with an appropriate boronic acid or ester to form compound U. Deprotection (e.g., with hydrochloric acid) generates compounds V, and reaction with a suitable aldehyde or ketone generates compound W, wherein $R^3$ is $G^{2'}$ (as defined above), $-L^1-G^2$, $—C_{2-6}$alkylene-$R^{3a}$, or $C_{3-7}$alkyl, wherein $L^1$, $G^2$, and $R^{3a}$ are as defined herein.

Scheme 8

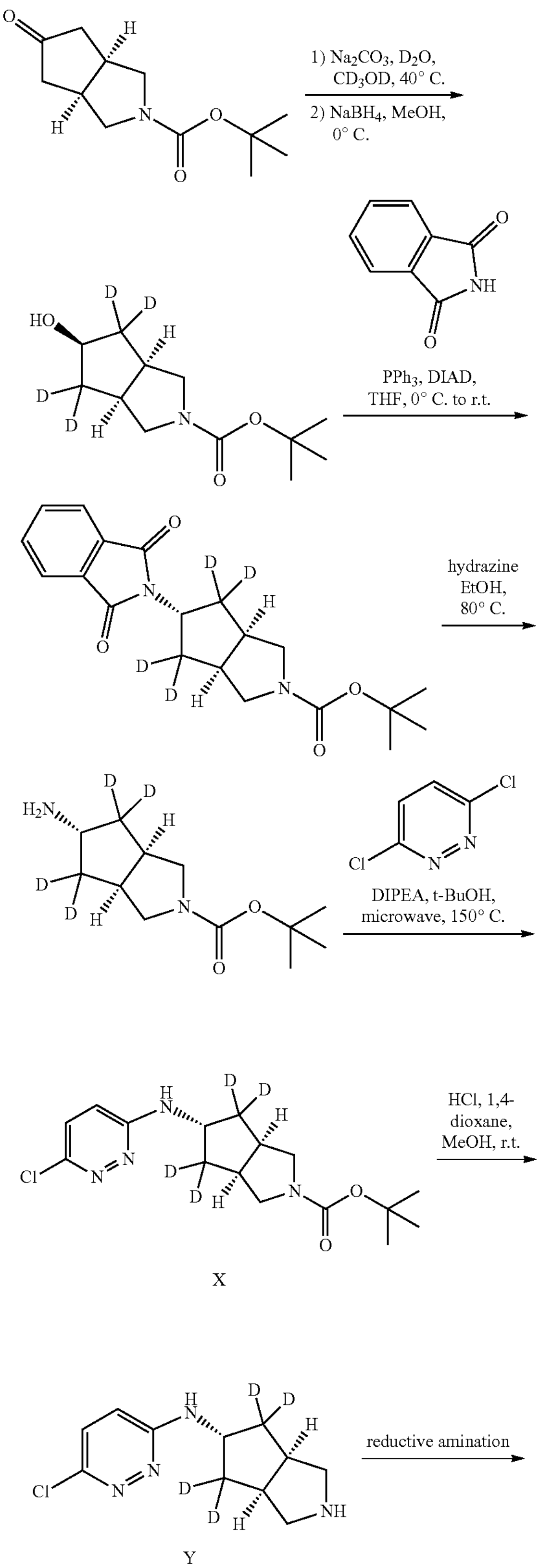

X Y

-continued

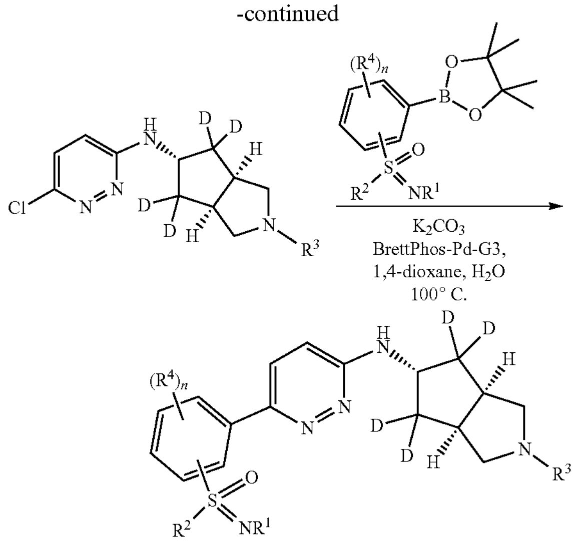

Z

Scheme 8 shows a process to prepare intermediates X and Y and the conversion of Y to Z by reductive amination, followed by a Suzuki coupling. Reductive amination of Y may involve reaction with a suitable aldehyde or ketone, wherein $R^3$ is $G^{2'}$ (as defined above), $-L^1-G^2$, $—C_{2-6}$alkylene-$R^{3a}$, or $C_{3-7}$alkyl, wherein $L^1$, $G^2$, and $R^{3a}$ are as defined herein. Alternatively, the intermediate X may be processed according to Scheme 1 to arrive at final compounds Z. Compounds X may also be processed according to Schemes 1 and 3-6 to arrive at additional compounds of the invention.

Reductive amination conditions suitable for use in the processes of Schemes 1-2 and 7-8 are well known in the art. Representative reaction conditions for aldehyde reductive amination include treating the reactants with $NaBH(OAc)_3$ in solvents such as DCM, THF, and MeOH, and mixtures thereof, optionally in the presence of a base (e.g., DIPEA). Aldehyde reductive amination may also be effected by treatment with $NaBH_3CN$ in EtOH with heating (e.g., to about 80° C.). Ketone reductive amination may be facilitated by addition of an acid like acetic acid to the solvent mixture (e.g., DCM-THF) and heating to 40° C. for about an hour. A representative solvent ratio of DCM:THF:AcOH is (3:3:0.5). Ketone reductive amination may also be effected by treatment with $Ti(OiPr)_4$ and $NaBH_3CN$ or $NaBH_4$ in EtOH from room temperature to about 80° C. $NaBD_3CN$ may be used instead of $NaBH_3CN$ to incorporate deuterium and provide compounds enriched in deuterium over protium.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical *Organic Chemistry,*" 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity $M_4$ is the most highly expressed mAChR subtype in the striatum and its expression is similar in rodents and primates. Due to a lack of selective $M_4$ antagonists, mechanistic understanding of the role of $M_4$ has been guided by biochemical and genetic studies, as well as the use of highly selective $M_4$ positive allosteric modulators (PAMs). Highly selective $M_4$PAMs induce robust decreases in behavioral responses to psychomotor stimulants that act by increasing striatal DA levels. Furthermore, genetic deletion of $M_4$ increases exploratory locomotor activity, potentiates locomotor responses to amphetamine and other stimulants, and eliminates effects of $M_4$ PAMs on locomotor activity and these effects are also observed with selective deletion of $M_4$ from striatal spiny projection neurons that express the D1 subtype of DA receptor (D1-SPNs). In vivo microdialysis studies reveal that administration of $M_4$ PAMs reduces amphetamine-induced DA release in the dorsal and ventral striatum and fMRI studies show that $M_4$PAMs reverse amphetamine-induced increases in cerebral blood flow (CBV) in striatum and other basal ganglia nuclei. More recently, fast-scanning cyclic voltammetry (FSCV) and genetic studies, demonstrated that $M_4$ PAMs act, at least in part, by inhibition of DA release from presynaptic DA terminals in the striatum through release of an endocannabinoid from striatal spiny projection neurons (SPNs) and activation of CB2 cannabinoid receptors on DA terminals.

$M_4$ is heavily expressed in a subset of SPNs that also express the $D_1$ subtype of DA receptor ($D_1$DR), which form the direct pathway (D1-SPNs) sending inhibitory projections to the substantia nigra pars *reticulata* (SNr). Interestingly, $D_1$DRs activate a unique GTP-binding protein in $D_1$-SPNs, termed $G_{\alpha olf}$ that couples $D_1$Rs to activation of adenylyl cyclase, formation of cAMP, and activation of protein kinase A (PKA). This signaling pathway is critical for many of the behavioral actions of DA-mediated activation of motor activity Interestingly, M couples to $G\alpha_{i/o}$ G proteins, which inhibit adenylyl cyclase and have the potential to directly counteract inhibit $D_1$ receptor signaling and effects on motor function. These studies raise the possibility that, in addition to inhibition of DA release, $M_4$ PAMs may directly inhibit D1R-mediated signaling in $D_1$-SPNs by direct inhibition of cAMP formation and this could also contribute to the powerful inhibitory effect of selective $M_4$ activation of DA signaling in the basal ganglia. Consistent with this, $M_4$ PAMs inhibit locomotor-stimulating effects of a direct acting $D_1$ agonist. Furthermore, a series of pharmacological, genetic, and molecular/cellular studies reveal that this response is mediated by inhibition of $D_1$DR signaling in D1-SPNs. Thus, the primary action of $M_4$ PAMs on $D_1$DR signaling is not in the striatum, but on GABAergic terminals of $D_1$-SPNs in the SNr, where activation of $D_1$DRs induces a robust increase in GABA release. This challenges the widespread view that cholinergic regulation of striatal function is almost exclusively mediated through ACh released from tonically active, striatal cholinergic interneurons (ChIs) and raises the possibility that cholinergic innervation of the SNr from cholinergic projections from the pedunculopontine nucleus may also play a critical role in regulating motor activity and other functions of the basal ganglia direct pathway. Together, these data suggest that in addition to inhibiting DA release, $M_4$ activation also acts postsynaptically in $D_1$-expressing SPNs to inhibit motor function.

Consistent with a prominent role of $M_4$ as the primary mAChR subtype involved in regulating motor function, multiple reports indicate that the locomotor-activating effects of the mAChR antagonist scopolamine are dramatically reduced in $M_4$ knockout mice, but not the other four mAChR subtypes ($M_{1-3,5}$). Furthermore, haloperidol-induced catalepsy, a model of parkinsonian motor disability, is reduced in $M_4$ knockout mice as compared to wild-type controls. Evaluation of the anti-parkinsonian effects of scopolamine, by assessing effects of this compound on catalepsy induced by the DA receptor antagonist haloperidol, display robust catalepsy that was completely reversed by scopolamine in WT mice. The reversal by scopolamine was uncommonly robust and more pronounced than we observe with agents targeting a number of other targets being evaluated for potential antiparkinsonian effects, including metabotropic glutamate (mGlu) receptors $mGlu_4$ or $mGlu_5$, $A_2A$ adenosine receptors, and NMDA receptors. Importantly, scopolamine was ineffective in reducing catalepsy in $M_4$KO mice, suggesting that the anti-cataleptic effect of scopolamine requires actions on mAChR $M_4$. Taken together with the extensive studies of $M_4$ modulation of basal ganglia and motor function, these studies provide compelling evidence that $M_4$ is the dominant mAChR subtype involved in the antiparkinsonian effects of non-selective mAChR antagonists and provide support for discovery and development of selective $M_4$ antagonists for treatment of neurodegenerative disease such as PD, dystonia, tardive dyskinesia and other movement disorders.

Despite advances in mAChR research, there is still a scarcity of compounds that are potent, efficacious and selective antagonists of the $M_4$ mAChR. Highly selective $M_4$ antagonists represent a new therapeutic approach for the treatment of neurodegenerative diseases including PD, dystonia, tardive dyskinesia and other movement disorders and may offer the clinical benefit of scopolamine, without the adverse effects mediated by pan-mAChR inhibition.

In some embodiments, the disclosed compounds are antagonists of mAChR $M_4$. Such activity can be demonstrated by methodology known in the art. For example, antagonism of mAChR $M_4$ activity can be determined by measurement of calcium flux in response to agonist, e.g. acetylcholine, in cells loaded with a $Ca^{2+}$-sensitive fluorescent dye (e.g., Fluo-4) and co-expression of a chimeric or promiscuous G protein. In some embodiments, the calcium flux can be measured as an increase in fluorescent static ratio. In some embodiments, antagonist activity can be analyzed as a concentration-dependent increase in the $EC_{80}$ acetylcholine response (i.e. the response of mAChR $M_4$ at a concentration of acetylcholine that yields 80% of the maximal response).

In some embodiments, the disclosed compounds antagonize mAChR $M_4$ as a decrease in calcium fluorescence in mAChR $M_4$-transfected CHO-K1 cells in the presence of the compound, compared to the response of equivalent CHO-K1 cells in the absence of the compound. In some embodiments, a disclosed compound antagonizes the mAChR $M_4$ response with an $IC_{50}$ of less than about 10 μM less than about 5 μM, less than about 1 μM, less than about 500 nM, of less than about 100 nM, or less than about 50 nM. In some embodiments, the mAChR $M_4$-transfected CHO-K1 cells are transfected with human mAChR $M_4$. In some embodiments, the mAChR $M_4$-transfected CHO-K1 cells are transfected with rat mAChR $M_4$. In some embodiments, the mAChR $M_4$-transfected CHO-K1 cells are transfected with mAChR $M_4$ from dog or cynomolgus monkey.

The disclosed compounds may antagonize mAChR $M_4$ response in mAChR $M_4$-transfected CHO-K1 cells with an $IC_{50}$ less than the $IC_{50}$ for one or more of mAChR $M_1$, $M_2$, $M_3$ or $M_5$-transfected CHO-K1 cells. That is, a disclosed compound can have selectivity for the mAChR $M_4$ receptor vis-à-vis one or more of the mAChR $M_1$, $M_2$, $M_3$ or $M_5$ receptors. For example, in some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_1$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, a disclosed compound can antagonize mAChR M response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR MA. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, a disclosed compound can antagonize mAChR $M_4$ response with an $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, or greater than about 500-fold less than that for the mAChR $M_1$, $M_2$, $M_3$, or $M_5$ receptors.

The disclosed compounds may antagonize mAChR $M_4$ response in $M_4$-transfected CHO-K1 cells with an $IC_{50}$ of less than about 10 μM and exhibit a selectivity for the $M_4$ receptor vis-A-vis one or more of the mAChR $M_1$, $M_2$, $M_3$, or $M_5$ receptors. For example, in some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, 10-fold less, 20-fold less, 30-fold less, 50-fold less, 100-fold less, 200-fold less, 300-fold less, 400-fold less, or greater than about 500-fold less than that for mAChR $M_1$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR M response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, the compound can have an $IC_{50}$ of less than about 10 μM, of less than about 5 μM, of less than about 5 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, the compound can have an $IC_{50}$ of less than about 10 μM, of less than about 5 μM of less than about 1 μM, of less than about 500 nM, of less than about 100 nM, or of less than about 50 nM; and the compound can also antagonize mAChR $M_4$ response with $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, $M_2$, $M_3$, or $M_5$ receptors, or greater than about 500-fold less than that for the mAChR $M_1$, $M_2$, $M_3$, or $M_5$ receptors.

In vivo efficacy for disclosed compounds in models that predict antiparkinsonian activity can be measured in a number of preclinical rat models. For example, disclosed compounds may reverse deficits in motor function induced by the dopamine receptor antagonist in mice or rats. Also, these compounds may reverse deficits in motor function that are observed with other manipulations that reduce dopaminergic signaling, such as selective lesions of dopamine neurons. In addition, it is possible that these compounds will have efficacy in animal models of dystonia and may increase attention, cognitive function, and measures of motivation in animal models.

3. Pharmaceutical Compositions and Formulations

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (T) or any of its subformulas) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I) or any of its subformulas, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I) or any of its subformulas) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I) or any of its subformulas), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I) or any of its subformulas), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition or formulation may antagonize mAChR $M_4$ with an $IC_{50}$ of less than about 10 μM, less than about 5 μM, less than about 1 μM, less than about 500 nM, or less than about 100 nM. The pharmaceutical composition or formulation may antagonize mAChR $M_4$ with an $IC_{50}$ of between about 10 μM and about 1 nM, about 1 μM and about 1 nM, about 100 nM and about 1 nM, or between about 10 nM and about 1 nM.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I) or any of its subformulas.

4. Methods of Use

The disclosed compounds, pharmaceutical compositions and formulations may be used in methods for treatment of disorders, such as neurological and/or psychiatric disorders, associated with muscarinic acetylcholine receptor dysfunction. The disclosed compounds and pharmaceutical compositions may also be used in methods for decreasing muscarinic acetylcholine receptor activity in a mammal. The methods further include cotherapeutic methods for improving treatment outcomes. In the methods of use described herein, additional therapeutic agent(s) may be administered simultaneously or sequentially with the disclosed compounds and compositions.

a. Treating Disorders

The disclosed compounds, pharmaceutical compositions and formulations may be used in methods for treating, preventing, ameliorating, controlling, reducing, or reducing the risk of a variety of disorders, or symptoms of the disorders, in which a patient would benefit from antagonism of mAChR $M_4$. In some embodiments, the disorder may be a neurodegenerative disorder, a movement disorder, or a brain disorder. The methods may comprise administering to a subject in need of such treatment a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof.

Disorders in which a patient would benefit from antagonism of mAChR $M_4$ may include neurodegenerative disorders and movement disorders. For example, exemplary disorders may include Parkinson's disease, drug-induced Parkinsonism, dystonia, Tourette's syndrome, dyskinesias (e.g., tardive dyskinesia or levodopa-induced dyskinesia), schizophrenia, cognitive deficits associated with schizophrenia, excessive daytime sleepiness (e.g., narcolepsy), attention deficit hyperactivity disorder (ADHD), Huntington's disease, chorea (e.g., chorea associated with Huntington's disease), cerebral palsy, and progressive supranuclear palsy.

In some embodiments, the disclosure provides a method for treating motor symptoms in a subject having Parkinson's disease, comprising administering to a subject in need thereof a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. In some embodiments, the motor symptoms are selected from bradykinesia, tremor, rigidity, gait dysfunction, and postural instability. The method may treat the motor symptoms, control the motor symptoms, and/or reduce the motor symptoms in the subject.

In some embodiments, the disclosure provides a method for treating motor symptoms in a subject having dystonia, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. The method may treat the motor symptoms, control the motor symptoms, and/or reduce the motor symptoms in the subject. For example, treatment may reduce muscle contractions or spasms in a subject having dystonia.

In some embodiments, the disclosure provides a method for treating motor symptoms in a subject having tardive dyskinesia, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. The method may treat the motor symptoms, control the motor symptoms, and/or reduce the motor symptoms in the subject. For example, treatment may reduce involuntary movements in a subject having tardive dyskinesia.

In some embodiments, the disclosure provides a method of preventing or delaying tardive dyskinesia in a subject at risk of developing tardive dyskinesia, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. For example, the subject may be a subject being treated with a neuroleptic medication (e.g., a typical antipsychotic or an atypical antipsychotic), a dopamine antagonist, or an antiemetic.

In some embodiments, the disclosure provides a method of treating catalepsy in a subject suffering from schizophrenia, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. For example, the subject suffering from schizophrenia may have catalepsy induced by a neuroleptic agent (e.g., a typical antipsychotic or an atypical antipsychotic).

In some embodiments, the disclosure provides a method of treating a brain disorder characterized by altered dopamine and cholinergic signaling that could benefit from antagonism of mAChR $M_4$, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. For example, the treatment may increase motivation or goal-directed behavior in patients suffering from disorders characterized by reduced motivation for goal-directed behavior, such as schizophrenia and other brain disorders.

In some embodiments, the disclosure provides a method for increasing wakefulness and/or reducing excessive daytime sleepiness in a subject in need thereof, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. In some embodiments, the subject is a subject suffering from narcolepsy.

In some embodiments, the disclosure provides a method of increasing attention in a subject (e.g., a subject suffering from an attention deficit disorder such as ADHD) in a subject in need thereof, comprising administering to the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof.

In some embodiments, the disclosure provides a method for treating motor symptoms in a subject having a drug-induced movement disorder, comprising administering the subject a therapeutically effective amount of the compound of formula (I) or any of its subformulas or a pharmaceutically acceptable salt thereof, or a pharmaceutical composition comprising a therapeutically effective amount of a compound of formula (I) or any of its subformulas or a pharmaceutically acceptable salt thereof. In some embodiments, the drug-induced movement disorder is selected from drug-induced parkinsonism, tardive dyskinesia, tardive dystonia, akathisia, myoclonus, and tremor. The method may treat the motor symptoms, control the motor symptoms, and/or reduce the motor symptoms in the subject.

The compounds and compositions may be further useful in a method for the prevention, treatment, control, amelioration, or reduction of risk of the diseases, disorders and conditions noted herein. The compounds and compositions may be further useful in a method for the prevention, treatment, control, amelioration, or reduction of risk of the aforementioned diseases, disorders and conditions, in combination with other agents.

In the treatment of conditions such as those that would benefit from antagonism of mAChR 4, an appropriate dosage level may be about 0.01 to 500 mg per kg patient body weight per day, which can be administered in single or multiple doses. The dosage level may be about 0.1 to about 250 mg/kg per day, or about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the disclosure relates to a method for antagonizing the mAChR $M_4$ receptor in at least one cell, comprising the step of contacting the at least one cell with at least one disclosed compound or at least one product of a disclosed method in an amount effective to antagonize mAChR $M_4$ in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for antagonizing the mAChR $M_4$ receptor in a subject, comprising the step of administering to the subject at least one disclosed compound or at least one product of a disclosed method in a dosage and amount effective to antagonize the mAChR $M_4$ receptor in the subject. In some embodiments, the subject is mammalian, for example, human. In some embodiments, the mammal has been diagnosed with a need for mAChR $M_4$ antagonism prior to the administering step. In some embodiments, the mammal has been diagnosed with a need for mAChR $M_4$ antagonism prior to the administering step. In some embodiments, the method further comprises the step of identifying a subject in need of mAChR $M_4$ antagonism.

b. Antagonism of the Muscarinic Acetylcholine Receptor

In some embodiments, the disclosure relates to a method for antagonizing mAChR $M_4$ in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, antagonism of the muscarinic acetylcholine receptor decreases muscarinic acetylcholine receptor activity.

In some embodiments, the compound administered antagonizes mAChR $M_4$ with an $IC_{50}$ of less than about 10 μM, less than about 5 μM, less than about 1 μM, less than about 500 nM, or less than about 100 nM. In some embodiments, the compound administered antagonizes mAChR $M_4$ with an $IC_{50}$ of between about 10 μM and about 1 nM, about 1 μM and about 1 nM, about 100 nM and about 1 nM, or about 10 nM and about 1 nM.

In some embodiments, the mammal is a human. In some embodiments, the mammal has been diagnosed with a need for reduction of muscarinic acetylcholine receptor activity prior to the administering step. In some embodiments, the method further comprises the step of identifying a mammal in need of reducing muscarinic acetylcholine receptor activity. In some embodiments, the antagonism of the muscarinic acetylcholine receptor treats a disorder associated with muscarinic acetylcholine receptor activity in the mammal. In some embodiments, the muscarinic acetylcholine receptor is mAChR $M_4$.

In some embodiments, antagonism of the muscarinic acetylcholine receptor in a mammal is associated with the treatment of a disorder associated with a muscarinic receptor dysfunction, such as a disorder disclosed herein. In some embodiments, the muscarinic receptor is mAChR $M_2$.

In some embodiments, the disclosure provides a method for antagonizing the muscarinic acetylcholine receptor in a cell, comprising the step of contacting the cell with an effective amount of at least one disclosed compound or a pharmaceutically acceptable salt thereof. In some embodiments, the cell is mammalian (e.g., human). In some embodiments, the cell has been isolated from a mammal prior to the contacting step. In some embodiments, contacting is via administration to a mammal.

c. Cotherapeutic Methods

The present disclosure is further directed to administration of a mAChR $M_4$ antagonist, such as a selective mAChR $M_4$ antagonist, for improving treatment outcomes. That is, in some embodiments, the disclosure relates to a cotherapeutic method comprising a step of administering to a mammal an effective amount and dosage of at least one disclosed compound, or a pharmaceutically acceptable salt thereof.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In some embodiments, administration may improve treatment outcomes in the context of physical or occupational therapy. Administration in connection with physical or occupational therapy can be continuous or intermittent. Administration need not be simultaneous with therapy and can be before, during, and/or after therapy. For example, physical or occupational therapy can be provided within 1, 2, 3, 4, 5, 6, 7 days before or after administration of the compound. As a further example, physical or occupational therapy can be provided within 1, 2, 3, or 4 weeks before or after administration of the compound. As a still further example, physical or occupational therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

d. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I) or any of its subformulas. The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In some embodiments, the compound can be employed in combination with any other agent that is used to treat a disorder described herein, such as a standard of care therapy for a disorder that would benefit from mAChR $M_4$ antagonism, such as a disorder described herein. For example, in some embodiments, the compound can be employed in combination with a Parkinsonian drug (e.g., L-DOPA, or carbidopa/levodopa) an $mGlu_4$ positive allosteric modulator, an $mGlu_5$ negative allosteric modulator, an $A_2A$ inhibitor, a T-type calcium channel antagonist, a VMAT2 inhibitor, a muscle relaxant (e.g., baclofen), an anticholinergic agent, an antiemetic, a typical or atypical neuroleptic agent (e.g., risperidone, ziprasidone, haloperidol, pimozide, fluphenazine), an antihypertensive agent (e.g., clonidine or guanfacine), a tricyclic antidepressant (e.g., amitriptyline, butriptyline, clomipramine, desipramine, dosulepin, doxepin, imipramine, iprindole, lofepramine, nortriptyline, protriptyline, or trimipramine) an agent that increases extracellular dopamine levels (e.g., amphetamine, methylphenidate, or lisdexamfetamine), an agent for treating excessive daytime sleepiness (e.g., sodium oxybate or a wakefulness-promoting agent such as armodafinil or modafinil), and a norepinephrine reuptake inhibitor (including selective NRIs, e.g., atomoxetine, and non-selective NRIs, e.g., bupropion).

e. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. Kits

In one aspect, the disclosure provides a kit comprising at least one disclosed compound or a pharmaceutically acceptable salt thereof, or a pharmaceutical composition comprising at least one disclosed compound or a pharmaceutically acceptable salt thereof and one or more of:

(a) at least one agent known to increase mAChR $M_4$ activity;

(b) at least one agent known to decrease mAChR M activity;

(c) at least one agent known to treat a disorder associated with mAChR $M_4$, such as a disorder described herein; and (d) instructions for administering the compound.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may further comprise information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Examples

All NMR spectra were recorded on a 400 MHz AMX Bruker NMR spectrometer. $^1$H chemical shifts are reported in S values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostated column compartment, $C_{18}$ column, diode-array detector (DAD) and an Agilent 6150 MSD with the following parameters. The gradient conditions were 5% to 95% acetonitrile with the aqueous phase 0.1% TFA in water over 1-4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Abbreviations that may be used in the examples that follow are:

AcOH is acetic acid;
BINAP is 2,2'-Bis(diphenylphosphino)-1,1'-binaphthyl;
Boc is tert-butyloxycarbonyl;
BrettPhos-Pd-$G^3$ is [(2-di-cyclohexylphosphino-3,6-dimethoxy-2',4',6'-triisopropyl-1,1'-biphenyl)-2-(2'-amino-1,1'-biphenyl)]palladium(II) methanesulfonate (CAS Number 1470372-59-8);
tBuOH is tert-butyl alcohol;
Celite® is diatomaceous earth;
DCE is 1,2-dichloroethane;
DCM is dichloromethane;
DIAD is diisopropylazodicarboxylate;
DIPEA is N,N-diisopropylethylamine;
DMF is N,N-dimethylformamide;
DMSO is dimethylsulfoxide;
eq, eq., or equiv is equivalent(s);
$Et_2O$ is diethylether;
EtOAc is ethyl acetate;
EtOH is ethanol;
$Et_3N$ is triethylamine;
HATU is 2-(7-aza-1H-benzotriazole-1-yl)-1,1,3,3-tetramethyluronium hexafluorophosphate;
h or h. is hour(s);
hex is hexane;
IPA is isopropyl alcohol;
LCMS is liquid chromatography mass spectrometry;
$LiAlD_4$ is lithium aluminum deuteride;
$LiAlH(OtBu)_3$ is lithium tri-tert-butoxyaluminum hydride;
m-CPBA is meta-chloroperoxybenzoic acid;
MeCN is acetonitrile;
MeMgBr is methyl magnesium bromide;
MeOH is methanol;
MeOD is deuterated methanol;
min or min. is minute(s);
MTBE is methyl tert-butyl ether;
NMP is N-methyl-2-pyrrolidone;
$Pd(OAc)_2$ is palladium(II) acetate;
$Pd(dppf)Cl_2$ is [1,1'-Bis(diphenylphosphino)ferrocene]dichloropalladium(II);
$PPh_3$ is triphenylphosphine;
RP-HPLC is reverse phase high-performance liquid chromatography;
RuPhos-Pd-G3 is (2-dicyclohexylphosphino-2',6'-diisopropoxy-1,1'-biphenyl)[2-(2'-amino-1,1'-biphenyl)]palladium(II) methanesulfonate (CAS Number 1445085-77-7);
rt, RT, or r.t. is room temperature;
sat. is saturated;
SFC is supercritical fluid chromatography;
soln. is solution;
TESCl is chlorotriethylsilane;
TFA is trifluoroacetic acid;
THF is tetrahydrofuran;
tosyl is toluenesulfonyl.

Example 1. tert-Butyl (3aR,5s,6aS)-5-((6-chloropyridazin-3-yl)amino)hexahydrocyclopenta[c]pyrrole-2(1H)-carboxylate

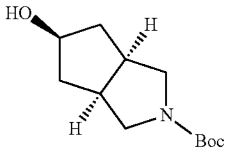 [SMILES: CC(C)(C)OC(=O)N1C[C@H]2C[C@@H](O)C[C@H]2C1]

tert-Butyl (3aR,5r,6aS)-5-hydroxy-3,3a,4,5,6,6a-hexahydro-1H-cyclopenta[c]pyrrole-2-carboxylate. To a solution of tert-butyl (3aR,6aS)-5-oxohexahydrocyclopenta[c]pyrrole-2(1H)-carboxylate (10.0 g, 44.4 mmol) in THF (300 mL) at −78° C. was added a solution of 1.0 M lithium tri-tert-butoxyaluminum hydride solution (53.3 mL, 53.3 mmol) dropwise. The resulting solution was stirred at −78° C. for 2 h, after which time the reaction mixture was warmed to 0° C. and quenched with the sequential slow addition of $H_2O$ (17.0 mL), 1 M NaOH solution (17.0 mL), and $H_2O$ (51.0 mL). The mixture was stirred at 0° C. for 1 h, after which time solids were removed by filtration with diethyl ether (3×200 mL). The filtrate was diluted with EtOAc (500 mL) and sat. $NH_4Cl$ solution (300 mL), and the aqueous layer was extracted with EtOAc (3×500 mL). The combined organic extracts were dried with $MgSO_4$, filtered, and concentrated under reduced pressure to give a crude mixture of the title compound as a yellow oil which was carried to the next step without further purification. $^1$H-NMR (400 MHz, $CDCl_3$) δ 4.30 (pent, J=6.4 Hz, 1H), 3.54-3.46 (m, 2H), 3.34 (dd, J=11.2, 3-7 Hz, 2H), 2.65-2.56 (m, 2H), 2.20-2.13 (m, 2H), 1.53-1.47 (m, 2H), 1-45 (s, 9H); d.r.=97:3; ESI-MS=$[M+H]^+$-t-Butyl=172.0.

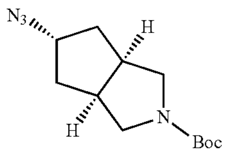 [SMILES: CC(C)(C)OC(=O)N1C[C@H]2C[C@H](N=[N+]=[N-])C[C@H]2C1]

tert-Butyl (3aR,5s,6aS)-5-azido-3,3a,4,5,6,6a-hexahydro-1H-cyclopenta[c]pyrrole-2-carboxylate. To a solution of tert-butyl (3aR,5r,6aS)-5-hydroxyhexahydrocyclopenta[c]pyrrole-2(1H)-carboxylate (10.1 g, 44.4 mmol) in DCM (250 mL), mesyl chloride (4.12 mL, 53.3 mmol), 4-dimethylaminopyridine (0.06 mL, 0.44 mmol), and N,N-diisopropylethylamine (11.6 mL, 66.6 mmol) were added. The reaction mixture was stirred at r.t. overnight. Upon completion, the reaction mixture was quenched with sat. $NaHCO_3$ (100 mL) and extracted with DCM (3×200 mL). The combined organic extracts were dried with $Na_2SO_4$, filtered, and concentrated under reduced pressure to give a crude mixture of the mesylate intermediate as an oil which was carried to the next step without further purification. ES-MS=$[M+H]^+$-t-Butyl=250.0.

A mixture of tert-butyl (3aR,5r,6aS)-5-((methylsulfonyl)oxy)hexahydrocyclopenta[c]pyrrole-2(1H)-carboxylate (13.6 g, 44.4 mmol), sodium azide (7.2 g, 111.0 mmol), and tetrabutylammonium iodide (16.4 mg, 0.04 mmol) in DMF (200 mL) was stirred at 60° C. After stirring overnight, the reaction was cooled to r.t. and diluted with EtOAc (200 mL) and $H_2O$ (100 mL). The organic layer was washed with $H_2O$, and the aqueous layer was back extracted 1× with EtOAc (200 mL). The combined organic extracts were dried with $Na_2SO_4$, and the solvents were filtered and concentrated under reduced pressure. The crude residue was purified by column chromatography on silica gel (0-100% EtOAc in hexanes) to provide the title compound as a clear oil (6.9 g, 62% over 3 steps). $^1$H-NMR (400 MHz, $CDCl_3$) S 4.14-4.10 (m, 1H), 3.50-3.48 (m, 2H), 3.22-3.16 (m, 2H), 2.84-2.78 (m, 2H), 2.03-1.97 (m, 2H), 1.76-1.68 (m, 2H), 1-45 (s, 9H); ES-MS=$[M+H]^+$-t-Butyl=197.0.

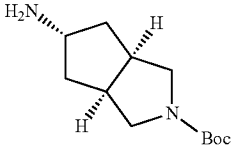 [SMILES: CC(C)(C)OC(=O)N1C[C@H]2C[C@H](N)C[C@H]2C1]

tert-Butyl (3aR,5s,6aS)-5-amino-3,3a,4,5,6,6a-hexahydro-1H-cyclopenta[c]pyrrole-2-carboxylate. tert-Butyl (3aR,5s,6aS)-5-azido-3,3a,4,5,6,6a-hexahydro-1H-cyclopenta[c]pyrrole-2-carboxylate (6.4 g, 25.3 mmol) was dissolved in THF (400 mL), and 20% wt $Pd(OH)_2$/C (1.8 g, 2.5 mmol) was added. The resulting mixture was stirred under $H_2$ (balloon) at 0° C. for 8 h, then slowly warmed to r.t. and stirred overnight, after which time the reaction mixture was filtered through a pad of Celite® with EtOAc and concentrated under reduced pressure. The crude residue was purified by column chromatography on silica gel (0-100% DCM, MeOH, $NH_4OH$ (89:10:1) in DCM) to provide the title compound as a solid (5.3 g, 93%). $^1$H-NMR (400 MHz, MeOD) δ 3.54-3.43 (m, 3H), 3.33-3.32 (m, 2H), 3.17-3.12 (m, 2H), 2.86-2.80 (m, 2H), 1.81-1.75 (m, 2H), 1.70-1.62 (m, 2H), 1-47 (s, 9H); ES-MS $[M+H]^+$=227.0.

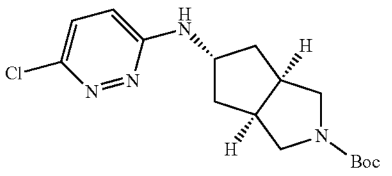 [SMILES: CC(C)(C)OC(=O)N1C[C@H]2C[C@H](Nc3ccc(Cl)nn3)C[C@H]2C1]

tert-Butyl (3aR,5s,6aS)-5-((6-chloropyridazin-3-yl)amino)hexahydrocyclopenta[c]pyrrole-2(1H)-carboxylate. 3,6-Dichloropyridazine (3.95 g, 26.5 mmol, 3 eq), tert-butyl (3aR,5s,6aS)-5-aminohexahydrocyclopenta[c]pyrrole-2(1H)-carboxylate (2 g, 8.84 mmol, 1 eq), and DIPEA (4.62 mL, 26.5 mmol, 3 eq) were suspended in tert-butanol (40 mL) in a microwave vial and heated under microwave irradiation at 150° C. for 2 h. The reaction was concentrated in vacuo and purified by column chromatography (0-80% EtOAc in hexanes) to afford the title compound (967 mg, 32%). $^1$H-NMR (400 MHz, MeOD) δ 7.27 (d, J=9.4 Hz, 1H), 6.87 (d, J=9.4 Hz, 1H), 4.41 (p, J=6.3 Hz, 1H), 3.55 (dd, J=11-4, 8.0 Hz, 2H), 3.19 (dd, J=11-4, 3.9 Hz, 2H), 2.90-2.80 (m, 2H), 1.98-1.92 (m, 2H), 1.89-1.82 (m, 2H), 1-46 (s, 9H). ES-MS $[M+H]^+$-t-Butyl=283.4.

Example 2. (3aR,5s,6aS)—N-(6-Chloropyridazin-3-yl)-2-((tetrahydro-2H-pyran-4-yl)methyl-$d_2$)octahydrocydopenta[c]pyrrol-5-amine

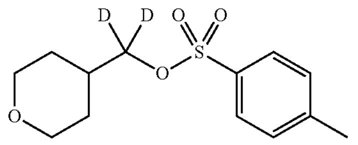 [SMILES: [2H]C([2H])(OS(=O)(=O)c1ccc(C)cc1)C1CCOCC1]

(Tetrahydro-2H-pyran-4-yl)methyl-$d_2$ 4-methylbenzenesulfonate. Lithium aluminum deuteride (2.0 g, 53 mmol, 2.5 eq) was added to THF (60 mL) at 0° C. The resulting solution was placed under an inert atmosphere, followed by the dropwise addition of methyl tetrahydro-2H-pyran-4-carboxylate (3.0 g, 21 mmol, 1 eq). The resulting solution stirred while warming to r.t. for 2 h, after which time the reaction was chilled to 0° C. and quenched with the slow repeated addition of 0.05 mL water and 0.15 mL of 1N NaOH solution until 2 mL of water and 5 mL of NaOH solution had been added. The mixture then stirred at r.t. for 1 h, after which time the aluminum precipitate was filtered off and washed several times with THF and DCM. The organic layer was dried over $MgSO_4$ and solvents were removed under reduced pressure (2.46 g, 100%). The resulting alcohol was suspended in DCM (30 mL), followed by the addition of triethylamine (6.4 mL, 2.2 eq) and tosyl chloride (5.1 g, 27 mmol, 1-3 eq), and heated to 40° C. overnight. Solvents were concentrated and crude residue was purified by column chromatography (3-70% EtOAc in hexanes). Fractions containing product were concentrated to yield the title compound as a white crystalline solid (3.55 g, 63% over 2 steps). $^1$H NMR (400 MHz, $CDCl_3$) δ 7.77 (d, J=8.2 Hz, 2H), 7.34 (d, J=8.2 Hz, 2H), 3.92 (dd, J=11.6, 3.9

Hz, 2H), 3.32 (td, J=11.8, 2.1 Hz, 2H), 2.44 (s, 3H), 1.91 (tt, J=11.7, 3.9 Hz, 1H), 1.59-1.52 (m, 2H), 1.31-1.19 (m, 2H). ES-MS $[M+H]^+$=273.2.

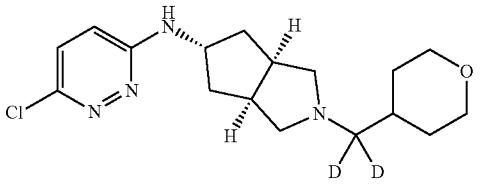 [SMILES: [2H]C([2H])(C1CCOCC1)N1C[C@H]2C[C@H](Nc3ccc(Cl)nn3)C[C@H]2C1]

(3aR,5s,6aS)—N-(6-Chloropyridazin-3-yl)-2-((tetrahydro-2H-pyran-4-yl)methyl-$d_2$)octahydrocyclopenta[c]pyrrol-5-amine. Tert-butyl (3aR,5s,6aS)-5-((6-chloropyridazin-3-yl)amino)hexahydrocyclopenta[c]pyrrole-2(1H)-carboxylate (760 mg, 2.2 mmol, 1 eq) was dissolved in MeOH (5 mL), and 4M HCl in dioxanes solution (17 mL) was added dropwise. The resulting solution was stirred at r.t. for 1 h, after which time solvents were concentrated under reduced pressure to afford the HCl salt as a white solid, which was dried under vacuum and used without additional purification (620 mg, 100%). The HCl amine was suspended in THF (6 mL), followed by the slow addition of NaOH (650 mg, 16 mmol, 7 eq) in $H_2O$ (6 mL). The solution was stirred for 5 min at r.t., followed by the addition of (tetrahydro-2H-pyran-4-yl)methyl-d2 4-methylbenzenesulfonate (1800 mg, 6.7 mmol, 3 eq). The resulting solution was sealed and heated to 80° C. for 18 h. Solvents were concentrated and the resulting solid was washed multiple times with EtOAc. The organic layer was concentrated, and the resulting crude residue was purified by RP-HPLC (20-55% MeCN in 0.05% $NH_4OH$ aqueous solution over 20 min.). Fractions containing product were extracted in DCM and dried over $MgSO_4$. Solvents were concentrated under reduced pressure to yield the title compound as a white solid (395 mg, 52%). $^1H$ NMR (400 MHz, $CDCl_3$) δ 7.15 (d, J=9.3 Hz, 1H), 6.66 (d, J=9.3 Hz, 1H), 4.96 (d, J=7.3 Hz, 1H), 4.38-4.27 (m, 1H), 3.96 (dd, J=11.5, 3.6 Hz, 2H), 3.38 (td, J=11.7, 1.9 Hz, 2H), 2.85-2.68 (m, 4H), 2.45-2.35 (m, 2H), 1.99-1.91 (m, 2H), 1.76-1.66 (m, 5H), 1.35-1.24 (m, 2H). ES-MS $[M+H]^+$=339.2.

Example 3. (3aR,5s,6aS)—N-(6-Chloropyridazin-3-yl)-2-((tetrahydro-2H-pyran-4-yl)methyl-$d_2$)octahydrocyclopenta[c]pyrrol-5-amine (Alternate Synthesis)

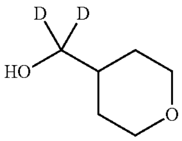

(Tetrahydro-2H-pyran-4-yl)methan-$d_2$-ol. To a solution of lithium aluminum deuteride (1-45 g, 38.1 mmol, 1.1 eq) in THF (30 mL) was added a solution of methyl tetrahydro-2H-pyran-4-carboxylate (5.00 g, 34.7 mmol, 1 eq) in THF (70 mL) dropwise at 0° C. under an inert atmosphere. The resulting reaction mixture was warmed to r.t. and stirred for 1.5 h, after which time the reaction was cooled back to 0° C., and $H_2O$ (1 mL), 1M NaOH (1 mL) and $H_2O$ (3 mL) were added sequentially. The reaction mixture was warmed to r.t.

and stirred for 5 min, after which time $MgSO_4$ was added with additional stirring. The reaction mixture was filtered through a pad of Celite® with EtOAc. The filtrate was concentrated to afford the title compound as a slightly yellow oil which was used directly without further purification (4.10 g, 100%). $^1H$ NMR (400 MHz, $CDCl_3$) δ 4.02-3.92 (m, 2H), 3.39 (td, J=11.8, 2.2 Hz, 2H), 1.78-1.72 (m, 1H), 1.64 (ddd, J=13.3, 4.1, 2.1 Hz, 2H), 1-39-1.20 (m, 2H).

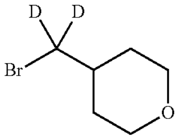

4-(Bromomethyl-$d_2$)tetrahydro-2H-pyran. (tetrahydro-2H-pyran-4-yl)methan-$d_2$-ol (4.10 g, 34.7 mmol, 1 eq) and triphenylphosphine (11.8 g, 45.1 mmol, 1.3 eq) were dissolved in DCM (100 mL) and cooled to 0° C. Carbon tetrabromide (15.0 g, 45.1 mmol, 1.3 eq) was then added. The resulting solution was warmed to r.t. and stirred overnight under an inert atmosphere, after which time $H_2O$ was added. The aqueous layer was extracted with DCM, and combined organic extracts were washed with brine, dried over $MgSO_4$, and solvents were filtered and removed. Crude residue was purified by column chromatography (3-20% EtOAc in hexanes) to afford the title compound as a colorless liquid (4.61 g, 73%). $^1H$ NMR (400 MHz, $CDCl_3$) δ 4.01-3.96 (m, 2H), 3.37 (td, J=11.9, 2.1 Hz, 2H), 1.91-1.84 (m, 1H), 1.76 (ddd, J=13.1, 4.0, 2.0 Hz, 2H), 1.40-1.30 (m, 2H).

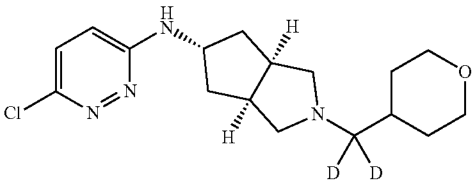 [SMILES: [2H]C([2H])(C1CCOCC1)N1C[C@H]2C[C@H](Nc3ccc(Cl)nn3)C[C@H]2C1]

(3aR,5s,6aS)—N-(6-Chloropyridazin-3-yl)-2-((tetrahydro-2H-pyran-4-yl)methyl-$d_2$)octahydrocyclopenta[c]pyrrol-5-amine. (3aR,5s,6aS)—N-(6-chloropyridazin-3-yl)octahydrocyclopenta[c]pyrrol-5-amine (1.00 g, 4.19 mmol, 1 eq) and 4-(bromomethyl-$d_2$)tetrahydro-2H-pyran (1.02 g, 5.66 mmol, 1.35 eq) were suspended in 1,4-dioxane (3.5 mL), and NaOH (859 mg, 20.9 mmol, 5 eq) in $H_2O$ (1.5 mL) was added. The resulting reaction mixture was stirred at 100° C. overnight, after which time solvents were concentrated, and residue was taken up in DCM and $H_2O$. Aqueous layer was extracted with DCM, and combined organic extracts were dried with $MgSO_4$. Solvents were filtered and concentrated to afford the title compound as a tan solid which was used without further purification (1.04 g, 73%). $^1H$ NMR (400 MHz, $CDCl_3$) S 7.16 (d, J=9.2 Hz, 1H), 6.63 (d, J=9.2 Hz, 1H), 4.83 (d, J=7.2 Hz, 1H), 4.22-4.32 (m, 1H), 3.94-3.99 (m, 2H), 3.35-3.42 (m, 2H), 2.65-2.79 (m, 2H), 2.51-2.62 (m, 2H), 2.30-2.37 (m, 2H), 1.89-1.96 (m, 2H), 1.63-1.74 (m, 5H), 1.22-1.34 (m, 2H). ES-MS $[M+H]^+$=339.2.

Example 4.

Tetrahydro-2H-pyran-4-carboxylic-2,2,6,6-$d_4$ acid

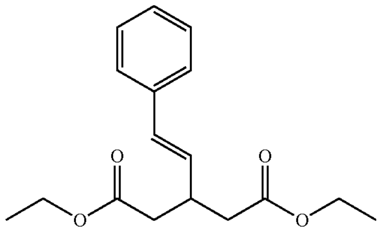 [SMILES: CCOC(=O)CC(/C=C/c1ccccc1)CC(=O)OCC]

(E)-Diethyl 3-styrylpentanedioate. A mixture of cinnamaldehyde (60 g, 456 mmol, 57.4 mL, 1 eq), 3-ethoxy-3-oxopropanoic acid (301.4 g, 2281 mmol, 5 eq), and DMAP (11.2 g, 91-3 mmol, 0.2 eq), in pyridine (210 mL) was degassed and purged with $N_2$, and the mixture was stirred at 60° C. for 20 h under an inert atmosphere. The mixture was then stirred at 140° C. for 48 h. The reaction mixture was concentrated under reduced pressure to remove pyridine. The residue was then diluted with $H_2O$ and extracted with MTBE. The combined organic layers were washed with HCl (15%) dried over $Na_2SO_4$, filtered and concentrated under reduced pressure to give a residue. The residue was purified by column chromatography ($SiO_2$, petroleum ether/ethyl acetate=I/O to 10/1) to afford the title compound as a yellow solid (27 g, 61%). $^1H$ NMR (400 MHz, $CDCl_3$) S 7.27-7.37 (m, 4H) 7.17-7.25 (m, 1H) 6.48 (d, J=15.9 Hz, 1H) 6.12 (dd, J=15.8, 8.4 Hz, 1H) 4.13 (q, J=7.1 Hz, 4H) 3.23 (dq, J=14.6, 7.2 Hz, 1H) 2.52 (qd, J=15.4, 7.1 Hz, 4H) 1.23 (t, J=7.1 Hz, 6H).

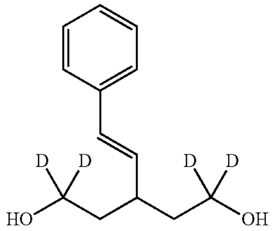 [SMILES: [2H]C([2H])(O)CC(/C=C/c1ccccc1)CC([2H])([2H])O]

1,1,5,5-Tetradeuterio-3-[(E)-styryl]pentane-1,5-diol. To a solution of lithium aluminum deuteride (7.60 g, 180.8 mmol, 1.5 eq) in THF (80 mL) was added (E)-diethyl 3-styrylpentanedioate (35 g, 120.5 mmol, 1 eq) in THF (350 mL) dropwise at 0° C. The resulting mixture was stirred at 20° C. for 1 h. To the reaction mixture was added $H_2O$ (76 mL), 15% NaOH aq solution (76 mL) and $H_2O$ (227 mL) sequentially, with stirring. $MgSO_4$ was added with stirring, and the reaction mixture was filtered through a pad of Celite®. The filtrate was concentrated under reduced pressure to afford the title compound as a white solid (20.4 g, 80%). $^1H$ NMR (400 MHz, $CDCl_3$) δ 7.27-7.37 (m, 4H) 7.17-7.23 (m, 1H) 6.43 (d, J=15.8 Hz, 1H) 5.96 (dd, J=15.9, 9.1 Hz, 1H) 2.54 (qt, J=9.2, 4.8 Hz, 1H) 1.72 (dd, J=13.8, 4.9 Hz, 2H) 1.52-1.64 (m, 2H).

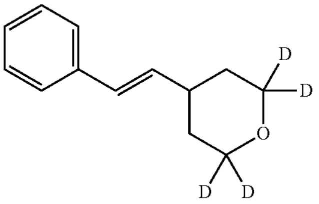 [SMILES: [2H]C1([2H])CC(/C=C/c2ccccc2)CC([2H])([2H])O1]

2,2,6,6-Tetradeuterio-4-[(E)-styryl]tetrahydropyran. A mixture of 1,1,5,5-tetradeuterio-3-[(E)-styryl]pentane-1,5-diol (14 g, 66.6 mmol, 1 eq), and TsOH (2.29 g, 13.3 mmol, 0.2 eq) in toluene (140 mL) was heated to reflux with a Dean-Stark trap at 140° C. for 12 h. The resulting residue was poured into sat $NaHCO_3$ solution. The aqueous phase was extracted with ethyl acetate, and the combined organic phases were washed with brine, dried with anhydrous $Na_2SO_4$, filtered, and concentrated under reduced pressure. The crude residue was purified by column chromatography ($SiO_2$, petroleum ether/ethyl acetate=20/1 to 5/1) to afford the title compound as a colorless oil (7.23 g, 56%). $^1H$ NMR (400 MHz, $CDCl_3$) δ 7.28-7.41 (m, 4H) 7.20-7.26 (m, 1H) 6.41 (d, J=16.0 Hz, 1H) 6.18 (dd, J=16.0, 6.8 Hz, 1H) 2.34-2.46 (m, 1H) 1.68-1.75 (m, 2H) 1.52-1.63 (m, 2H).

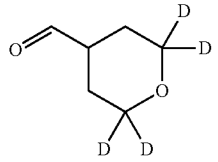 [SMILES: [2H]C1([2H])CC(C=O)CC([2H])([2H])O1]

2,2,6,6-Tetradeuteriotetrahydropyran-4-carbaldehyde. Ozone was bubbled into a solution of 2,2,6,6-tetradeuterio-4-[(E)-styryl]tetrahydropyran (6.0 g, 31.2 mmol, 1 eq) in DCM (90 mL) and MeOH (18 mL) at −78° C. for 30 min. After excess 03 was purged by $N_2$, $Me_2S$ (22 mL) was added at 20° C. for 2 h. The reaction mixture was concentrated to afford the crude product. The crude residue was purified by column chromatography ($SiO_2$, petroleum ether/ethyl acetate=10/1 to 1/1) to afford the title compound as a colorless oil (3.05 g, 83%). $^1H$ NMR (400 MHz, $CDCl_3$) λ 9.64 (s, 1H) 2.43-2.55 (m, 1H) 1.83 (dd, J=13.8, 4.1 Hz, 2H) 1.63-1.71 (m, 2H).

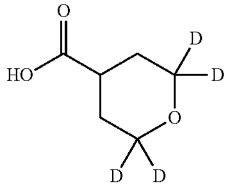 [SMILES: [2H]C1([2H])CC(C(=O)O)CC([2H])([2H])O1]

2,2,6,6-Tetradeuteriotetrahydropyran-4-carboxylic acid. To a solution of 2,2,6,6-tetradeuteriotetrahydropyran-4-carbaldehyde (3.0 g, 25.4 mmol, 1 eq) in t-BuOH (30 mL), $H_2O$ (10 mL) and THF (15 mL) was added $NaClO_2$ (6.89 g, 76.2 mmol, 3 eq), $NaH_2PO_4$ (9.14 g, 76.2 mmol, 3 eq) and 2-methylbut-2-ene (14.2 g, 203 mmol, 21.5 mL, 8 eq). The resulting mixture was stirred at 25° C. for 12 h. The reaction mixture was then quenched by addition $H_2O$at 20° C. and was then adjusted to pH 2 with 1 M HCl and extracted. The combined organic layers were washed with brine and dried over $Na_2SO_4$. Solvents were filtered and concentrated under reduced pressure to afford the title compound as a white solid (2.1 g, 62%). $^1H$ NMR (400 MHz, $CDCl_3$) δ 9.76-12.28 (m, 1H) 2.58 (tt, J=10.8, 4.3 Hz, 1H) 1.83-1.91 (m, 2H) 1.73-1.83 (m, 2H).

Example 5. 2,2-Difluoro-2-(tetrahydro-2H-pyran-4-yl)ethyl-1,1-$d_2$ 4-methylbenzenesulfonate

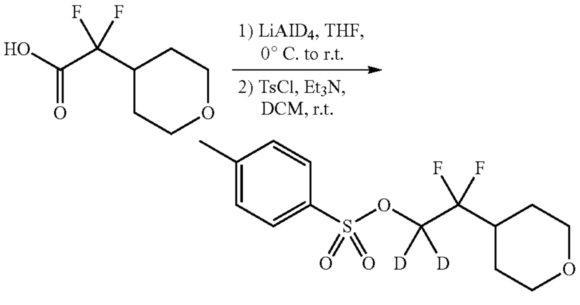

2,2-Difluoro-2-(tetrahydro-2H-pyran-4-yl)ethyl-1,1-$d_2$ 4-methylbenzenesulfonate. A solution of lithium aluminum deuteride (208 mg, 5.48 mmol, 2.1 eq), in THF (20 mL) was cooled to 0° C., and 2,2-difluoro-2-(tetrahydro-2H-pyran-4-yl)acetic acid (470 mg, 2.61 mmol, 1 eq) was added. The reaction mixture was stirred at 0° C. for 15 min, then warmed to r.t. After 2 h, the reaction mixture was quenched with the slow addition of $H_2O$ (0.05 mL) and 1M NaOH (0.15 mL). After stirring an additional 30 min, precipitates were removed by filtration and rinsed with THF. Solvents were concentrated nearly to dryness until ~10 mL solution remained. To this solution was added DCM (30 mL) and trimethylamine (0.8 mL, 5.74 mmol, 2.2. eq) with stirring. Tosyl chloride (597 mg, 3.13 mmol, 1.2 eq) was then added, and the reaction mixture was allowed to stir overnight. Solvents were concentrated, and the crude residue was purified by column chromatography (3-80% EtOAc in hexanes) to afford the title compound as a white solid (362 mg, 43% over 2 steps). $^1H$ NMR (400 MHz, $CDCl_3$) δ 7.81 (d, J=8.3 Hz, 2H), 7.38 (d, J=8.0 Hz, 2H), 4.01 (dt, J=11-4, 3.3 Hz, 2H), 3.35 (ddd, J=11.6, 8.7, 5.6 Hz, 2H), 2.47 (s, 3H), 2.27-2.12 (m, 1H), 1.64-1.52 (m, 4H). ES-MS $[M+H]^+$=323.0.

Example 6. (3aR,5s,6aS)—N-(6-Chloropyridazin-3-yl)octahydrocyclopenta[c]pyrrol-5-amine dihydrochloride

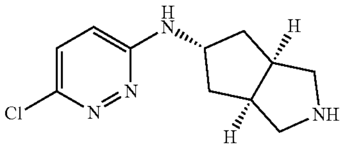

2HCl tert-Butyl (3aR,5s,6aS)-5-((6-chloropyridazin-3-yl)amino)hexahydrocyclopenta[c]pyrrole-2(1H)-carboxylate (2.22 g, 6.55 mmol) was dissolved in 1,4-dioxane (22 mL) and MeOH (2 mL) and 4M HCl in dioxanes solution (16 mL) was added dropwise. The resulting mixture was stirred at r.t. overnight, after which time solvents were concentrated under reduced pressure, and the resulting white solid was dried under vacuum and used directly without further purification (2.04 g, 100%). ES-MS $[M+H]^+$=239.4.

Example 7. (3aR,5s,6aS)—N-(6-Chloropyridazin-3-yl)-2-((tetrahydro-2H-pyran-4-yl)methyl)octahydrocyclopenta[c]pyrrol-5-amine

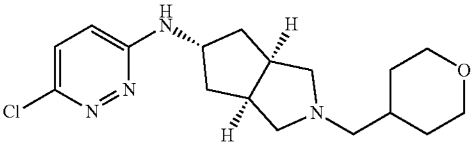 [SMILES: Clc1ccc(N[C@H]2C[C@@H]3CN(CC4CCOCC4)C[C@@H]3C2)nn1]

(3aR,5s,6aS)—N-(6-Chloropyridazin-3-yl)octahydrocyclopenta[c]pyrrol-5-amine dihydrochloride (2.04 g, 6.55 mmol) was dissolved in DCM (30 mL) and THF (30 mL) and tetrahydro-2H-pyran-4-carbaldehyde (2.05 mL, 19.7 mmol) was added, and the resulting solution was stirred for 10 mins. Sodium triacetoxyborohydride (4.17 g, 19.7 mmol) was then added. The resulting solution was stirred at r.t. for 2 h, after which time the reaction was quenched with the slow addition of sat. $NaHCO_3$, and the aqueous layer was extracted with 3:1 chloroform/IPA. The combined organic extracts were dried with $MgSO_4$, and solvents were filtered and concentrated under reduced pressure, and the resulting yellow solid was used without further purification (1.75 g, 79%). $^1H$-NMR (400 MHz, $CDCl_3$) δ 7.15 (d, J=9.3 Hz, 1H), 6.63 (d, J=9.3 Hz, 1H), 4.84 (d, J=7.0 Hz, 1H), 4.32-4.24 (m, 1H), 3.96 (dd, J=10.9, 3.7 Hz, 2H), 3.38 (td, J=11.9, 1.9 Hz, 2H), 2.78-2.54 (m, 4H), 2.36-2.27 (m, 4H), 1.95-1.91 (m, 2H), 1.72-1.65 (m, 5H), 1.33-1.23 (m, 2H). ES-MS $[M+H]^+$=337.2.

Example 8. (3aR,5s,6aS)—N-(6-Chloropyridazin-3-yl)-2-((tetrahydro-2H-pyran-4-yl)methyl)octahydrocyclopenta[c]pyrrol-4,4,6,6-$d_4$-5-amine

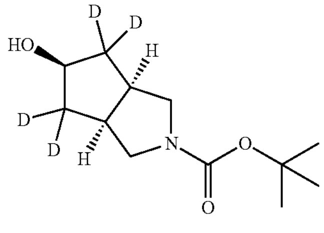 [SMILES: [2H]C1([2H])[C@@H](O)C([2H])([2H])[C@H]2CN(C(=O)OC(C)(C)C)C[C@H]21]

tert-Butyl (3aR,5r,6aS)-5-hydroxyhexahydrocyclopenta[c]pyrrole-2(1H)-carboxylate-4,4,6,6-$d_4$. tert-Butyl (3aR,6aS)-5-oxohexahydrocyclopenta[c]pyrrole-2(1H)-carboxylate (500.0 mg, 2.2 mmol, 1.0 eq), $D_2O$ (1.08 mL, 66.6 mmol, 30.0 eq), $CD_3OD$ (0.5 mL), and sodium carbonate (12.0 mg, 0.1 mmol, 0.05 eq) were mixed in a vial. The reaction mixture was stirred at 40° C. for 7 days, followed by an additional 7 days stirring at r.t. Upon completion, the reaction mixture was extracted with DCM (3×3.0 mL) and passed through the phase separator. The combined organic extracts were concentrated under reduced pressure. The crude residue was used for the next step without further purification. ES-MS $[M+H]^+$=174.0 (-t-butyl). tert-Butyl (3aR,6aS)-5-oxohexahydrocyclopenta[c]pyrrole-2(1H)-carboxylate-4,4,6,6-$d_4$ (508.9 mg, 2.2 mmol, 1.0 eq) was dissolved in MeOH (20 mL), and sodium borohydride (126.0 mg, 3.3 mmol, 1.5 eq) was added at 0° C. The resulting solution was stirred at 0° C. for 3 h, after which time the reaction mixture was quenched with sat. $NH_4Cl$ solution (3.0 mL) and diluted with EtOAc (20.0 mL) and $H_2O$ (5.0 mL). The aqueous layer was extracted with EtOAc (3×20.0 mL), and the combined organic extracts were dried with $Na_2SO_4$, filtered, and concentrated under reduced pressure. The crude residue was then purified by column chromatography (0-100% EtOAc in hexanes to 0-20% MeOH in DCM) to give the title compound (410 mg, 79% over 2 steps), which was used for the next step without further purification. $^1$H-NMR (400 MHz, $CDCl_3$) δ 4.17 (s, 1H), 3-46-3.36 (m, 2H), 3.23 (dd, J=11.0, 3-4 Hz, 2H), 2.51-2.44 (m, 2H), 1-36 (s, 9H). ES-MS $[M+H]^+$=176.0 (-t-butyl).

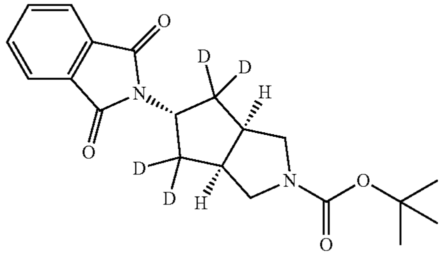 [SMILES: [2H]C1([2H])[C@H](N2C(=O)c3ccccc3C2=O)C([2H])([2H])[C@H]2CN(C(=O)OC(C)(C)C)C[C@H]21]

tert-Butyl (3aR,5s,6aS)-5-(1,3-dioxoisoindolin-2-yl)hexahydrocyclopenta[c]pyrrole-2(1H)-carboxylate-4,4,6,6-$d_4$. tert-Butyl (3aR,5r,6aS)-5-hydroxyhexahydrocyclopenta[c]pyrrole-2(1H)-carboxylate-4,4,6,6-$d_4$ (491 mg, 2.12 mmol, 1 eq.), triphenylphosphine (723 mg, 2.76 mmol, 1-3 eq.), and phthalimide (406 mg, 2.76 mmol, 1-3 eq.) were dissolved in THF (15 mL) and placed under an inert atmosphere. The solution was cooled to 0° C., and diisopropyl azodicarboxylate (0.54 mL, 2.76 mmol, 1-3 eq.) was added dropwise. The resulting solution was warmed to r.t. and stirred for 1 h, after which time the reaction was quenched with MeOH, and solvents were concentrated under reduced pressure. The crude residue was purified by column chromatography (3-80% EtOAc in hexanes) to give the title compound as a white solid (410 mg, 54%), which was used for the next step without further purification. ES-MS $[M+H]^+$=305.2 (-t-butyl).

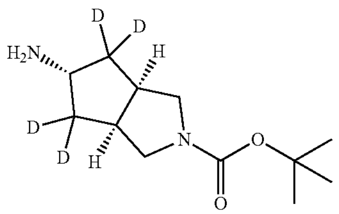 [SMILES: [2H]C1([2H])[C@H](N)C([2H])([2H])[C@H]2CN(C(=O)OC(C)(C)C)C[C@H]21]

tert-Butyl (3aR,5s,6aS)-5-aminohexahydrocyclopenta[c]pyrrole-2(1H)-carboxylate-4,4,6,6-$d_4$. tert-Butyl (3aR,5s,6aS)-5-(1,3-dioxoisoindolin-2-yl)hexahydrocyclopenta[c]pyrrole-2(1H)-carboxylate-4,4,6,6-$d_4$ (410 mg, 1.14 mmol, 1 eq.) was suspended in EtOH (12 mL) and hydrazine (0.18 mL, 5.69 mmol, 5 eq.) was added. The resulting solution was heated to 80° C. for 2 h, after which time the reaction mixture was cooled to r.t. and solids were removed by filtration and washed with $Et_2O$. The filtrate was concentrated under reduced pressure to give the title compound as a white solid which was dried under vacuum and used without additional purification (182 mg, 70%). ES-MS $[M+H]^+$=231.4.

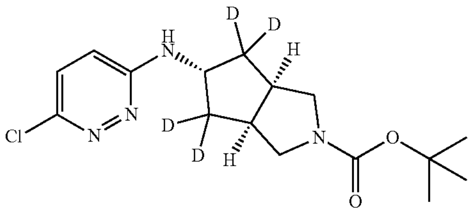 [SMILES: [2H]C1([2H])[C@H](Nc2ccc(Cl)nn2)C([2H])([2H])[C@H]2CN(C(=O)OC(C)(C)C)C[C@H]21]

tert-Butyl (3aR,5s,6aS)-5-((6-chloropyridazin-3-yl)amino)hexahydrocyclopenta[c]pyrrole-2(1H)-carboxylate-4,4,6,6-$d_4$. tert-Butyl (3aR,5s,6aS)-5-aminohexahydrocyclopenta[c]pyrrole-2(1H)-carboxylate-4,4,6,6-$d_4$ (182 mg, 0.79 mmol, 1 eq.) was dissolved in tert-butanol (2.5 mL) and 3,6-dichloropyridazine (354 mg, 2.38 mmol, 3 eq.) was added, followed by DIPEA (0.41 mL, 2.38 mmol, 3 eq.). The resulting solution was stirred at 150° C. under microwave irradiation for 2 h, after which time solvents were concentrated, and the crude residue was purified by column chromatography (3-100% EtOAc in hexanes) to give the title compound as a white solid (79.3 mg, 29%). ES-MS $[M+H]^+$ =287.4 (-t-butyl).

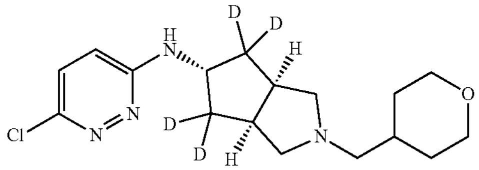 [SMILES: [2H]C1([2H])[C@H](Nc2ccc(Cl)nn2)C([2H])([2H])[C@H]2CN(CC3CCOCC3)C[C@H]21]

(3aR,5s,6aS)—N-(6-Chloropyridazin-3-yl)-2-((tetrahydro-2H-pyran-4-yl)methyl)octahydrocyclopenta[c]pyrrol-4,4,6,6-$d_4$-5-amine. tert-Butyl (3aR,5s,6aS)-5-((6-chloropyridazin-3-yl)amino)hexahydrocyclopenta[c]pyrrole-2(1H)-carboxylate-4,4,6,6-$d_4$ (79.3 mg, 0.23 mmol, 1 eq.) was dissolved in 1,4-dioxane (1 mL) and MeOH (0.5 mL) and 4M HCl in dioxanes solution (1.5 mL) was added. The resulting cloudy mixture was stirred at r.t. for 1 h, after which time solvents were concentrated, and the resulting white solid was dried under vacuum and used directly without further purification (64.6 mg, 100%). ES-MS $[M+H]^+$=243.2. The HCl salt (64.6 mg, 0.23 mmol, 1 eq.) and tetrahydro-2H-pyran-4-carbaldehyde (79.2 mg, 0.69 mmol, 3 eq.) were suspended in DCM (1 mL) and THE (1 mL), and sodium triacetoxyborohydride (147 mg, 0.69 mmol, 3 eq.) was added. The reaction mixture was stirred at r.t. for 1 h, after which time the reaction mixture was quenched with sat. $NaHCO_3$ solution. The aqueous layer was extracted with DCM, and combined organic extracts were filtered through a phase separator and concentrated. The crude residue was purified by RP-HPLC (5-35% MeCN in 0.1% TFA aqueous solution over 10 min). Fractions containing product were basified with sat. $NaHCO_3$ solution and extracted with DCM. The combined organic extracts were filtered through a phase separator and concentrated to give the title compound as a white solid (27.5 mg, 35% over 2 steps). $^1$H-NMR (400 MHz, $CDCl_3$) δ 7.15 (d, J=9.3 Hz, 1H), 6.62 (d, J=8.8 Hz, 1H), 4.84 (d, J=7.2 Hz, 1H), 4.23 (d, J=6.7 Hz, 1H), 3.96 (dd, J=10.9, 3.6 Hz, 2H), 3.38 (td, J=11.8, 1.9 Hz, 2H), 2.71-2.65 (m, 2H), 2.53-2.49 (m, 2H), 2.32 (dd, J=9.1, 2.9 Hz, 2H), 2.23 (d, J=6.8 Hz, 2H), 1.73-1.61 (m, 3H), 1.32-1.22 (m, 2H). ES-MS $[M+H]^+$ =341.4.

Example 9. (2,5-Difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone

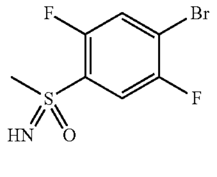

(4-Bromo-2,5-difluorophenyl)(imino)(methyl)-80 $^{6}$-sulfanone. To a solution of (4-bromo-2,5-difluorophenyl)(methyl)sulfane (1.00 g, 4.18 mmol, 1 eq) in MeOH (26 mL) was added ammonium carbonate (1.85 g, 19.2 mmol, 4.6 eq) and iodobenzene diacetate (4.04 g, 12.5 mmol, 3 eq). The reaction mixture was stirred at r.t. for 1 h, after which time sat. $NaHCO_3$ solution was added. The aqueous layer was extracted with DCM, and the combined organic extracts were dried with $Na_2SO_4$. The solvents were filtered and concentrated, and the crude residue was purified by column chromatography (0-100% Y, EtOAc in hexanes to 0-20% MeOH in DCM) to give the title compound as a clear film (1.12 g, 99%). $^1$H NMR (400 MHz, MeOD) δ 7.78-7.75 (m, 2H), 3.28 (s, 3H). ES-MS $[M+H]^+$=271.8, 273.8.

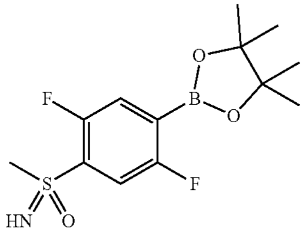

(2,5-Difluoro-4-(4,4,5,5-tetramethyl-1,3,2-dioxaborolan-2-yl)phenyl)(imino)(methyl)-$\lambda^6$-sulfanone. (4-Bromo-2,5-difluorophenyl)(imino(methyl)-$\lambda^6$-sulfanone (560 mg, 2.07 mmol, 1 eq), potassium acetate (610 mg, 6.22 mmol, 3 eq), bis(pinacolato)diboron (790 mg, 3.11 mmol, 1.5 eq) and Pd(dppf)$Cl_2$·DCM (170 mg, 0.21 mmol, 0.1 eq) were combined in a vial, which was sealed and placed under an inert atmosphere. 1,4-Dioxane (16 mL) was then added via syringe, and the resulting mixture was stirred at 120° C. under microwave irradiation for 1 h, after which time the reaction mixture was filtered through a plug of Celite® with DCM and EtOAc, and the solvents were concentrated to give a crude product. The crude product was dried under vacuum and used directly without further purification (658 mg, 100%).

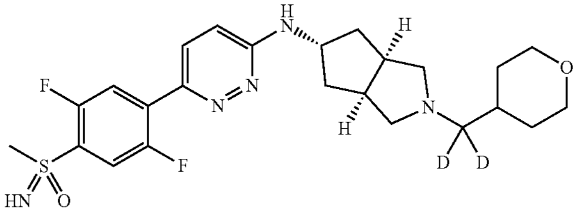 [SMILES: [2H]C([2H])(C1CCOCC1)N1C[C@H]2C[C@H](Nc3ccc(-c4cc(F)c(S(C)(=N)=O)cc4F)nn3)C[C@H]2C1]

(2,5-Difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone. (3aR,5s,6aS)—N-(6-Chloropyridazin-3-yl)-2-((tetrahydro-2H-pyran-4-yl)methyl-$d_2$)octahydrocyclopenta[c]pyrrol-5-amine (400 mg, 1.18 mmol, 1 eq), (2,5-difluoro-4-(4,4,5,5-tetramethyl-1,3,2-dioxaborolan-2-yl)phenyl)(imino)(methyl)-$\lambda^6$-sulfanone (936 mg, 2.95 mmol, 2.5 eq), potassium carbonate (497 mg, 3.54 mmol, 3 eq), and Brett-Phos-Pd-G3 (214 mg, 0.24 mmol, 0.2 eq) were combined in a vial, which was sealed and placed under an inert atmosphere. 5:1 1,4-Dioxane/$H_2O$ solution (9 mL total, degassed under vacuum) was then added via syringe. The resulting reaction mixture was stirred at 100° C. for 3 h, after which time the reaction mixture was cooled to r.t. and diluted with sat. $NaHCO_3$ and DCM. The combined organic extracts were dried over $Na_2SO_4$, and the solvents were filtered and concentrated. The crude residue was purified by RP-HPLC (15-95% MeCN in 0.05% aqueous $NH_4OH$ solution over 20 min). The fractions containing product were concentrated to give the title compound as a white solid (148 mg, 25%). $^1$H NMR (400 MHz, MeOD) δ 7.92 (dd, J=10.6, 5.8 Hz, 1H), 7.78 (dd, J=10.1, 5.7 Hz, 1H), 7.73 (dd, J=9.5, 2.3 Hz, 1H), 6.92 (d, J=9.5 Hz, 1H), 4.57-4.50 (m, 1H), 3.94 (dd, J=11.2, 4.2, 2H), 3-43 (td, J=11.8, 2.0 Hz, 2H), 3.32 (s, 3H), 2.83-7.73 (m, 4H), 2.30-2.20 (m, 2H), 1.99-1.94 (m, 2H), 1.80-1.71 (m, 5H), 1.32-1.22 (m, 2H). ES-MS $[M+H]^+$ =494.1.

Example 10. (2,5-Difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)((methyl-$d_3$)imino)-$\lambda^6$-sulfanone

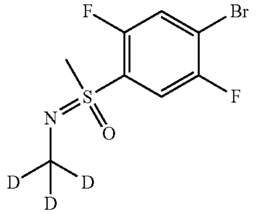 [SMILES: [2H]C([2H])([2H])N=S(C)(=O)c1cc(F)c(Br)cc1F]

(4-Bromo-2,5-difluorophenyl)(methyl)((methyl-$d_3$)imino)-$\lambda^6$-sulfanone. To a solution of (4-bromo-2,5-difluorophenyl)(imino)(methyl)-$\lambda^6$-sulfanone (83 mg, 0.31 mmol, 1 eq) in DMF (2 mL) was added NaH (25 mg, 0.62 mmol, 2 eq, 60% dispersion in mineral oil). The resulting reaction mixture was stirred at r.t. for 10 min under an inert atmosphere, after which time iodomethane-$d_3$ (0.038 mL, 0.62 mmol, 2 eq) was added dropwise. The resulting reaction mixture was stirred at r.t. under an inert atmosphere for 1 h, after which time the reaction was quenched with sat. $NaHCO_3$. The aqueous layer was extracted with DCM, and the combined organic extracts were filtered through a phase separator and concentrated. The crude residue was purified by column chromatography (3-100% EtOAc in hexanes) to give the title compound as a white solid (64 mg, 72%). $^1$H NMR (400 MHz, $CDCl_3$) δ 7.71 (dd, J=7.3, 5.8 Hz, 1H), 7.48 (dd, J=8.3, 5.1 Hz, 1H), 3.23 (s, 3H). ES-MS $[M+H]^+$=288.9, 290.7.

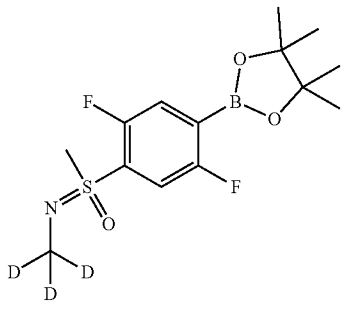 [SMILES: [2H]C([2H])([2H])N=S(C)(=O)c1cc(F)c(B2OC(C)(C)C(C)(C)O2)cc1F]

(2,5-Difluoro-4-(4,4,5,5-tetramethyl-1,3,2-dioxaborolan-2-yl)phenyl)(methyl)((methyl-$d_3$)imino)-$\lambda^6$-sulfanone. (4-Bromo-2,5-difluorophenyl)(methyl)((methyl-$d_3$)imino)-$\lambda^6$-sulfanone (64 mg, 0.22 mmol, 1 eq), potassium acetate (65 mg, 0.66 mmol, 3 eq), bis(pinacolato)diboron (84 mg, 0.33 mmol, 1.5 eq) and Pd(dppf)$Cl_2$·DCM (18 mg, 0.022 mmol, 0.1 eq) were combined in a vial, which was sealed and placed under an inert atmosphere. 1,4-Dioxane (3 mL) was then added via syringe, and the resulting mixture was stirred at 120° C. under microwave irradiation for 1 h, after which time the reaction mixture was filtered through a plug of Celite® with DCM and EtOAc, and the solvents were concentrated to give a crude product, which was dried under vacuum and used directly without further purification (658 mg, 100%).

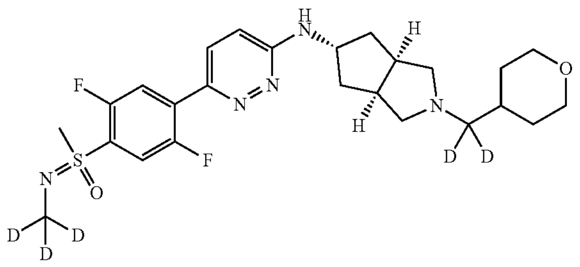 [SMILES: [2H]C([2H])([2H])N=S(C)(=O)c1cc(F)c(-c2ccc(N[C@H]3C[C@@H]4CN(C([2H])([2H])C5CCOCC5)C[C@@H]4C3)nn2)cc1F]

(2,5-Difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)((methyl-$d_3$)imino)-$\lambda^6$-sulfanone. (3aR,5s,6aS)—N-(6-Chloropyridazin-3-yl)-2-((tetrahydro-2H-pyran-4-yl)methyl-$d_2$)octahydrocyclopenta[c]pyrrol-5-amine (20 mg, 0.059 mmol, 1 eq), (2,5-difluoro-4-(4,4,5,5-tetramethyl-1,3,2-dioxaborolan-2-yl)phenyl)(methyl)((methyl-$d_2$)imino)-$\lambda^6$-sulfanone (39 mg, 0.12 mmol, 2 eq), potassium carbonate (25 mg, 0.18 mmol, 3 eq), and BrettPhos-Pd-G3 (5.4 mg, 0.006 mmol, 0.1 eq) were combined in a vial, which was sealed and placed under an inert atmosphere. 5:1 1,4-Dioxane/$H_2O$ solution (1 mL total, degassed under vacuum) was then added via syringe. The resulting reaction mixture was stirred at 100° C. for 2 h, after which time the reaction mixture was cooled to r.t. and diluted with $H_2O$ and DCM. The aqueous layer was extracted with DCM, and the combined organic extracts were filtered through a phase separator and concentrated. The crude residue was purified by RP-HPLC (2-32% MeCN in 0.1% TFA aqueous solution over 5 min). The fractions containing product were basified with sat. $NaHCO_3$, and extracted with DCM. The combined organic extracts were filtered through a phase separator and concentrated to give the title compound as a white solid (6.7 mg, 22%). $^1$H NMR (400 MHz, MeOD) δ 7.94 (dd, J=10.6, 5.7 Hz, 1H), 7.78-7.70 (m, 2H), 6.92 (d, J=9.5 Hz, 1H), 4.57-4.50 (m, 1H), 3.94 (dd, J=11-4, 3.3 Hz, 2H), 3-43 (td, J=11.9, 2.0 Hz, 2H), 3.34 (s, 3H), 2.83-2.75 (m, 4H), 2.28-2.24 (m, 2H), 1.99-1.94 (m, 2H), 1.80-1.70 (m, 5H), 1.32-1.22 (m, 2H). ES-MS $[M+H]^+$=511.2.

Example 11. N-((2,5-Difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)(oxo)-$\lambda^6$-sulfaneylidene)acetamide

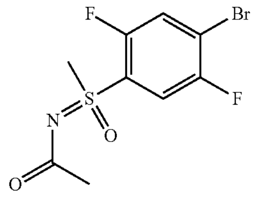 [SMILES: CC(=O)N=S(C)(=O)c1cc(F)c(Br)cc1F]

N-((4-Bromo-2,5-difluorophenyl)(methyl)(oxo)-$\lambda^6$-sulfaneylidene)acetamide.

To a solution of (4-bromo-2,5-difluorophenyl)(imino)(methyl)-$\lambda^6$-sulfanone (74 mg, 0.27 mmol, 1 eq) in DCM (2 mL) was added triethylamine (0.076 mL, 0.55 mmol, 2 eq), followed by acetyl chloride (0.039 mL, 0.55 mmol, 2 eq). The resulting reaction mixture was stirred at r.t. under an inert atmosphere for 1 h, after which time the reaction was quenched with sat. $NaHCO_3$. The aqueous layer was extracted with DCM, and the combined organic extracts were filtered through a phase separator and concentrated, and the crude residue was purified by column chromatography (3-100% EtOAc in hexanes) to give the title compound as a colorless oil (85 mg, 100%). $^1$H NMR (400 MHz, $CDCl_3$) δ 7.82 (dd, J=7.1, 5.9 Hz, 1H), 7.50 (dd, J=8.7, 5.0 Hz, 1H), 3.38 (s, 3H), 2.10 (s, 3H). ES-MS $[M+H]^+$=313.9, 315.9.

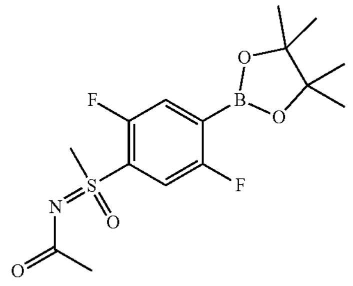 [SMILES: CC(=O)N=S(C)(=O)c1cc(F)c(B2OC(C)(C)C(C)(C)O2)cc1F]

N-((2,5-Difluoro-4-(4,4,5,5-tetramethyl-1,3,2-dioxaborolan-2-yl)phenyl)(methyl)(oxo)-$\lambda^6$-sulfaneylidene)acetamide. N-((4-Bromo-2,5-difluorophenyl)(methyl)(oxo)-$\lambda^6$-sulfaneylidene)acetamide (85 mg, 0.27 mmol, 1 eq), potassium acetate (80 mg, 0.82 mmol, 3 eq), bis(pinacolato)diboron (104 mg, 0.41 mmol, 1.5 eq) and Pd(dppf)$Cl_2$-DCM (22 mg, 0.027 mmol, 0.1 eq) were combined in a vial, which was sealed and placed under an inert atmosphere. 1,4-Dioxane (3 mL) was then added via syringe, and the resulting mixture was stirred at 120° C. under microwave irradiation for 1 h, after which time the reaction mixture was filtered through a plug of Celite® with DCM and EtOAc, and the solvents were concentrated to give a crude product, which was dried under vacuum and used directly without further purification (98 mg, 100%). ES-MS $[M+H]^+=277.9$ (mass of boronic acid is observed).

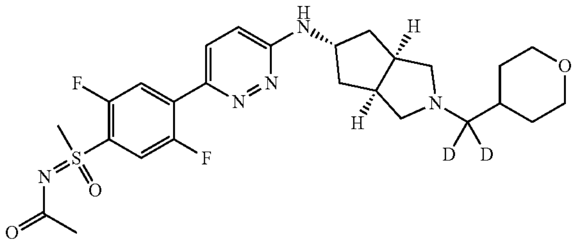 [SMILES: [2H]C([2H])(C1CCOCC1)N1C[C@H]2C[C@H](Nc3ccc(-c4cc(F)c(S(C)(=O)=NC(C)=O)cc4F)nn3)C[C@H]2C1]

N-((2,5-Difluoro-4-(6-(((3aR,5s,6aS)-2-((tetrahydro-2H-pyran-4-yl)methyl-$d_2$)octahydrocyclopenta[c]pyrrol-5-yl) amino)pyridazin-3-yl)phenyl)(methyl)(oxo)-$\lambda^6$-sulfaneylidene)acetamide. (3aR,5s,6aS)—N-(6-Chloropyridazin-3-yl)-2-((tetrahydro-2H-pyran-4-yl)methyl-$d_2$) octahydrocyclopenta[c]pyrrol-5-amine (20 mg, 0.059 mmol, 1 eq), N-((2,5-difluoro-4-(4,4,5,5-tetramethyl-1,3,2-dioxaborolan-2-yl)phenyl)(methyl)(oxo)-$\lambda^6$-sulfaneylidene)acetamide (42 mg, 0.12 mmol, 2 eq), potassium carbonate (25 mg, 0.18 mmol, 3 eq), and BrettPhos-Pd-G3 (5.4 mg, 0.006 mmol, 0.1 eq) were combined in a vial, which was sealed and placed under an inert atmosphere. 5:1 1,4-Dioxane/$H_2O$ solution (1 mL total, degassed under vacuum) was then added via syringe. The resulting reaction mixture was stirred at 100° C. for 2 h, after which time the reaction mixture was cooled to r.t. and diluted with $H_2O$ and DCM. The aqueous layer was extracted with DCM, and the combined organic extracts were filtered through a phase separator and concentrated. The crude residue was purified by RP-HPLC (15-55% MeCN in 0.05% $NH_4OH$ aqueous solution over 5 min). The fractions containing product were concentrated to give the title compound as a white solid (2.8 mg, 9%). $^1H$ NMR (400 MHz, MeOD) δ 7.97 (dd, J=10.9, 5.7 Hz, 1H), 7.85 (dd, =10.0, 5.6 Hz, 1H), 7.75 (dd, =9.5, 2.3 Hz, 1H), 6.92 (d, J=9.5 Hz, 1H), 4.57-4.50 (m, 1H), 3.94 (dd, J=11-4, 3.1 Hz, 2H), 3-49 (s, 3H), 3-43 (td, J=11.9, 2.0 Hz, 2H), 2.82-2.74 (m, 4H), 2.28-2.22 (m, 2H), 2.06 (s, 3H), 2.99-1.94 (m, 2H), 1.80-1.71 (m, 5H), 1.32-1.22 (m, 2H). ES-MS [M+H]=536.1.

Example 12. (2,5-Difluoro-4-(6-(((3aR,5s,6aS)-2-((tetrahydro-2H-pyran-4-yl)methyl)octahydrocyclopenta[c]pyrrol-5-yl)amino)pyridazin-3-yl)phenyl)(imino)(methyl)-1'-sulfanone

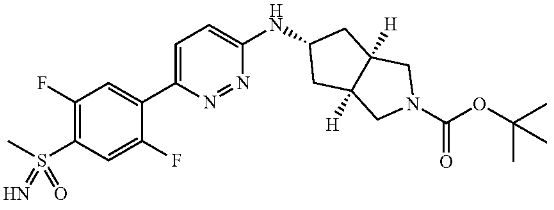 [SMILES: CC(C)(C)OC(=O)N1C[C@H]2C[C@H](Nc3ccc(-c4cc(F)c(S(C)(=N)=O)cc4F)nn3)C[C@H]2C1]

tert-Butyl (3aR,5s,6aS)-5-((6-(2,5-difluoro-4-(S-methylsulfonimidoyl)phenyl)pyridazin-3-yl)amino)hexahydrocyclopenta[c]pyrrole-2(1H)-carboxylate. tert-Butyl (3aR,5s,6aS)-5-((6-chloropyridazin-3-yl)amino) hexahydrocyclopenta[c]pyrrole-2(1H)-carboxylate (800 mg, 2.36 mmol, 1 eq), (2,5-difluoro-4-(4,4,5,5-tetramethyl-1,3,2-dioxaborolan-2-yl)phenyl)(imino)(methyl)-$\lambda^6$-sulfanone (1-30 g, 4.11 mmol, 1.74 eq), potassium carbonate (993 mg, 7.08 mmol, 3 eq), and BrettPhos-Pd-G3 (214 mg, 0.24 mmol, 0.1 eq) were combined in a vial, which was sealed and placed under an inert atmosphere. 5:1 1,4-Dioxane/$H_2O$ solution (15 mL total, degassed under vacuum) was then added via syringe. The resulting reaction mixture was stirred at 100° C. under an inert atmosphere for 2 h, after which time the reaction mixture was cooled to r.t. and diluted with DCM and $H_2O$. The aqueous layer was extracted with DCM, and the combined organic extracts were dried with $MgSO_4$. The solvents were filtered and concentrated, and the crude residue was purified by column chromatography (3-100% EtOAc in hexanes to 0-10% MeOH in DCM) to give the title compound as a tan solid (373 mg, 32%). $^1H$ NMR (400 MHz, MeOD) δ 7.92 (dd, J=10.6, 5.7 Hz, 1H), 7.78 (dd, J=10.1, 5.8 Hz, 1H), 7.74 (dd, J=9.5, 2.3 Hz, 1H), 6.93 (d, J=9.5 Hz, 1H), 4.59-4.52 (m, 1H), 3.58 (dd, J=11.0, 7.9 Hz, 2H), 3.32 (s, 3H), 3.23 (dd, J=11-4, 4.1 Hz, 2H), 2.93-2.85 (m, 2H), 2.06-1.98 (m, 2H), 1.96-1.87 (m, 2H), 1-47 (s, 9H). ES-MS $[M+H]^+=438.1$ (-t-butyl).

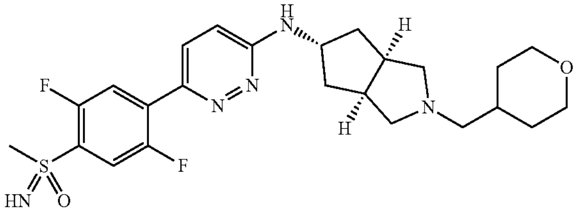 [SMILES: CS(=N)(=O)c1cc(F)c(-c2ccc(N[C@H]3C[C@@H]4CN(CC5CCOCC5)C[C@@H]4C3)nn2)cc1F]

(2,5-Difluoro-4-(6-(((3aR,5s,6aS)-2-((tetrahydro-2H-pyran-4-yl)methyl)octahydrocyclopenta[c]pyrrol-5-yl) amino)pyridazin-3-yl)phenyl)(imino)(methyl)-$\lambda^6$-sulfanone. To a solution of tert-butyl (3aR,5s,6aS)-5-((6-(2,5-difluoro-4-(S-methylsulfonimidoyl)phenyl)pyridazin-3-yl) amino)hexahydrocyclopenta[c]pyrrole-2(1H)-carboxylate (371 mg, 0.75 mmol, 1 eq) in 1,4-dioxane (3 mL) and MeOH (1 mL) was added 4M HCl in dioxanes solution (2 mL). The resulting reaction mixture was stirred at r.t. for 1 h, after which time the solvents were concentrated to give the HCl amine as a tan solid, which was dried under vacuum and used directly without additional purification (324 mg, 100/%). ES-MS $[M+H]^+=394.2$. To the HCl amine (20 mg, 0.047 mmol, 1 eq) in DCM (0.5 mL) and THF (0.5 mL) was added tetrahydro-2H-pyran-4-carbaldehyde (16 mg, 0.14 mmol, 3 eq) and sodium triacetoxyborohydride (30 mg, 0.14 mmol, 3 eq). The resulting reaction mixture was stirred at r.t. for 1 h, after which time sat. $NaHCO_3$ solution was added, and the aqueous layer was extracted with DCM. The combined organic extracts were filtered through a phase separator and concentrated, and the crude residue was purified by RP-HPLC (2-32% MeCN in 0.1% TFA aqueous solution over 5 min). The fractions containing product were basified with sat. $NaHCO_3$, and extracted with DCM. The combined organic extracts were filtered through a phase separator and concentrated to give the title compound as a colorless oil (4.2 mg, 18%). $^1H$ NMR (400 MHz, MeOD) δ 7.92 (dd, J=10.6, 5.8 Hz, 1H), 7.78 (dd, J=10.1, 5.7 Hz, 1H), 7.73 (dd, J=9.5, 2.3 Hz, 1H), 6.92 (d, J=9.5 Hz, 1H), 4.57-4.50 (m, 1H), 3.94 (dd, J=11.7, 3.6 Hz, 2H), 3-43 (td, J=11.8, 1.9 Hz, 2H), 3.32 (s, 3H), 2.84-2.74 (m, 4H), 2.33 (d, J=6.8 Hz, 2H), 2.27 (dd, J=8.1, 3.5 Hz, 2H), 1.99-1.94 (m, 2H), 1.82-1.69 (m, 5H), 1.32-1.22 (m, 2H). ES-MS [M+H]=492.2.

Example 13. (2,5-Difluoro-4-(6-(((3aR,5s,6aS)-2-((2,2,6,6-tetramethyltetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone

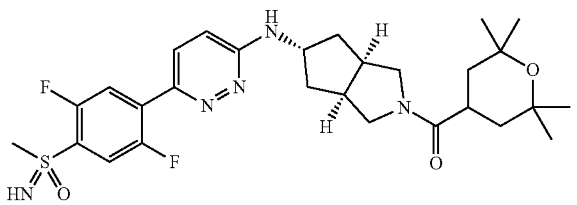

(2,5-Difluoro-4-(6-(((3aR,5s,6aS)-2-(2,2,6,6-tetramethyltetrahydro-2H-pyran-4-carbonyl)octahydrocyclopenta[c]pyrrol-5-yl)amino)pyridazin-3-yl)phenyl)(imino)(methyl)-$\lambda^6$-sulfanone. To a solution of tert-butyl (3aR,5s,6aS)-5-((6-(2,5-difluoro-4-(S-methylsulfonimidoyl)phenyl)pyridazin-3-yl)amino)hexahydrocyclopenta[c]pyrrole-2(1H)-carboxylate (371 mg, 0.75 mmol, 1 eq) in 1,4-dioxane (3 mL) and MeOH (1 mL) was added 4M HCl in dioxanes solution (2 mL). The resulting reaction mixture was stirred at r.t. for 1 h, after which time the solvents were concentrated to give the HCl salt of the amine as a tan solid, which was dried under vacuum and used directly without additional purification (324 mg, 100%). ES-MS $[M+H]^+$=394.2. To the HCl salt of the amine (35 mg, 0.081 mmol, 1 eq) and 2,2,6,6-tetramethyltetrahydro-2H-pyran-4-carboxylic acid (18 mg, 0.10 mmol, 1.2 eq) in DMF (1 mL) was added DIPEA (0.043 mL, 0.24 mmol, 3 eq), followed by HATU (46 mg, 0.12 mmol, 1.5 eq). The resulting solution was stirred at r.t. for 1 h, after which time the reaction mixture was purified directly by RP-HPLC (18-58% MeCN in 0.05% aqueous $NH_4OH$ solution over 5 min). The fractions containing product were concentrated to give the title compound as a tan solid (15 mg, 34%). $^1H$ NMR (400 MHz, MeOD) δ 7.92 (dd, J=10.6, 5.8 Hz, 1H), 7.77 (dd, J=10.1, 5.7 Hz, 11H), 7.74 (dd, J=9.7, 2.2 Hz, 1H), 6.93 (d, J=9.4 Hz, 1H), 4.60-4.54 (m, 1H), 3.89 (dd, J=11.0, 8.4 Hz, 1H), 3-71 (dd, J=12.6, 8.5 Hz, 1H), 3.52 (dd, J=11.0, 5.1 Hz, 1H), 3.38 (dd, J=12.6, 4.7 Hz, 1H), 3.32 (s, 3H), 3.11-2.99 (m, 2H), 2.96-2.87 (m, 1H), 2.16-2.10 (m, 1H), 2.06-2.00 (m, 1H), 1.98-1.89 (m, 2H), 1.71 (ddd, J=13.2, 3.3, 2.0 Hz, 1H), 1.65 (ddd, J=13.1, 3.3, 2.0 Hz, 1H), 1.49 (q, J=12.9 Hz, 2H), 1.33 (d, J=7.2 Hz, 6H), 1.22 (d, J=6.0 Hz, 6H). ES-MS [M+H]=562.3.

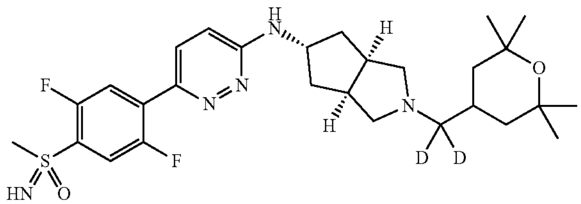

(2,5-Difluoro-4-(6-(((3aR,5s,6aS)-2-((2,2,6,6-tetramethyltetrahydro-2H-pyran-4-yl)methyl-$d_2$)octahydrocyclopenta[c]pyrrol-5-yl)amino)pyridazin-3-yl)phenyl)(imino)(methyl)-1'-sulfanone. To a solution of (2,5-difluoro-4-(6-(((3aR,5s,6aS)-2-(2,2,6,6-tetramethyltetrahydro-2H-pyran-4-carbonyl)octahydrocyclopenta[c]pyrrol-5-yl)amino)pyridazin-3-yl)phenyl)(imino)(methyl)-$\lambda^6$-sulfanone (15 mg, 0.027 mmol, 1 eq) in THF (1 mL) was added lithium aluminum deuteride (5.2 mg, 0.14 mmol, 5 eq). The resulting reaction mixture was stirred at r.t. for 15 min, after which time sat. $NaHCO_3$ solution was added. The aqueous layer was extracted with DCM, and the combined organic extracts were filtered through a phase separator and concentrated. The crude residue was purified by RP-HPLC (2-32% MeCN in 0.1% TFA aqueous solution over 5 min). The fractions containing product were basified with sat. $NaHCO_3$, and extracted with DCM. The combined organic extracts were filtered through a phase separator and concentrated to give the title compound as a colorless oil (5.9 mg, 39%). $^1H$ NMR (400 MHz, MeOD) δ 7.93 (dd, J=10.6, 5.8 Hz, 1H), 7.78 (dd, J=10.1, 5.7 Hz, 1H), 7.73 (dd, J=9.5, 2.3 Hz, 1H), 6.92 (d, J=9.5 Hz, 1H), 4.58-4.51 (m, 1H), 3.33 (s, 3H), 2.89 (t, J=7.8 Hz, 2H), 2.83-2.76 (m, 2H), 2.26 (dd, J=9.5, 4.6 Hz, 2H), 2.10 (tt, J=12.2, 3.3 Hz, 1H), 1.97 (ddd, J=12.8, 5.9, 2.2 Hz, 2H), 1.79-1.72 (m, 4H), 1.29 (s, 6H), 1.19 (s, 6H), 0.98 (t, J=12.7 Hz, 2H). ES-MS $[M+H]^+$=550.2.

Example 14. Methyl(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)((trifluoromethyl)imino)-$\lambda^6$-sulfanone

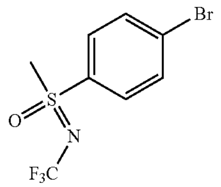

(4-Bromophenyl)(methyl)((trifluoromethyl)imino)-$\lambda^6$-sulfanone. (4-Bromophenyl)(imino)(methyl)-$\lambda^6$-sulfanone (75 mg, 0.32 mmol, 1 eq), 1,10-phenanthroline (23.1 mg, 0.13 mmol, 0.4 eq), and silver (I) carbonate were sealed in a vial and placed under an inert atmosphere. Trimethyl(trifluoromethyl)silane (0.24 ml, 1.60 mmol, 5 eq) and 1,4-dioxane (3 mL) were added via syringe and the mixture was degassed then placed under an atmosphere of 02 (balloon). After 18 h at 60° C., the solvents were concentrated and the resulting crude residue was suspended in $H_2O$, extracted in DCM, and concentrated. The crude residue was purified by column chromatography (3-50% EtOAc in hexanes) to yield the title compound as an off white solid (46.1 mg, 48%). $^1H$ NMR (400 MHz, $CDCl_3$) δ 7.88-7.84 (m, 2H), 7.78-7.74 (m, 2H), 3.23 (s, 3H). ES-MS $[M+H]^+$=303.8.

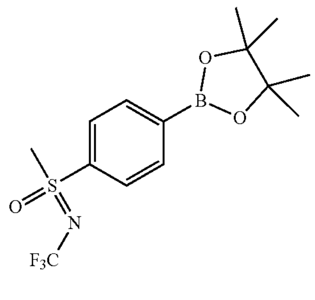 [SMILES: CC1(C)OB(c2ccc(S(C)(=O)=NC(F)(F)F)cc2)OC1(C)C]

Methyl(4-(4,4,5,5-tetramethyl-1,3,2-dioxaborolan-2-yl)phenyl)((trifluoromethyl)imino)-λ$^6$-sulfanone. (4-Bromophenyl)(methyl)(trifluoromethyl)imino)-λ$^6$-sulfanone (46.0 mg, 0.15 mmol, 1 eq), Pd(dppf)$Cl_2$-DCM (12.5 mg, 0.015 mmol, 0.1 eq), bis(pinacolato)diboron (58.0 mg, 0.23 mmol, 1.5 eq), and potassium acetate (44.8 mg, 0.46 mmol, 3 eq) were sealed in a microwave vial. 1,4-Dioxane (1 mL) was added via syringe and the reaction mixture was stirred under vacuum for 3 min, then placed under an inert atmosphere. The reaction was subjected to microwave irradiation at 120° C. for 1 h, then syringe-filtered and concentrated. The crude residue was purified by column chromatography (3-80/a EtOAc in hexanes) to yield the title compound as a light yellow solid (23.3 mg, 44%). ES-MS [M+H−$C_6H_2$]$^+$=268.0 (mass of boronic acid is observed).

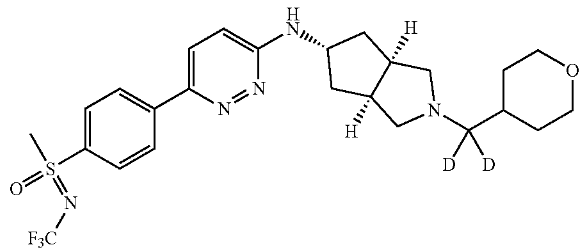 [SMILES: [2H]C([2H])(C1CCOCC1)N1C[C@H]2C[C@H](Nc3ccc(-c4ccc(S(C)(=O)=NC(F)(F)F)cc4)nn3)C[C@H]2C1]

Methyl(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)((trifluoromethyl)imino)-λ$^6$-sulfanone. (3aR,5s,6aS)—N-(6-Chloropyridazin-3-yl)-2-((tetrahydro-2H-pyran-4-yl)methyl-$d_2$)octahydrocyclopenta[c]pyrrol-5-amine (20 mg, 0.059 mmol, 1 eq), potassium carbonate (24.8 mg, 0.18 mmol, 3 eq), methyl(4-(4,4,5,5-tetramethyl-1,3,2-dioxaborolan-2-yl)phenyl)((trifluoromethyl)imino)-λ$^6$-sulfanone (23.3 mg, 0.066 mmol, 1.1 eq) and BrettPhos-Pd-G3 (8.0 mg, 0.0089 mmol, 0.15 eq) were sealed in a vial and placed under an inert atmosphere. 5:1 1,4-Dioxanes/$H_2O$ solution (1.2 mL, degassed under vacuum) was added via syringe and the resulting mixture was heated to 100° C. After 2 h, the reaction was cooled to r.t., diluted with $H_2O$ and extracted in DCM. The concentrated crude residue was purified by RP-HPLC (3-35% MeCN in 0.1% TFA aqueous solution over 7 min). The fractions containing product were basified with sat. $NaHCO_3$ solution and extracted in DCM to yield the title compound as a colorless glass. $^1$H NMR (400 MHz, MeOD) δ 8.25-8.21 (m, 2H), 8.12-8.08 (m, 2H), 7.85 (d, J=9.5 Hz, 1H), 6.95 (d, J=9.5 Hz, 1H), 4.58-4.49 (m, 1H), 3.94 (dd, J=11.5, 5.1 Hz, 2H), 3.43 (td, J=11.9, 2.4 Hz, 2H), 3.38 (s, 3H), 2.87-2.78 (m, 2H), 2.81-2.74 (m, 2H), 2.26 (dd, J=8.5, 3.7 Hz, 2H), 1.97 (dd, J=12.7, 5.8 Hz, 2H), 1.81-1.70 (m, 5H), 1.33-1.21 (m, 2H). ES-MS [M+H]$^+$=526.1.

Example 15. Representative Synthetic Procedures

Representative Synthesis 1

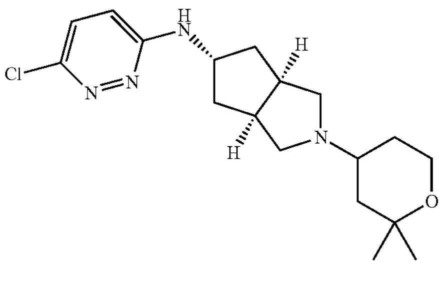 [SMILES: CC1(C)CC(N2C[C@H]3C[C@H](Nc4ccc(Cl)nn4)C[C@H]3C2)CCO1]

(3aR,5s,6aS)—N-(6-Chloropyridazin-3-yl)-2-(2,2-dimethyltetrahydro-2H-pyran-4-yl)octahydrocyclopenta[c]pyrrol-5-amine. (3aR,5s,6aS)—N-(6-Chloropyridazin-3-yl)octahydrocyclopenta[c]pyrrol-5-amine dihydrochloride (300 mg, 0.96 mmol) was dissolved in DCM (3 mL), THF (3 mL) and AcOH (0.5 mL), and 2,2-dimethyltetrahydro-4H-pyran-4-one (370 mg, 2.89 mmol) was added, followed by sodium triacetoxyborohydride (612 mg, 2.89 mmol). The resulting solution was stirred at 40° C. for 1 h, after which time the reaction was quenched with sat. $NaHCO_3$, and extracted with 3:1 chloroform/IPA (v/v). The combined organic extracts were filtered through a phase separator and concentrated. The crude residue was taken up in DMSO and purified directly by RP-HPLC (5-35% MeCN in 0.1% TFA aqueous solution over 20 min). The fractions containing product were basified with sat. $NaHCO_3$, and extracted with 3:1 chloroform/IPA (v/v). The combined organic extracts were dried with $MgSO_4$, and the solvents were filtered and concentrated under reduced pressure to afford the title compound as a white solid (138 mg, 41%). ES-MS [M+H]$^+$=351.3.

Representative Synthesis 2. (3aR,5s,6aS)—N-(6-(2-Chloro-5-fluorophenyl)pyridazin-3-yl)-2-(1-(tetrahydro-2H-pyran-4-yl)cyclopropyl)octahydrocyclopenta[c]pyrrol-5-amine

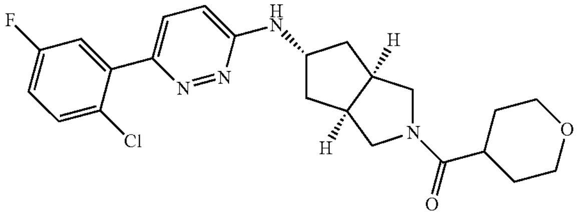 [SMILES: O=C(C1CCOCC1)N1C[C@H]2C[C@H](Nc3ccc(-c4cc(F)ccc4Cl)nn3)C[C@H]2C1]

((3aR,5s,6aS)-5-((6-(2-Chloro-5-fluorophenyl)pyridazin-3-yl)amino)hexahydrocyclopenta[c]pyrrol-2(1H)-yl)(tetrahydro-2H-pyran-4-yl)methanone.

(3aR,5s,6aS)—N-(6-(2-Chloro-5-fluorophenyl)pyridazin-3-yl)octahydrocyclopenta[c]pyrrol-5-amine hydrochloride (53.4 mg, 0.14 mmol) and 4-oxanoic acid (22.6 mg, 0.17 mmol) were dissolved in DMF (1 mL), and DIPEA (0.076 mL, 0.43 mmol) was added, followed by HATU (82.5 mg, 0.22 mmol). The resulting solution was stirred at r.t. for 1 h, after which time the reaction mixture was purified directly by RP-HPLC (25-65% MeCN in 0.05% $NH_4OH$ aqueous solution over 10 min). Fractions containing product were concentrated to afford the title compound as a colorless oil (39 mg, 61%). ES-MS $[M+H]^+$ =445.0.

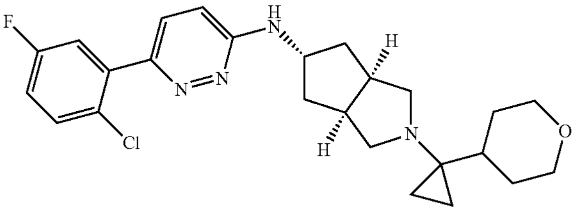 [SMILES: Fc1ccc(Cl)c(-c2ccc(N[C@H]3C[C@@H]4CN(C5(C6CCOCC6)CC5)C[C@@H]4C3)nn2)c1]

(3aR,5s,6aS)—N-(6-(2-Chloro-5-fluorophenyl) pyridazin-3-y)-2-(1-(tetrahydro-2H-pyran-4-yl)cyclopropyl)octahydrocyclopenta[c]pyrrol-5-amine. To a solution of ethylmagnesium bromide (0.062 mL, 0.062 mmol, 1.0 M solution) in THF (0.2 mL) was added titanium(IV) isopropoxide (0.008 mL, 0.026 mmol) in 0.1 mL THF at −78° C. The resulting solution was stirred at −78° C. for 30 min under an inert atmosphere, after which time ((3aR,5s,6aS)-5-((6-(2-chloro-5-fluorophenyl)pyridazin-3 yl)amino)hexahydrocyclopenta[c]pyrrol-2(1H)-yl)(tetrahydro-2H-pyran-4-yl)methanone (11 mg, 0.025 mmol (in 0.3 mL THF)) was added dropwise. The resulting solution was warmed to r.t. and then stirred at reflux for 1 h, after which time the reaction mixture was cooled to 0° C. and another 2.5 eq ethylmagnesium bromide (1.0 M solution, 5 eq total) and 1.05 eq titanium(IV) isopropoxide (in 0.1 mL THF, 2.1 eq total) were added dropwise. The resulting brown solution was warmed to r.t. and stirred for 1 h, after which time the reaction was quenched with $H_2O$ and diluted with 3:1 chloroform/IPA (v/v). The aqueous layer was extracted with 3:1 chloroform/IPA (v/v), and combined organic extracts were filtered through a phase separator and concentrated. The crude residue was purified by RP-HPLC (65-95% MeCN in 0.05% $NH_4OH$ aqueous solution over 5 min), and the fractions containing product were concentrated to afford the title compound as a tan solid (1.1 mg, 10%). $^1H$-NMR (400 MHz, MeOD) δ 7.58 (d, J=9.4 Hz, 1H), 7.56 (dd, J=8.8, 5.0 Hz, 1H), 7.37 (dd, J=9.0, 3.1 Hz, 1H), 7.24-7.19 (m, 1H), 6.94 (d, =9.4 Hz, 1H), 4.54-4.48 (m, 1H), 3.99-3.95 (m, 2H), 3.45-3.39 (m, 2H), 2.67-2.64 (m, 4H), 2.46-2.42 (m, 2H), 1.94-1.83 (m, 4H), 1.63-1.49 (m, 5H), 0.70 (dd, J=6.5, 5.0 Hz, 2H), 0.44 (dd, J=6.2, 4.8 Hz, 2H). ES-MS [M+H]=457.4.

Representative Synthesis 3. (3aR,5s,6aS)—N-(6-(2-Chloro-5-fluorophenyl)pyridazin-3-yl)-2-(3-methoxypropyl)octahydrocyclopenta[c]pyrrol-5-amine

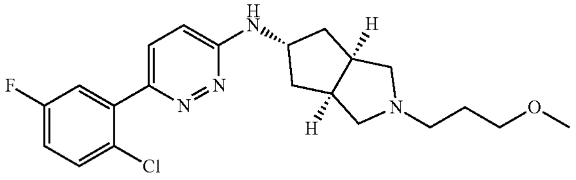 [SMILES: COCCCN1C[C@H]2C[C@H](Nc3ccc(-c4cc(F)ccc4Cl)nn3)C[C@H]2C1]

(3aR,5s,6aS)—N-(6-(2-Chloro-5-fluorophenyl) pyridazin-3-yl)octahydrocyclopenta[c]pyrrol-5-amine dihydrochloride (20.3 mg, 0.050 mmol) was dissolved in DMF (1 mL) and cesium carbonate (49 mg, 0.15 mmol) was added, followed by 1-bromo-3-methoxypropane (38 mg, 0.25 mmol). The resulting solution was stirred at 70° C. overnight, after which time the solids were removed via syringe filtration, and the crude residue was purified by RP-HPLC (5-35% MeCN in 0.1% TFA aqueous solution over 5 min). Fractions containing product were basified with sat. $NaHCO_3$, and extracted with 3:1 chloroform/IPA (v/v). The combined organic extracts were filtered through a phase separator and concentrated to afford the title compound as a white solid (3.2 mg, 16%). $^1H$-NMR (400 MHz, MeOD) δ 7.46 (d, J=9.3 Hz, 1H), 7.44 (dd, J=8.8, 5.0 Hz, 1H), 7.25 (dd, J=9.0, 3.1 Hz, 1H), 7.12-7.07 (m, 1H), 6.82 (d, J=9.4 Hz, 1H), 4.45-4.38 (m, 1H), 3.35 (t, J=6.2 Hz, 2H), 3.23 (s, 3H), 2.92-2.87 (m, 2H), 2.74-2.69 (m, 2H), 2.49-2.45 (m, 2H), 2.17-2.14 (m, 2H), 1.91-1.85 (m, 2H), 1.74-1.61 (m, 4H). ES-MS $[M+H]^+$=405.4.

Representative Synthesis 4. 1-((3aR,5s,6aS)-5-((6-(2-Chloro-5-fluorophenyl)pyridazin-3-yl)amino)hexahydrocyclopenta[c]pyrrol-2(1H)-yl)-2-methylpropan-2-ol

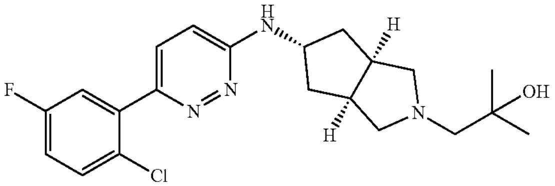 [SMILES: CC(C)(O)CN1C[C@H]2C[C@H](Nc3ccc(-c4cc(F)ccc4Cl)nn3)C[C@H]2C1]

(3aR,5s,6aS)—N-(6-(2-Chloro-5-fluorophenyl) pyridazin-3-yl)octahydrocyclopenta[c]pyrrol-5-amine hydrochloride (19.7 mg, 0.053 mmol) was dissolved in EtOH (1 mL), and DIPEA (0.028 mL, 0.16 mmol) was added, followed by isobutylene oxide (0.014 mL, 0.16 mmol). The resulting solution was heated to 70° C. for 4 h, after which time the reaction mixture was cooled to r.t., and the solvents were concentrated. The crude residue was purified by RP-HPLC (5-35% MeCN in 0.1% TFA aqueous solution over 5 min). The fractions containing product were basified with sat. $NaHCO_3$, and extracted with 3:1 chloroform/IPA (v/v). The combined organic extracts were filtered through a phase separator and concentrated to afford the title compound as a white solid (II mg, 51%). $^1H$-NMR (400 MHz, $CDCl_3$) δ 7.62 (d, J=9.3 Hz, 1H), 7.47 (dd, J=9.2, 3.1 Hz, 1H), 7.41 (dd, J=8.8, 5.0 Hz, 1H), 7.07-7.02 (m, 1H), 6.71 (d, J=9.3 Hz, 1H), 5.03 (d, J=4.8 Hz, 1H), 4.41 (br, 1H), 2.96 (br, 2H), 2.85 (br, 2H), 2.67 (br, 2H), 2.55 (br, 2H), 2.04-1.96 (m, 2H), 1.86-1.79 (m, 2H), 1.24 (m, 6H); ES-MS $[M+H]^+$=405.4.

Representative Synthesis 5. N-[4-[6-[[(3aR,5r,6aS)-2-(3,3-Dimethylbutyl)-3,3a,4,5,6,6a-hexahydro-1H-cyclopenta[c] pyrrol-5-yl]amino]pyridazin-3-yl]phenyl]acetamide

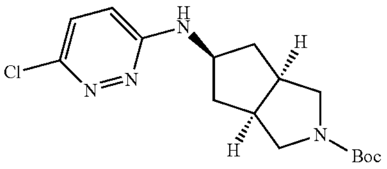 [SMILES: CC(C)(C)OC(=O)N1C[C@H]2C[C@@H](Nc3ccc(Cl)nn3)C[C@H]2C1]

tert-Butyl (3aR,5r,6aS)-5-((6-chloropyridazin-3-yl) amino)hexahydrocyclopenta[c]pyrrole-2(1H)-carboxylate. cis-N-Boc-5-oxo-octahydrocyclopenta[c]pyrrole (100 mg, 0.44 mmol) was dissolved in THF (1 mL) and DCE (1 mL), and 3-amino-6-chloropyridazine (288 mg, 2.22 mmol) was added, and the resulting solution was stirred for 10 min. Sodium triacetoxyborohydride (376 mg, 1.78 mmol) was then added, and the resulting solution was heated to 60° C. and stirred overnight, after which time the reaction was diluted with DCM and 3:1 chloroform/IPA solution, and the aqueous layer was extracted with 3:1 chloroform/IPA. The combined organic extracts were filtered through a phase separator and concentrated, and crude residue was purified by RP-HPLC. Fractions containing product were basified with sat. $NaHCO_3$, and extracted with 3:1 chloroform/IPA, and the combined organic extracts were filtered through a phase separator and concentrated to afford the title compound as a brown oil (15.1 mg, 10%). ES-MS $[M+H]^+$ =339.3.

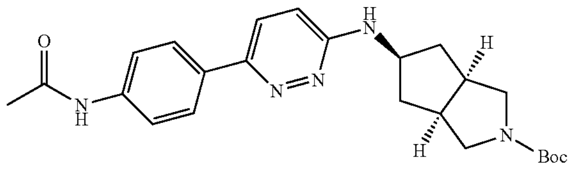 [SMILES: CC(=O)Nc1ccc(-c2ccc(N[C@@H]3C[C@@H]4CN(C(=O)OC(C)(C)C)C[C@@H]4C3)nn2)cc1]

tert-Butyl (3aR,5r,6aS)-5-((6-(4-acetamidophenyl) pyridazin-3-yl)amino)hexahydrocyclopenta[c]pyrrole-2 (1H)-carboxylate. tert-Butyl (3aR,5r,6aS)-5-((6-chloro-pyridazin-3-yl)amino)hexahydrocyclopenta[c]pyrrole-2 (1H)-carboxylate (15.1 mg, 0.045 mmol), $K_2CO_3$ (18.7 mg, 0.13 mmol), 4-acetylaminophenylboronic acid (9.6 mg, 0.053 mmol) and RuPhos-Pd-G3 (3.7 mg, 0.004 mmol) were combined in a sealed vial and placed under an inert atmosphere. 5:1 1,4-Dioxane/$H_2O$ solution (0.6 mL, degassed) was then added via syringe. The resulting mixture was heated to 120° C. under microwave irradiation for 30 min, after which time the reaction was cooled to r.t. and diluted with sat. $NaHCO_3$, and DCM. The aqueous layer was extracted with DCM, and the combined organic extracts were filtered through a phase separator and concentrated. The crude residue was purified by column chromatography (hex/EtOAc) to afford the title compound as a brown oil (3.9 mg, 20%). ES-MS [M+H]-=438.4.

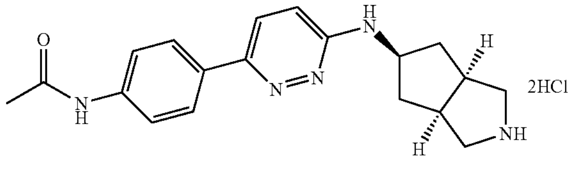 [SMILES: CC(=O)Nc1ccc(-c2ccc(N[C@H]3C[C@H]4CNC[C@H]4C3)nn2)cc1]

N-(4-(6-(((3aR,5r,6aS)-Octahydrocyclopenta[c]pyrrol-5-yl)amino)pyridazin-3-yl)phenyl)acetamide dihydrochloride. tert-Butyl (3aR,5r,6aS)-5-((6-(4-acetamidophenyl) pyridazin-3-yl)amino)hexahydrocyclopenta[c]pyrrole-2 (1H)-carboxylate (3.9 mg, 0.009 mmol) was dissolved in 1,4-dioxanes (0.5 mL) and 4M HCl in dioxanes solution (0.5 mL) was added dropwise. The resulting solution was stirred at r.t. for 30 min, after which time the solvents were concentrated under reduced pressure and the resulting white solid was used directly without further purification (3.9 mg, 100%). ES-MS $[M+H]^+$=338.4.

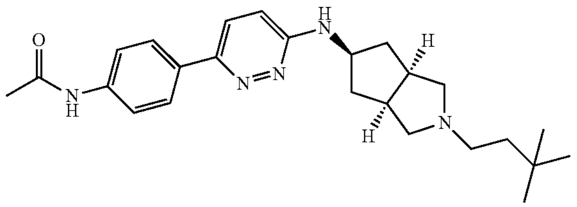 [SMILES: CC(=O)Nc1ccc(-c2ccc(N[C@@H]3C[C@@H]4CN(CCC(C)(C)C)C[C@@H]4C3)nn2)cc1]

N-[4-[6-[[(3aR,5r,6aS)-2-(3,3-Dimethylbutyl)-3,3a,4,5,6,6a-hexahydro-1H-cyclopenta[c]pyrrol-5-yl]amino] pyridazin-3-yl]phenyl)acetamide. N-(4-(6-(((3aR,5r,6aS)-Octahydrocyclopenta[c]pyrrol-5-yl)amino)pyridazin-3-yl) phenyl)acetamide dihydrochloride (3.3 mg, 0.009 mmol) was dissolved in THF (0.25 mL) and DCE (0.25 mL), and 3,3-dimethylbutyraldehyde (4.3 mg, 0.004 mmol) was added. The resulting mixture was stirred at r.t. for 6 h, after which time sodium triacetoxyborohydride (9.2 mg, 0.044 mmol) was then added, and the resulting solution was stirred at r.t. overnight, after which time the solvents were concentrated, and the crude residue was purified directly by RP-HPLC. Fractions containing product were basified with sat. $NaHCO_3$, and the aqueous layer was extracted with 3:1 chloroform/IPA. The combined organic extracts were filtered through a phase separator and concentrated to afford the title compound as a white solid (1.8 mg, 49%). $^1H$-NMR (400 MHz, $CDCl_3$) δ 7.95 (d, J=8.6 Hz, 2H), 7.58 (d, J=8.6 Hz, 2H), 7.51 (d, J=9.3 Hz, 1H), 6.54 (d, J=9.3 Hz, 1H), 4.67-4.62 (m, 1H), 2.81 (d, J=9.6 Hz, 2H), 2.75-2.67 (m, 2H), 2.47-2.43 (m, 2H), 2.22-2.15 (m, 7H), 1.74-1.44 (m, 4H), 0.94 (s, 9H). ES-MS $[M+H]^+$=422.4.

Representative Synthesis 6. (3aR,5s,6aS)-2-(1-(Tetrahydro-2H-pyran-4-yl)ethyl)-N-(6-(2,3,5-trifluorophenyl) pyridazin-3-yl)octahydrocyclopenta[c]pyrrol-5-amine

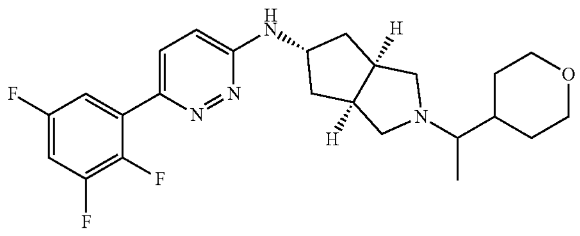 [SMILES: CC(C1CCOCC1)N1C[C@H]2C[C@H](Nc3ccc(-c4cc(F)cc(F)c4F)nn3)C[C@H]2C1]

(3aR,5s,6aS)—N-(6-(2,3,5-Trifluorophenyl)pyridazin-3-yl)octahydrocyclopenta[c]pyrrol-5-amine hydrochloride (10 mg, 0.027 mmol, 1 eq) and 1-(tetrahydro-2H-pyran-4-yl) ethan-1-one (17 mg, 0.13 mmol, 5 eq) were suspended in EtOH (0.5 mL), and titanium(IV) isopropoxide (40 μL, 0.13 mmol, 5 eq) was added. The resulting solution was stirred at 45° C. for 2 h, after which time $NaBH_4$ (5.1 mg, 0.13 mmol, 5 eq) was added. The resulting solution was stirred at r.t. for 1 h, after which time the reaction mixture was quenched with sat. $NaHCO_3$, and extracted with DCM. The combined organic extracts were filtered through a phase separator and concentrated, and crude residue was purified by RP-HPLC (5-35% MeCN in 0.1% TFA aqueous solution over 5 min). Fractions containing product were basified with sat. $NaHCO_3$, and extracted with 3:1 chloroform/IPA. The combined organic extracts were filtered through a phase separator and concentrated to afford the title compound as a white solid (1.9 mg, 16%). ES-MS $[M+H]^+$=447.4.

The compounds shown in Table 1a may be prepared similarly to the compounds described above, with appropriate starting materials. Additional starting materials that may be used to prepare compounds of the invention include tetrahydro-2H-pyran-4-carbaldehyde, (S)-(1,4-dioxan-2-yl) methanol), (R)-(1,4-dioxan-2-yl)methanol), (S)-1,4-dioxane-2-carboxylic acid, (R)-1,4-dioxane-2-carboxylic acid, (S)-tetrahydro-2H-pyran-2-carboxylic acid, (R)-tetrahydro-2H-pyran-2-carboxylic acid, (S)-tetrahydro-2H-pyran-3-carboxylic acid, (R)-tetrahydro-2H-pyran-3-carboxylic acid, 4-fluorotetrahydro-2H-pyran-4-carboxylic acid, 4-methoxytetrahydro-2H-pyran-4-carboxylic acid, 3-methyltetrahydro-2H-pyran-3-carboxylic acid, 2-methyltetrahydro-2H-pyran-2-carboxylic acid, 4-ethyltetrahydro-2H-pyran-4-carboxylic acid, 2,2-dimethyltetrahydro-2H-pyran-4-carboxylic acid, 3,3-dimethyltetrahydro-2H-pyran-4-carboxylic acid, 2,2,6,6-tetramethyltetrahydro-2H-pyran-4-carboxylic acid, (S)-tetrahydrofuran-3-carboxylic acid, (R)-tetrahydrofuran-3-carboxylic acid, (R)-(tetrahydrofuran-3-yl)methanol, 2-(tetrahydro-2H-pyran-4-yl)acetaldehyde, 4-methyltetrahydro-2H-pyran-4-carbaldehyde, 4-methyltetrahydro-2H-pyran-4-carboxylic acid, rac-(1R,2S,4S)-2-(bromomethyl)-7-oxabicyclo[2.2.1]heptane, rac-(1R,2R,4S)-2-(bromomethyl)-7-oxabicyclo[2.2.1]heptane, rac-(3aR,6aS)-hexahydro-2H-cyclopenta[b]furan-3a-carboxylic acid, octahydro-3aH-cyclohepta[b]furan-3a-carboxylic acid, 2,2,6,6-tetramethyltetrahydro-4H-pyran-4-one, 2-oxaspiro[3.3]heptan-6-one, 1,6-dioxaspiro[2.5]octane, cyclohexanecarbaldehyde, cycloheptanecarbaldehyde, cyclohexanone, picolinaldehyde, 6-methylpicolinaldehyde, 6-methoxypicolinaldehyde, 4-chloropicolinaldehyde, 6-chloropicolinaldehyde, 5-fluoropicolinaldehyde, 6-fluoropicolinaldehyde, 3-methylpicolinaldehyde, 1-(pyridin-2-yl)ethan-1-one, 6,7-dihydro-4H-pyrazolo[5,1-c][1,4]oxazine-2-carbaldehyde, 2,2-difluorobenzo[d][1,3]dioxole-5-carbaldehyde, pyridazine-4-carbaldehyde 1-fluorocyclohexane-1-carboxylic acid, 2-fluorobenzaldehyde, 2,3-difluorobenzaldehyde, 2,4-difluorobenzaldehyde, 2,6-difluorobenzoic acid and 3,3-difluorotetrahydro-2H-pyran-4-carboxylic acid.

TABLE 1a

| Cpd. No. | Name | Structure | ES-MS $[M+1]^+$ |
|---|---|---|---|
| 1 | (2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone | 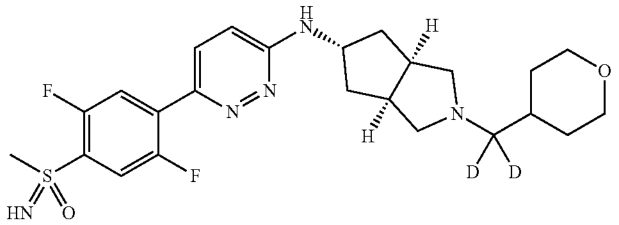 [SMILES: [2H]C([2H])(C1CCOCC1)N1C[C@H]2C[C@H](Nc3ccc(-c4cc(F)c(S(C)(=N)=O)cc4F)nn3)C[C@H]2C1] | 494.1 |
| 2 | imino(methyl)(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)-$\lambda^6$-sulfanone | 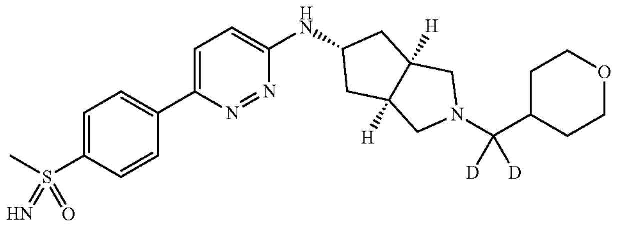 [SMILES: [2H]C([2H])(C1CCOCC1)N1C[C@H]2C[C@H](Nc3ccc(-c4ccc(S(C)(=N)=O)cc4)nn3)C[C@H]2C1] | 458.2 |
| 3 | (2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)((methyl-$d_3$)imino)-$\lambda^6$-sulfanone | 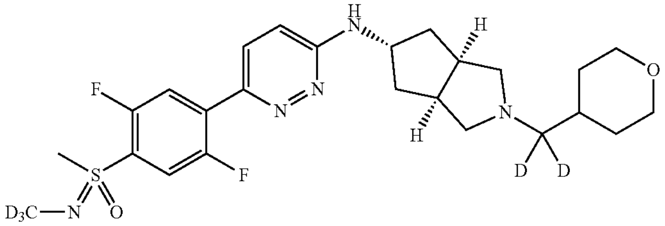 [SMILES: [2H]C([2H])([2H])N=S(C)(=O)c1cc(F)c(-c2ccc(N[C@H]3C[C@@H]4CN(C([2H])([2H])C5CCOCC5)C[C@@H]4C3)nn2)cc1F] | 511.2 |
| 4 | N-((2,5-difluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(methyl)(oxo)-$\lambda^6$-sulfaneylidene)acetamide | 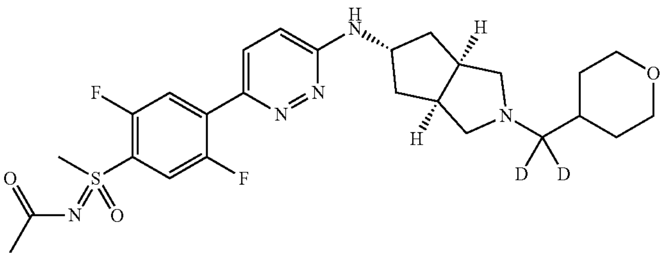 [SMILES: [2H]C([2H])(C1CCOCC1)N1C[C@H]2C[C@H](Nc3ccc(-c4cc(F)c(S(C)(=O)=NC(C)=O)cc4F)nn3)C[C@H]2C1] | 536.1 |

TABLE 1a-continued

| Cpd. No. | Name | Structure | ES-MS $[M+1]^+$ |
|---|---|---|---|
| 5 | (3-fluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-λ6-sulfanone | 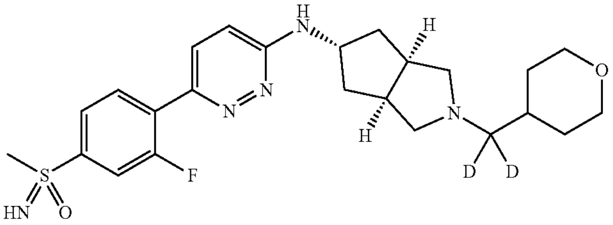 [SMILES: [2H]C([2H])(C1CCOCC1)N1C[C@H]2C[C@H](Nc3ccc(-c4ccc(S(C)(=N)=O)cc4F)nn3)C[C@H]2C1] | 476.1 |
| 6 | (2-fluoro-4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)(imino)(methyl)-λ6-sulfanone | 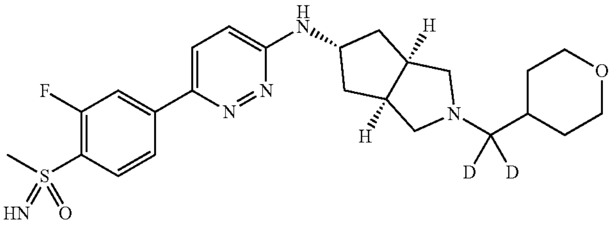 [SMILES: [2H]C([2H])(C1CCOCC1)N1C[C@H]2C[C@H](Nc3ccc(-c4ccc(S(C)(=N)=O)c(F)c4)nn3)C[C@H]2C1] | 476.1 |
| 7 | (2,5-difluoro-4-(6-(((3aR,5s,6aS)-2-((tetrahydro-2H-pyran-4-yl)methyl)octahydrocyclopenta[c]pyrrol-5-yl)amino)pyridazin-3-yl)phenyl)(imino)(methyl)-λ6-sulfanone | 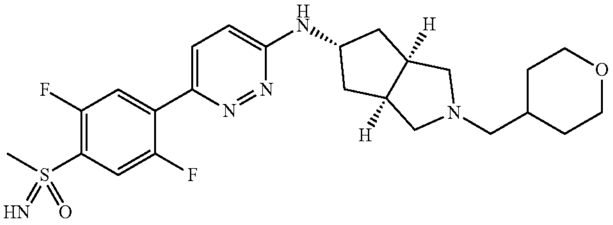 [SMILES: CS(=N)(=O)c1cc(F)c(-c2ccc(N[C@H]3C[C@@H]4CN(CC5CCOCC5)C[C@@H]4C3)nn2)cc1F] | 492.2 |
| 8 | (2,5-difluoro-4-(6-(((3aR,5s,6aS)-2-(pyridin-2-ylmethyl)octahydrocyclopenta[c]pyrrol-5-yl)amino)pyridazin-3-yl)phenyl)(imino)(methyl)-λ6-sulfanone | 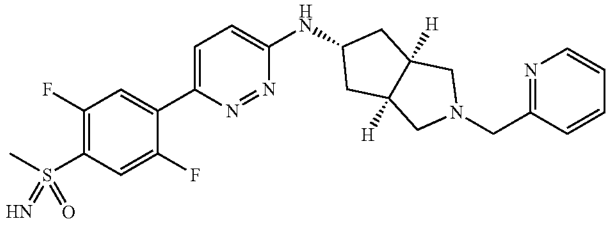 [SMILES: CS(=N)(=O)c1cc(F)c(-c2ccc(N[C@H]3C[C@@H]4CN(Cc5ccccn5)C[C@@H]4C3)nn2)cc1F] | 485.1 |
| 9 | (2,5-difluoro-4-(6-(((3aR,5s,6aS)-2-(2-(tetrahydro-2H-pyran-4-yl)ethyl)octahydrocyclopenta[c]pyrrol-5-yl)amino)pyridazin-3-yl)phenyl)(imino)(methyl)-λ6-sulfanone | 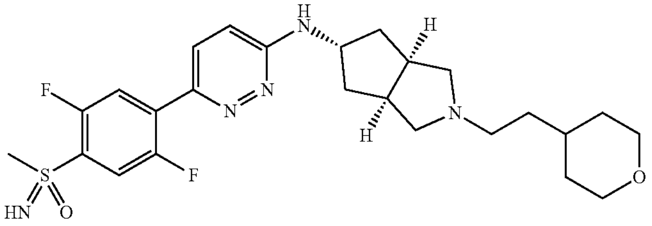 [SMILES: CS(=N)(=O)c1cc(F)c(-c2ccc(N[C@H]3C[C@@H]4CN(CCC5CCOCC5)C[C@@H]4C3)nn2)cc1F] | 506.1 |
| 10 | (4-(6-(((3aR,5s,6aS)-2-(cyclohexylmethyl)octahydrocyclopenta[c]pyrrol-5-yl)amino)pyridazin-3-yl)-2,5-difluorophenyl)(imino)(methyl)-λ6-sulfanone | 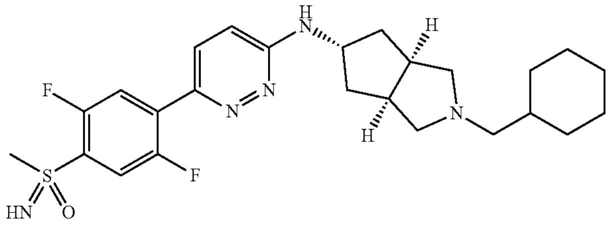 [SMILES: CS(=N)(=O)c1cc(F)c(-c2ccc(N[C@H]3C[C@@H]4CN(CC5CCCCC5)C[C@@H]4C3)nn2)cc1F] | 490.2 |

TABLE 1a-continued

| Cpd. No. | Name | Structure | ES-MS $[M + 1]^+$ |
|---|---|---|---|
| 11 | (2,5-difluoro-4-(6-(((3aR,5s,6aS)-2-((2,2,6,6-tetramethyltetrahydro-2H-pyran-4-yl)methyl-$d_2$)octahydrocyclopenta[c]pyrrol-5-yl)amino)pyridazin-3-yl)phenyl)(imino)(methyl)-$\lambda^6$-sulfanone | 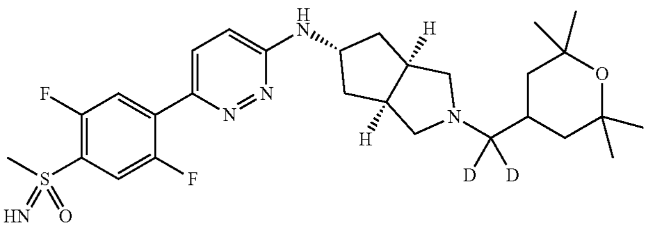 | 550.2 |
| 12 | methyl(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)phenyl)((trifluoromethyl)imino)-$\lambda^6$-sulfanone | 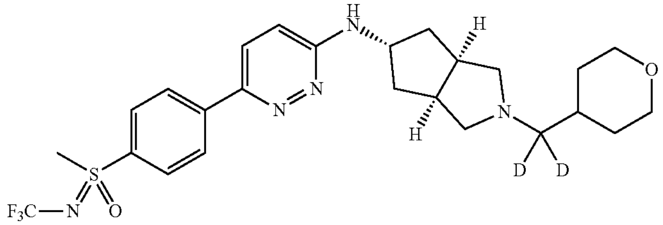 [SMILES: [2H]C([2H])(C1CCOCC1)N1C[C@H]2C[C@H](Nc3ccc(-c4ccc(S(C)(=O)=NC(F)(F)F)cc4)nn3)C[C@H]2C1] | 526.1 |
| 13 | imino(methyl)(4-(6-(((3aR,5s,6aS)-2-((tetrahydro-2H-pyran-4-yl)methyl-$d_2$)octahydrocyclopenta[c]pyrrol-5-yl)amino)pyridazin-3-yl)-2-(trifluoromethyl)phenyl)-$\lambda^6$-sulfanone | 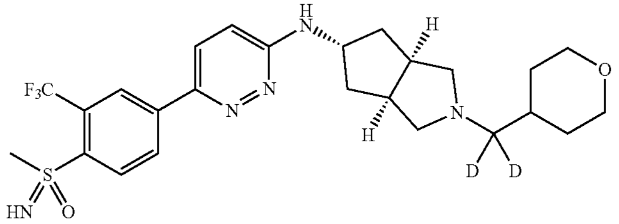 [SMILES: [2H]C([2H])(C1CCOCC1)N1C[C@H]2C[C@H](Nc3ccc(-c4ccc(S(C)(=N)=O)c(C(F)(F)F)c4)nn3)C[C@H]2C1] | 526.1 |

Biological Activity

A. Cell Lines Expressing Muscarinic Acetylcholine Receptors

Human or rat $M_4$ cDNA, along with the chimeric G protein $G_{qi5}$, were transfected into Chinese hamster ovary (CHO-K1) cells purchased from the American Type Culture Collection using Lipofectamine2000. $M_4/G_{qi5}$/CHO cells were grown in Ham's F-12 medium containing 10% heat-inactivated fetal bovine serum (FBS), 20 mM HEPES, 500 μg/mL G418 sulfate, and 200 μg/mL Hygromycin B.

B. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking G418 and hygromycin at 15,000 cells/20 μL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with assay buffer; the final volume was then aspirated to 20 μL. Next, 20 μL of a 2.3 μM stock of Fluo-4/acetoxymethyl ester (Invitrogen, Carlsbad, CA), prepared as a 2.3 mM stock in DMSO and mixed in a 1:1 ratio with 10% (w/v) Pluronic F-127 and diluted in assay buffer, was added to the wells and the cell plates were incubated for 50 min at 37° C. and 5% $CO_2$. Dye was removed by washing with the ELX 405 and the final volume was aspirated to 20 μL. Compound master plates were formatted in a 10 point concentration-response curve (CRC) format (1:3 dilutions) in 100% DMSO with a starting concentration of 10 or 1 mM using a BRAVO liquid handler (Agilent). Test compound CRCs were then transferred to daughter plates (240 nL) using the Echo acoustic plate reformatter (Labcyte, Sunnyvale, CA) and then diluted into assay buffer (40 μL) to a 2× stock using a Thermo Fisher Combi (Thermo Fisher Scientific, Waltham, MA).

Calcium flux was measured using the Functional Drug Screening System (FDSS) 6000 or 7000 (Hamamatsu Corporation, Tokyo, Japan) as an increase in the fluorescent static ratio. Compounds were applied to cells (20 μL, 2×) using the automated system of the FDSS at 2 seconds into the protocol and the data were collected at 1 Hz. At 143 s, 10 μL of an $EC_{20}$ concentration of the muscarinic receptor agonist acetylcholine was added (5×), followed by the addition of 12 μL of an $EC_{80}$ concentration of acetylcholine at the 268 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response; for the purposes of the tables herein, an $IC_{50}$ (inhibitory concentration 50) was calculated as a concentration-dependent decrease of the response elicited by an $EC_{80}$ concentration of acetylcholine. Concentration-response curves were generated using a four-parameter logistical equation in XLFit curve fitting software (IDBS, Bridgewater, NJ) for Excel (Microsoft, Redmond, WA) or Prism (GraphPad Software, Inc., San Diego, CA) or the Dotmatics software platform (Dotmatics, Bishop's Stortford, UK).

The above described assay was also operated in a second mode where an appropriate fixed concentration of the present compounds were added to the cells after establishment of a fluorescence baseline for about 3 seconds, and the response in cells was measured. 140 s later, a full concentration-response range consisting of increasing concentrations of agonist was added and the calcium response (maximum-local minima response) was measured. The $EC_{80}$ values for the agonist in the presence or absence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

C. Activity of Compounds in a mAChR $M_4$ Cell-Based Assay

Compounds were synthesized as described above. Activity ($IC_{50}$ and $E_{min}$) was determined in the mAChR $M_4$ cell-based functional assay as described above and the data are shown in Table 2.

TABLE 2

| | Human $M_4$ | |
|---|---|---|
| Cpd. No. | $IC_{50}$ (nM) | $E_{min}$ (%)* |
| 1 | 13.4 | 4 |
| 2 | 39.6 | 2 |
| 3 | 18.5 | 3 |
| 4 | 584 | 6 |
| 5 | 75.4 | 3 |
| 6 | 188 | 3 |
| 7 | 40.0 | 3 |
| 8 | 560 | 7 |
| 9 | 18.4 | 3 |
| 10 | 1.8 | 2 |
| 11 | 86.2 | 3 |
| 12 | 43.4 | 2 |
| 13 | 8.6 | 3 |

*% ACh maximum at 30 μM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I), (I)

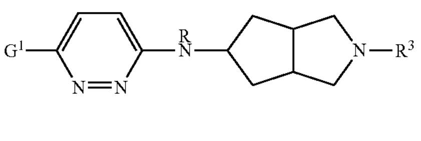

or a pharmaceutically acceptable salt thereof, wherein:

$G^1$ is

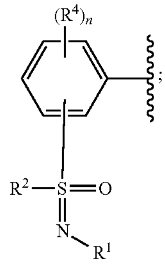

R is hydrogen, $C_{1-4}$alkyl, $C_{3-4}$cycloalkyl, or —$C_{1-3}$alkylene-$C_{3-4}$cycloalkyl;

$R^1$ is hydrogen, $C_{1-4}$alkyl, $C_{1-2}$fluoroalkyl, $C_{3-4}$cycloalkyl, —$C_{1-3}$alkylene-$C_{3-4}$cycloalkyl, or —C(O) $C_{1-4}$alkyl;

$R^2$ is $C_{1-4}$alkyl, $C_{1-2}$fluoroalkyl, $C_{3-4}$cycloalkyl, or —$C_{1-3}$alkylene-$C_{3-4}$cycloalkyl;

$R^3$ is -$L^1$-$G^2$, $G^2$, -$L^2$-$G^2$, -$L^2$-$L^1$-$G^2$, —$C_{2-6}$alkylene-$R^{3a}$, $C_{3-7}$alkyl, or $C_{3-7}$haloalkyl;

$R^4$, at each occurrence, is independently halogen, cyano, $C_{1-4}$alkyl, $C_{1-2}$fluoroalkyl, OH, —$OC_{1-4}$alkyl, or —$OC_{1-2}$fluoroalkyl;

n is 0, 1, 2, 3, or 4;

$L^1$ is $C_{1-5}$alkylene;

$L^2$ is 1,1-cyclopropylene;

$G^2$ is a 4- to 12-membered heterocyclyl, a 6- to 12-membered aryl, a 5- to 12-membered heteroaryl, or a $C_{3-12}$carbocyclyl optionally fused to a 6-membered arene, wherein $G^2$ is optionally substituted with 1-5 substituents independently selected from the group consisting of halogen, cyano, oxo, $C_{1-4}$alkyl, $C_{1-4}$haloalkyl, —$OR^{13}$, —$N(R^{13})_2$, —$C_{1-3}$alkylene-$OR^{13}$, and —$C_{1-3}$alkylene-$N(R^{13})_2$;

$R^{3a}$ is —$OR^{14}$ or —$N(R^{14})_2$;

$R^{13}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{13}$, together with a nitrogen to which the two $R^{13}$ attach form a 4- to 6-membered heterocyclic ring optionally substituted with 1-4 substituents independently selected from the group consisting of halogen and $C_1$-4alkyl;

$R^{14}$, at each occurrence, is independently hydrogen, $C_{1-4}$alkyl, $C_{1-4}$haloalkyl, $G^3$, or —$C_{1-3}$alkylene-$G^3$, wherein alternatively two $R^{14}$, together with a nitrogen to which the two $R^{14}$ attach form a 4- to 6-membered heterocyclic ring optionally substituted with 1-4 substituents independently selected from the group consisting of halogen and $C_{1-4}$alkyl;

$G^3$ is phenyl, a monocyclic 5- to 6-membered heteroaryl, a monocyclic 4- to 8-membered heterocyclyl, or a monocyclic $C_{3-8}$cycloalkyl, wherein $G^3$ is optionally substituted with 1-5 substituents independently selected from the group consisting of halogen, cyano, $C_{1-4}$alkyl, $C_{1-4}$haloalkyl, oxo, —$OR^{15}$, and —$N(R^{15})_2$; and $R^{15}$, at each occurrence, is independently hydrogen, $C_{1-4}$alkyl, $C_{1-4}$haloalkyl, $C_{3-4}$cycloalkyl, or —$C_{1-3}$alkylene-$C_{3-4}$cycloalkyl, wherein alternatively two $R^{15}$, together with a nitrogen to which the two $R^{15}$ attach form a 4- to 6-membered heterocyclic ring optionally substituted with 1-4 substituents independently selected from the group consisting of halogen and $C_{1-4}$alkyl.

2. The compound of claim 1, or a pharmaceutically acceptable salt thereof, wherein $G^1$ is

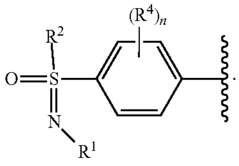

3. The compound of claim 1, or a pharmaceutically acceptable salt thereof, wherein $R^1$ is hydrogen.

4. The compound of claim 1, or a pharmaceutically acceptable salt thereof, wherein $R^1$ is $C_{1-4}$alkyl, $C_{1-2}$fluoroalkyl, or —$C(O)C_{1-4}$alkyl.

5. The compound of claim 1, or a pharmaceutically acceptable salt thereof, wherein $R^2$ is $C_{1-4}$alkyl.

6. The compound of claim 1, or a pharmaceutically acceptable salt thereof, wherein $R^4$, at each occurrence, is independently fluoro or $CF_3$.

7. The compound of claim 1, or a pharmaceutically acceptable salt thereof, wherein n is 0, 1, or 2.

8. The compound of claim 1, or a pharmaceutically acceptable salt thereof, wherein $R^3$ is -$L^1$_$G^2$.

9. The compound of claim 1, or a pharmaceutically acceptable salt thereof, wherein $G^2$ is the optionally substituted 4- to 12-membered heterocyclyl.

10. The compound of claim 9, or a pharmaceutically acceptable salt thereof, wherein $G^2$ is

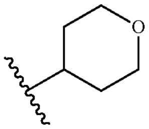

or

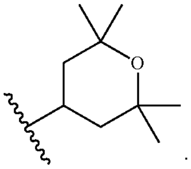

.

11. The compound of claim 1, or a pharmaceutically acceptable salt thereof, wherein $G^2$ is the optionally substituted 5- to 12-membered heteroaryl.

12. The compound of claim 11, wherein $G^2$ is

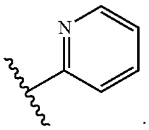 [SMILES: *c1ccccn1]

.

13. The compound of claim 1, or a pharmaceutically acceptable salt thereof, wherein $G^2$ is the optionally substituted $C_{3-12}$carbocyclyl optionally fused to a 6-membered arene.

14. The compound of claim 13, or a pharmaceutically acceptable salt thereof, wherein $G^2$ is

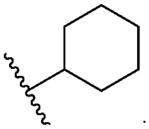 [SMILES: *C1CCCCC1]

.

15. The compound of claim 1, or a pharmaceutically acceptable salt thereof, wherein $L^1$ is $CH_2$.

16. The compound of claim 15, or a pharmaceutically acceptable salt thereof, wherein the $CH_2$ at $L^1$ is $CD_2$.

17. The compound of claim 1, or a pharmaceutically acceptable salt thereof, wherein $L^1$ is $CH_2CH_2$.

18. The compound of claim 1, or a pharmaceutically acceptable salt thereof, wherein R is hydrogen.

19. A pharmaceutical composition comprising the compound of claim 1, or a pharmaceutically acceptable salt thereof, and a pharmaceutically acceptable carrier.

20. A method for treating a disorder in a subject, wherein the subject would benefit from antagonism of mAChR $M_4$, comprising administering to the mammal a therapeutically effective amount of the compound of claim 1, or a pharmaceutically acceptable salt thereof.

* * * * *